US006737549B2

(12) United States Patent
Wolf et al.

(10) Patent No.: US 6,737,549 B2
(45) Date of Patent: May 18, 2004

(54) ORGANOMETALLIC MONOACYLALKYLPHOSPHINES

(75) Inventors: Jean-Pierre Wolf, Maisprach (CH); Gebhard Hug, Rheinfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/871,373

(22) Filed: May 31, 2001

(65) Prior Publication Data

US 2002/0026049 A1 Feb. 28, 2002

(30) Foreign Application Priority Data

Jun. 8, 2000 (CH) .......................................... 1133/00

(51) Int. Cl.[7] .............................................. C07F 9/02
(52) U.S. Cl. ........................... 568/14; 568/15; 522/64
(58) Field of Search ...................... 568/14, 15; 522/64

(56) References Cited

U.S. PATENT DOCUMENTS

| | | | | |
|---|---|---|---|---|
| 4,522,693 | A | 6/1985 | Henne et al. | 204/159.15 |
| 4,737,593 | A | 4/1988 | Ellrich et al. | 568/15 |
| 5,218,009 | A | 6/1993 | Rutsch et al. | 522/16 |
| 5,368,985 | A | 11/1994 | Rutsch et al. | 430/269 |
| 5,399,770 | A | 3/1995 | Leppard et al. | 568/15 |
| 5,534,559 | A | 7/1996 | Leppard et al. | 522/64 |
| 5,721,292 | A | 2/1998 | Leppard et al. | 522/64 |
| 5,942,290 | A | 8/1999 | Leppard et al. | 427/510 |
| 6,020,528 | A | 2/2000 | Leppard et al. | 568/15 |
| 6,284,813 | B1 | 9/2001 | Leppard et al. | 522/8 |
| 2001/0031898 | A1 | 10/2001 | Wolf et al. | 568/13 |

FOREIGN PATENT DOCUMENTS

| | | |
|---|---|---|
| DE | 3139984 | 4/1983 |
| DE | 19907957 | 9/1999 |
| EP | 0040721 | 12/1981 |
| EP | 0495751 | 7/1992 |
| EP | 0501702 | 9/1992 |
| EP | 0738928 | 10/1996 |
| EP | 1106627 | 6/2001 |
| ES | 2059261 | 11/1994 |
| GB | 2259704 | 3/1993 |
| GB | 2292740 | 3/1996 |
| WO | 00/32612 | 6/2000 |

OTHER PUBLICATIONS

C. Liotta et al., Tetrahedron Letters, vol. 25, No. 12, pp. 1249–1252, (1984).
Derwent Abstr. 91349 D/50 for EP 0040721 (1981).
Derwent Abstr. 41862 K/18 for DE 3139984 (1983).
Derwent Abstr. 1999–474081 [40] for JP 11199610 (1999).
Derwent Abstr. 1999–509829/43 for DE 19907957 (1999).
Chem. Abstr. 125:99768 for J. Am. Chem. Soc. (1996), 118(27), pp. 6477–6489.
Derwent Abstr. 1994–351097 [51] for ES 2059261 (1994).
Derwent Abstr. 92–243582/30 for EP 0495751 (1992).

*Primary Examiner*—Susan Berman
(74) *Attorney, Agent, or Firm*—Tyler A. Stevenson

(57) ABSTRACT

Compounds of the formula I (I)

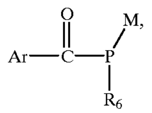

Ar is a group

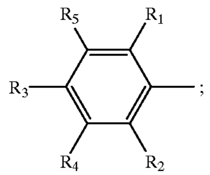

or unsubstituted or substituted cyclopentyl, cyclohexyl, naphthyl, biphenylyl or an O-, S- or N-containing 5- or 6-membered heterocyclic ring; $R_1$ and $R_2$ are $C_1$–$C_{20}$alkyl, $OR_{11}$, $CF_3$ or halogen; $R_3$, $R_4$ and $R_5$ are hydrogen, $C_1$–$C_{20}$alkyl, $OR_{11}$ or halogen; $R_6$ is unsubstituted or substituted $C_1$–$C_{24}$alkyl, $C_2$–$C_{24}$alkyl, which is interrupted by O, S or $NR_{14}$ and is unsubstituted or substituted; $C_2$–$C_{24}$alkenyl, uninterrupted or interrupted by O, S or $NR_{14}$ and unsubstituted or substituted; unsubstituted or substituted $C_7$–$C_{24}$arylalkyl; $C_4$–$C_{24}$cycloalkyl, uninterrupted or interrupted by O, S and/or $NR_{14}$; or $C_8$–$C_{24}$arylcycloalkyl; $R_{11}$ is $C_1$–$C_{20}$alkyl, $C_3$–$C_8$cycloalkyl, phenyl, benzyl or $C_2$–$C_{20}$alkyl, interrupted by O or S and unsubstituted or substituted; $R_{12}$ and $R_{13}$ are hydrogen, $C_1$–$C_{20}$alkyl, $C_3$–$C_8$cycloalkyl, phenyl, benzyl or $C_2$–$C_{20}$alkyl, interrupted by O atoms and unsubstituted or substituted; or $R_{12}$ and $R_{13}$ together are $C_3$–$C_5$alkylene, uninterrupted or interrupted by O, S or $NR_{14}$; $R_{14}$ is hydrogen, phenyl, $C_1$–$C_{12}$alkyl or $C_2$–$C_{12}$alkyl, interrupted by O or S and unsubstituted or substituted; and M is hydrogen, Li, Na or K; are valuable intermediates for the preparation of unsymmetrical bisacylphosphine oxides and monoacylphosphine oxides.

5 Claims, No Drawings

ORGANOMETALLIC MONOACYLALKYLPHOSPHINES

The present application relates to organometallic monoacylalkylphosphines, to the preparation thereof, and to the use thereof as starting materials for the preparation of unsymmetrical mono- and bisacylphosphines, -phosphine oxides or sulfides.

Various metalated phosphines have become known as intermediates in the preparation of a-cylphosphine oxides. Thus, for example in EP 40721, acylphosphines are obtained by reaction of acyl halides with metalated diorganophosphines or silylated phosphines or diorganophosphines.

By oxidation of the acyldiorganophosphines, the corresponding acylphosphine oxide photoinitiators can be prepared therefrom. WO 00/32612 discloses a one-pot process for the preparation of bisacylphosphine oxides in which dichloroorganophosphines are metalated, then reacted with acyl halides to give the corresponding acylphosphines and then, by oxidation or sulfurization, the bisacylphosphine oxides or sulfides are obtained.

Alkylacylphosphines and the corresponding metalated compounds are not known in the prior U.S. Pat. No. 5,399,770 discloses a bisacylphosphine oxide having two different acyl groups, and U.S. Pat. No. 5,218,009 specifically discloses a monoacylphosphine oxide having two different non-acyl substituents on the phosphorus atom.

For the technology, readily accessible starting materials for the preparation of acylphosphine oxides and sulfides are of great importance. Of particular interest are starting materials which permit the preparation of "unsymmetrical" bisacylphosphine oxides and sulfides, i.e. those with two different acyl groups, in a simple manner.

A process for the preparation of metalated alkylacylphosphines which are suitable as starting materials for the preparation of acylphosphine oxide or acylphosphine sulfide photoinitiators has been found. The majority of the phosphines, phosphine oxides and phosphine sulfides obtained are novel.

The invention provides compounds of the formula I (I)

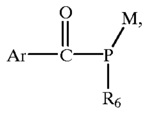

in which Ar is a group

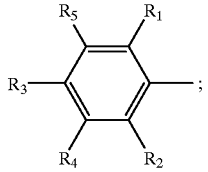

or Ar is cyclopentyl, cyclohexyl, naphthyl, anthracyl, biphenylyl or an O-, S- or N-containing 5- or 6-membered heterocyclic ring, where the radicals cyclopentyl, cyclohexyl, naphthyl, anthracyl, biphenylyl and 5- or 6-membered heterocyclic ring are unsubstituted or substituted by halogen, $C_1$–$C_4$alkyl and/or $C_1$–$C_4$alkoxy;

$R_1$ and $R_2$ independently of one another are $C_1$–$C_{20}$alkyl, $OR_{11}$, $CF_3$ or halogen;

$R_3$, $R_4$ and $R_5$ independently of one another are hydrogen, $C_1$–$C_{20}$alkyl, $OR_{11}$ or halogen; or in each case two of the radicals $R_1$, $R_2$, $R_3$, $R_4$ and $R_5$ together form $C_1$–$C_{20}$alkylene, which can be interrupted by O, S or $NR_{14}$;

$R_6$ is $C_1$–$C_{24}$alkyl, unsubstituted or substituted by cycloalkenyl, phenyl, CN, $C(O)R_{11}$, $C(O)OR_{11}$, $C(O)N(R_{14})_2$, $OC(O)R_{11}$, $OC(O)OR_{11}$, $N(R_{14})C(O)N(R_{14})$, $OC(O)NR_{14}$, $N(R_{14})C(O)OR_{11}$, cycloalkyl, halogen, $OR_{11}$, $SR_{11}$, $N(R_{12})(R_{13})$ or

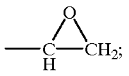

$C_2$–$C_{24}$alkyl which is interrupted once or more than once by nonconsecutive O, S or $NR_{14}$ and which is unsubstituted or substituted by phenyl, $OR_{11}$, $SR_{11}$, $N(R_{12})(R_{13})$, CN, $C(O)R_{11}$, $C(O)OR_{11}$, $C(O)N(R_{14})_2$ and/or

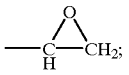

$C_2$–$C_{24}$alkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_5$–$C_{24}$cycloalkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_7$–$C_{24}$arylalkyl which is unsubstituted or substituted on the aryl group by $C_1$–$C_{12}$alkyl, $C_1$–$C_{12}$alkoxy or halogen;

$C_4$–$C_{24}$cycloalkyl which is uninterrupted or interrupted once or more than once by O, S and/or $NR_{14}$ and which is unsubstituted or substituted by $OR_{11}$, $SR_{11}$ or $N(R_{12})(R_{13})$;

or $C_8$–$C_{24}$arylcycloalkyl or $C_8$–$C_{24}$arylcycloalkenyl;

$R_{11}$ is H, $C_1$–$C_{20}$alkyl, $C_2$–$C_{20}$alkenyl, $C_3$–$C_8$cycloalkyl, phenyl, benzyl or $C_2$–$C_{20}$alkyl which is interrupted once or more than once by O or S and which is unsubstituted or is substituted by OH and/or SH;

$R_{12}$ and $R_{13}$ independently of one another are hydrogen, $C_1$–$C_{20}$alkyl, $C_3$–$C_8$cycloalkyl, phenyl, benzyl or $C_2$–$C_{20}$alkyl which is interrupted once or more than once by nonconsecutive O atoms and which is unsubstituted or substituted by OH and/or SH; or $R_{12}$ and $R_{13}$ together are $C_3$–$C_5$alkylene which is uninterrupted or interrupted by O, S or $NR_{14}$;

$R_{14}$ is hydrogen, phenyl, $C_1$–$C_{12}$alkyl or $C_2$–$C_{12}$alkyl which is interrupted once or more than once by O or S and which is unsubstituted or substituted by OH and/or SH; and M is hydrogen, Li, Na or K.

$C_1$–$C_{24}$Alkyl is linear or branched and is, for example, $C_2$–$C_{24}$alkyl, $C_1$–$C_{20}$alkyl, $C_1$–$C_{18}$alkyl, $C_1$–$C_{12}$alkyl, $C_1$–$C_8$alkyl, $C_1$–$C_6$alkyl or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl, icosyl or tetraicosyl.

For example, $R_1$, $R_2$, $R_3$, $R_1'$, $R_2'$ and $R_3'$ are $C_1$–$C_8$alkyl, in particular $C_1$–$C_6$alkyl, preferably $C_1$–$C_4$alkyl, particularly preferably methyl.

$C_1$–$C_{20}$Alkyl, $C_1$–$C_{18}$alkyl, $C_1$–$C_{12}$alkyl, $C_1$–$C_6$alkyl and $C_1$–$C_4$alkyl are likewise linear or branched and have, for example, the meanings given above apart from the corresponding number of carbon atoms.

$R_5$, $R_6$, $R_7$, $R_8$, $R_9$, $R_{10}$, $R_{11}$, $R_{12}$, $R_{13}$, $R_{19}$, $R_{20}$, $R_{21}$, $R_{22}$ and $R_{23}$ are, for example, $C_1$–$C_8$alkyl, in particular $C_1$–$C_6$alkyl, preferably $C_1$–$C_4$alkyl, for example methyl or butyl.

$C_2$–$C_{24}$Alkyl which is interrupted once or more than once by O, S or $NR_{14}$ is, for example, interrupted 1–9 times, e.g. 1–7 times or once or twice, by O, S or $NR_{14}$. If the radicals are interrupted by two or more O, S or $NR_{14}$, then the O atoms, S atoms or $NR_{14}$ groups are in each case separated from one another by at least one methylene group. The O atoms, S atoms or $NR_{14}$ groups are thus not directly consecutive. The alkyl radical can be linear or branched. For example, structural units such as $—CH_2—O—CH_3$, $—CH_2CH_2—O—CH_2CH_3$, $—[CH_2CH_2O]_z—CH_3$, where z=1 to 9, $—(CH_2CH_2O)_7CH_2CH_3$, $—CH_2—CH(CH_3)—O—CH_2—CH_2CH_3$, $—CH_2—CH(CH_3)—O—CH_2—CH_3$, $—CH_2SCH_3$ or $—CH_2—N(CH_3)_2$ arise.

$C_2$–$C_{20}$Alkyl, $C_2$–$C_{18}$alkyl, $C_2$–$C_{12}$alkyl which are interrupted by O and optionally by S are likewise linear or branched and can, for example, have the meanings given above apart from the given number of carbon atoms. The O atoms are not consecutive here either.

$C_1$–$C_{18}$Haloalkyl is $C_1$–$C_{18}$alkyl as described above which is mono- or polysubstituted by halogen. This is, for example, perfluorinated $C_1$–$C_{18}$alkyl. Examples are chloromethyl, trichloromethyl, trifluoromethyl or 2-bromopropyl, in particular trifluoromethyl or trichloromethyl.

$C_3$–$C_{24}$Cycloalkyl, e.g. $C_4$–$C_{24}$cycloalkyl, $C_5$–$C_{12}$cycloalkyl, $C_4$–$C_{12}$cycloalkyl, $C_3$–$C_{12}$cycloalkyl, $C_3$–$C_8$cycloalkyl, stands both for individual alkyl ring systems and also bridged alkyl ring systems. Furthermore, the radicals can also contain linear or branched alkyl groups (as described above apart from the corresponding number of carbon atoms). Examples are cyclopropyl, cyclopentyl, cyclohexyl, cyclooctyl, cyclododecyl, cycloicosyl, in particular cyclopentyl and cyclohexyl, preferably cyclohexyl. Further examples are

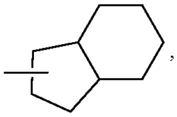,
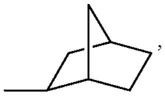,
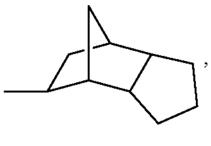,
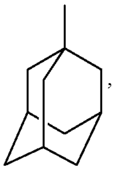,
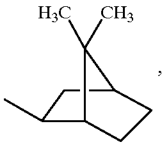,
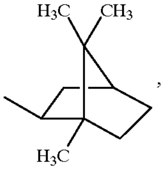,
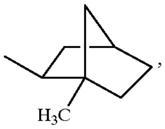,
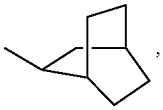,
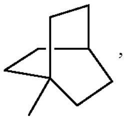, -continued

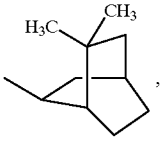, $C_3$–$C_8$Cycloalkyl, e.g. $C_3$–$C_6$cycloalkyl, can have the meanings given above apart from the corresponding number of carbon atoms.

$C_3$–$C_{18}$Cycloalkyl substituted by $C_1$–$C_{20}$alkyl, $OR_{11}$, $CF_3$ or halogen is preferably substituted in both ortho positions of the cycloalkyl ring. Preference is given to 2,4,6-trimethylcyclohexyl and 2,6-dimethoxycyclohexyl.

$C_2$–$C_{24}$Alkenyl radicals are mono- or polyunsaturated, and are linear or branched and are, for example, $C_2$–$C_{18}$alkenyl, $C_2$–$C_8$alkenyl, $C_2$–$C_6$alkenyl or $C_2$–$C_4$alkenyl. Examples are vinyl, allyl, methallyl, 1,1-dimethylallyl, 1-butenyl, 2-butenyl, 1,3-pentadienyl, 1-hexenyl, 1-octenyl, decenyl or dodecenyl, in particular allyl. $C_2$–$C_{18}$Alkenyl has the same meanings as given above apart from the corresponding number of carbon atoms.

If $C_2$–$C_{24}$alkenyl radicals are interrupted, for example, by O, then the following structures are, for example, included: $—(CH_2)_y—O—(CH_2)_x—CH{=}CH_2$, $—(CH_2)_y—O—(CH_2)_x—C(CH_3){=}CH_2$ or $—(CH_2)_y—O—CH{=}CH_2$, where x and y independently of one another are a number from 1 to 21.

$C_3$–$C_{24}$Cycloalkenyl, e.g. $C_5$–$C_{12}$cycloalkenyl, $C_3$–$C_{12}$cycloalkenyl, $C_3$–$C_8$cycloalkenyl, stands both for individual alkyl ring systems and also bridged alkyl ring systems and can be mono- or polyunsaturated, e.g. mono- or diunsaturated. Furthermore, the radicals can also contain linear or branched alkyl groups (as described above apart from the corresponding number of carbon atoms). Examples are cyclopropenyl, cyclopentenyl, cyclohexenyl, cyclooctenyl, cyclododecenyl, cycloicosenyl, in particular cyclopentenyl and cyclohexenyl, preferably cyclohexenyl.

$C_7$–$C_{24}$Arylalkyl is, for example, $C_7$–$C_{16}$arylalkyl, $C_7$–$C_1$larylalkyl. The alkyl radical in this group can either be linear or branched. Examples are benzyl, phenylethyl, α-methylbenzyl, phenylpentyl, phenylhexyl, α,α-dimethylbenzyl, naphthylmethyl, naphthylethyl, naphthyleth-1-yl or naphthyl-1-methyl-eth-1-yl, in particular benzyl. Substituted $C_7$–$C_{24}$arylalkyl is substituted one to four times, e.g. once, twice or three times, in particular once or twice, on the aryl ring.

$C_8$–$C_{24}$Arylcycloalkyl is e.g. $C_9$–$C_{16}$arylcycloalkyl, $C_9$–$C_{13}$arylcycloalkyl and is cycloalkyl which is fused with one or more aryl rings. Examples are

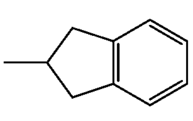,
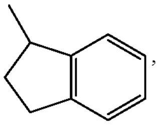,
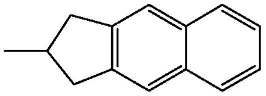,
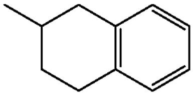,

-continued

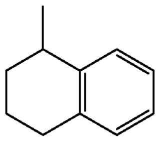

etc.

$C_1$–$C_{12}$Alkylthio stands for linear or branched radicals and is, for example, $C_1$–$C_8$alkylthio, $C_1$–$C_6$alkylthio or $C_1$–$C_4$alkylthio. Examples are methylthio, ethylthio, propylthio, isopropylthio, n-butylthio, sec-butylthio, isobutylthio, tert-butylthio, pentylthio, hexylthio, heptylthio, 2,4,4-trimethylpentylthio, 2-ethylhexylthio, octylthio, nonylthio, decylthio or dodecylthio, in particular methylthio, ethylthio, propylthio, isopropylthio, n-butylthio, sec-butylthio, isobutylthio, tert-butylthio, preferably methylthio.

$C_1$–$C_8$Alkylthio is likewise linear or branched and has, for example, the meanings given above apart from the corresponding number of carbon atoms.

$C_1$–C24Alkylene is linear or branched and is, for example, $C_1$–$C_{20}$alkylene, $C_1$–$C_{12}$alkylene, $C_1$–$C_8$alkylene, $C_2$–$C_8$alkylene, $C_1$–$C_4$alkylene, for example methylene, ethylene, propylene, isopropylene, n-butylene, sec-butylene, isobutylene, tert-butylene, pentylene, hexylene, heptylene, octylene, nonylene, decylene, dodecylene, tetradecylene, heptadecylene, octadecylene, icosylene or e.g. $C_1$–$C_{12}$alkylene, for example ethylene, decylene,

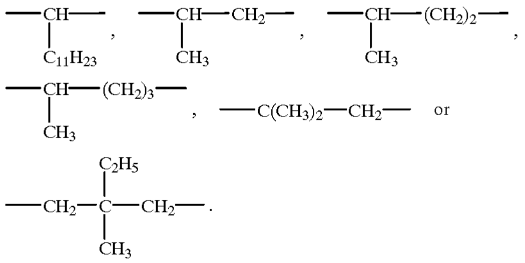

$C_2$–$C_{18}$Alkylene is also linear or branched, e.g. $C_2$–$C_8$alkylene or $C_2$–$C_4$alkylene and has the meanings given above apart from the corresponding number of carbon atoms.

If $C_2$–$C_{18}$alkylene is interrupted once or more than once by O, S or $NR_{14}$, then it is, for example, interrupted 1–9 times, e.g. 1–7 times or once or twice by O, S or $NR_{14}$, and, for example, structural units such as $—CH_2—O—CH_2—$, $—CH_2CH_2—O—CH_2CH_2—$, $—[CH_2CH_2O]_z—$, where z=1 to 9, $—(CH_2CH_2O)_7CH_2CH_2—$, $—CH_2—CH(CH_3)—O—CH_2—CH(CH_3)—$, $—CH_2—S—CH_2—$, $—CH_2CH_2—S—CH_2CH_2—$, $—CH_2CH_2CH_2—S—CH_2CH_2CH_2—$, $—(CH_2)_3—S—(CH_2)_3—S—(CH_2)_3—$, $—CH_2—(NR_{14})—CH_2—$ or $—CH_2CH_2—(NR_{14})—CH_2CH_2—$ arise. The alkylene radicals can be linear or branched and, if the alkylene radicals are interrupted by two or more O, S or $NR_{14}$ groups, then the O, S and $NR_{14}$ are not consecutive, but in each case are separated from one another by at least one methylene group.

$C_2$–$C_{24}$Alkenylene is mono- or polyunsaturated and linear or branched and e.g. $C_2$–$C_{18}$alkenylene or $C_2$–$C_8$alkenylene. Examples are ethenylene, propenylene, butenylene, pentenylene, hexenylene, octenylene, e.g. 1-propenylene, 1-butenylene, 3-butenylene, 2-butenylene, 1,3-pentadienylene, 5-hexenylene or 7-octenylene.

$C_2$–$C_{24}$Alkenylene, interrupted once or more than once by O, S, $NR_{14}$, is mono- or poly-unsaturated and linear or branched and is, for example, interrupted 1–9 times, e.g. 1–7 times or once or twice, by O, S or $NR_{14}$, where in the case of two or more O, S or $NR_{14}$, these are in each case separated from one another by at least one methylene group. Here, the meanings for $C_2$–$C_{24}$alkenylene are as defined above.

$C_4$–$C_{18}$Cycloalkylene is linear or branched and can be either an individual ring or bridged alkyl rings, for example adamantyl. It is e.g. $C_4$–$C_{12}$cycloalkylene or $C_4$–$C_8$cycloalkylene, for example cyclopentylene, cyclohexylene, cyclooctylene, cyclododecylene, in particular cyclopentylene and cyclohexylene, preferably cyclohexylene. However, $C_4$–$C_{18}$cycloalkylene likewise stands for structural units such as

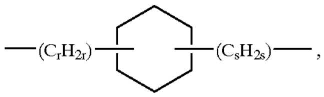

in which r and s independently of one another are 0–12 and the sum r+s is ≦12, or

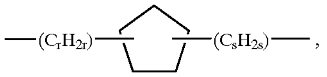

in which r and s independently of one another are 0–13 and the sum r+s is ≦13.

$C_4$–$C_{18}$Cycloalkylene interrupted once or more than once by O, S or $NR_{14}$ stands for cycloalkylene units as described above which can be interrupted either in the ring unit or in the side-chain unit e.g. 1–9 times, 1–7 times or once or twice, by O, S or $NR_{14}$.

$C_3$–$C_{24}$Cycloalkenylene is linear or branched and can be either an individual ring or bridged rings and is mono- or polyunsaturated. It is e.g. $C_3$–$C_{12}$cycloalkenylene or $C_3$–$C_8$cycloalkenylene, for example cyclopentenylene, cyclohexenylene, cyclooctenylene, cyclododecenylene, in particular cyclopentenylene and cyclohexenylene, preferably cyclohexenylene. $C_3$–$C_{24}$Cycloalkenylene also, however, stands for structural units such as

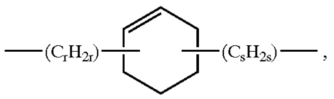

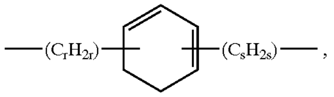

in which r and s independently of another are 0–12 and the sum r+s is ≦12, or

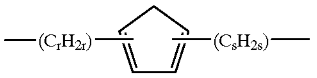

or

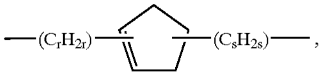

in which r and s independently of one another are 0–13 and the sum r+s is ≦13.

$C_5$–$C_{18}$Cycloalkenylene has the meanings given above for $C_3$–$C_{24}$cycloalkenylene apart from the corresponding number of carbon atoms.

$C_3$–$C_{24}$Cycloalkenylene interrupted once or more than once by O, S or $NR_{14}$ stands for cycloalkenylene units as described above which can be interrupted either in the ring unit or in the side-chain unit e.g. 1–9 times, 1–7 times or once or twice by O, S or $NR_{14}$. Examples are

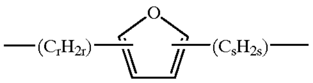

and

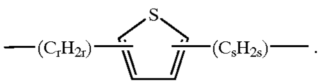

.

Halogen is fluorine, chlorine, bromine or iodine, in particular fluorine, chlorine and bromine, preferably chlorine. $R_1$, $R_1$', $R_2$, $R_2$', $R_3$ and $R_3$' as halogen are, in particular, chlorine.

If in each case two of the radicals $R_1$, $R_2$, $R_3$, $R_4$ or $R_5$ or in each case two of the radicals $R_{19}$, $R_{20}$, $R_{21}$, $R_{22}$ or $R_{23}$ form $C_1$–$C_{12}$alkylene, then, for example, the following structures

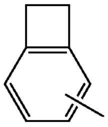

,

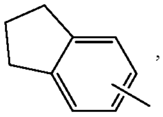

,

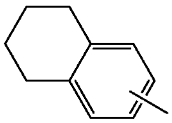

,

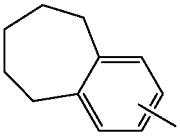

,

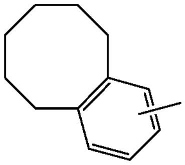

arise.

In connection with the present application, the term "and/or" means that not only one of the defined alternatives (substituents) may be present, but likewise two or more different defined alternatives (substituents) together, i.e. mixtures of different alternatives (substituents). The term "at least" is intended to define one or more than one, e.g. one or two or three, preferably one or two.

As O-, S- or N-containing 5- or 6-membered heterocyclic ring, Ar is e.g. furyl, thienyl, pyrrolyl, oxinyl, dioxinyl or pyridyl. Said heterocyclic radicals can be mono- or polysubstituted, e.g. monosubstituted or disubstituted, by halogen, linear or branched $C_1$–$C_4$alkyl, such as methyl, ethyl, propyl, butyl, and/or $C_1$–$C_4$alkoxy. Examples thereof are dimethylpyridyl, dimethylpyrrolyl or methylfuryl.

Ar is, for example, 2-methylnaphth-2-yl, 2-methoxynaphth-2-yl, 1,3-dimethyinaphth-2-yl, 2,8-dimethylnaphth-1-yl, 1,3-dimethoxynaphth-2-yl, 1,3-dichloronaphth-2-yl, 2,8-dimethoxynaphth-1-yl, 2,4,6-trimethylpyrid-3-yl, 2,4-dimethoxyfuran-3-yl or 2,4,5-trimethylthien-3-yl.

Preference is given to compounds of the formula I in which Ar is a radical

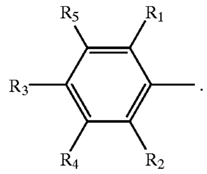

.

Of particular interest are compounds of the formula I, in which $R_1$ and $R_2$ independently of one another are $C_1$–$C_4$alkyl, $C_1$–$C_4$alkoxy, $C_1$ or $CF_3$, in particular methyl or methoxy.

$R_1$ and $R_2$ are preferably identical.

$R_1$ and $R_2$ are preferably $C_1$–$C_4$alkyl or $C_1$–$C_4$alkoxy.

$R_3$, $R_4$ and $R_5$ in the compounds of the formula I are, in particular, independently of one another hydrogen, $C_1$–$C_4$alkyl, $C_1$ or $C_1$–$C_4$alkoxy, in particular hydrogen, methyl or methoxy. $R_3$ is preferably $C_1$–$C_4$alkyl or $C_1$–$C_4$alkoxy, in particular methyl, methoxy or hydrogen, and $R_4$ and $R_5$ are hydrogen.

$R_6$ in the compounds of the formula I is in particular $C_1$–$C_{24}$alkyl, unsubstituted or substituted by cycloalkenyl, CN, $C(O)R_{11}$, $C(O)OR_{11}$, $C(O)N(R_{14})_2$, cycloalkyl, halogen; $C_2$–$C_{24}$alkyl which is interrupted once or more than once by nonconsecutive O, S or $NR_{14}$ and which is unsubstituted or substituted by $OR_{11}$, $SR_{11}$, $N(R_{12})(R_{13})$, CN, $C(O)R_{11}$, $C(O)OR_{11}$, phenyl and/or $C(O)N(R_{14})_2$; $C_2$–$C_{24}$alkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$; benzyl, cyclopentyl, cyclohexyl, $C_4$–$C_{24}$cycloalkyl which is uninterrupted or interrupted once or more than once by O, S and/or $NR_{14}$; or $C_8$–$C_{24}$arylcycloalkyl.

Compounds of the formula I in which $R_{12}$ and $R_{13}$ are e.g. hydrogen, $C_1$–$C_4$alkyl, phenyl or benzyl or $C_2$–$C_{12}$alkyl which is interrupted once or more than once by nonconsecutive O atoms and which is unsubstituted or is substituted by OH and/or SH; or $R_{12}$ and $R_{13}$ together are piperidino, morpholino, or piperazino are likewise of interest. $R_{12}$ and $R_{13}$ are preferably $C_1$–$C_4$alkyl, or $R_{12}$ and $R_{13}$ are together morpholino.

$R_{14}$ in the compounds of the formula I is, in particular, hydrogen, phenyl, $C_1$–$C_4$alkyl or $C_2$–$C_4$alkyl which is interrupted once or more than once by O or S and which is unsubstituted or substituted by OH and/or SH, preferably hydrogen and $C_1$–$C_4$alkyl.

M in the compounds of the formula I is preferably hydrogen or Li, in particular Li.

Of particular interest are compounds of the formula I in which $R_1$ and $R_2$ independently of one another are $C_1$–$C_{12}$alkyl, $OR_{11}$, $CF_3$ or halogen;

$R_3$, $R_4$ and $R_5$ independently of one another are hydrogen, $C_1$–$C_{12}$alkyl, $OR_1$, or halogen;

$R_6$ is $C_1$–$C_{12}$alkyl, unsubstituted or substituted by cycloalkenyl, CN, $C(O)R_{11}$, $C(O)OR_{11}$, phenyl, $C(O)N(R_{14})_2$, cycloalkyl; $C_2$–$C_{12}$alkyl which is interrupted once or more than once by nonconsecutive O, S or $NR_{14}$ and which is unsubstituted or substituted by $OR_{11}$, $SR_{11}$, $N(R_{12})(R_{13})$, CN, $C(O)R_{11}$, $C(O)OR_{11}$ and/or $C(O)N(R_{14})_2$; $C_2$–$C_{12}$alkenyl which is uninterrupted or interrupted once or more than once by nonconsecutive O, S or $NR_{14}$ and which is unsubstituted or substituted by $OR_{11}$, $SR_{11}$, or $N(R_{12})(R_{13})$; benzyl, cyclopentyl, cyclohexyl, $C_4$–$C_{12}$cycloalkyl which is uninterrupted or interrupted once or more than once by O, S and/or $NR_{14}$; or $C_8$–$C_{12}$arylcycloalkyl;

$R_{11}$ is H, $C_1$–$C_{12}$alkyl, cyclohexyl, cyclopentyl, phenyl or benzyl;

$R_{12}$ and $R_{13}$ independently of one another are $C_1$–$C_{12}$alkyl, cyclopentyl, cyclohexyl, phenyl, benzyl or $C_2$–$C_{12}$alkyl which is interrupted once or more than once by nonconsecutive O atoms and which is unsubstituted or substituted by OH and/or SH; or $R_{12}$ and $R_{13}$ together are piperidino, morpholino or piperazino;

$R_{14}$ is hydrogen or $C_1$–$C_{12}$alkyl; and

M is hydrogen or Li.

Of specific interest are compounds of the formula I in which $R_1$ and $R_2$ independently of one another are $C_1$–$C_4$alkyl or $OR_{11}$;

$R_3$, $R_4$ and $R_5$ independently of one another are hydrogen, $C_1$–$C_4$alkyl or $OR_{11}$;

$R_6$ is $C_1$–$C_{12}$alkyl, unsubstituted or substituted by CN, $C(O)R_{11}$, $C(O)OR_{11}$, $C(O)N(R_{14})_2$;

$C_2$–$C_{12}$alkyl which is interrupted once or more than once by nonconsecutive O and which is unsubstituted or substituted by $OR_{11}$, $SR_{11}$, $N(R_{12})(R_{13})$, CN, $C(O)R_{11}$, $C(O)OR_{11}$, phenyl or $C(O)N(R_{14})_2$; $C_2$–$C_8$alkenyl which is uninterrupted or interrupted once or more than once by nonconsecutive O and which is unsubstituted or substituted by $OR_{11}$; benzyl, cyclopentyl, cyclohexyl, $C_4$–$C_8$cycloalkyl which is uninterrupted or interrupted by O, S or $NR_{14}$; or $C_8$–$C_{12}$arylcycloalkyl;

$R_{11}$ is H or $C_1$–$C_{12}$alkyl;

$R_{14}$ is hydrogen or $C_1$–$C_8$alkyl; and

M is Li.

Examples of compounds of the formula I are lithium (2,6-dimethylbenzoyl)ethylphosphine, lithium (2,6-diethylbenzoyl)ethylphosphine, lithium (2,4,6-trimethylbenzoyl)ethylphosphine, lithium (2,3,4,5,6-pentamethylbenzoyl)ethylphosphine, lithium (2,3,5,6-tetramethylbenzoyl)ethylphosphine, lithium (2,4,6-triisopropylbenzoyl)ethylphosphine, lithium (2,4,5,6-tetramethylbenzoyl)ethylphosphine, lithium (2,4,6-tri-tert-butylbenzoyl)ethylphosphine, lithium (2,6-dimethyl-4-tert-butylbenzoyl)ethylphosphine, lithium (2,6-diphenoxymethylbenzoyl)ethylphosphine, lithium (2,3,6-trimethylbenzoyl)ethylphosphine, lithium (2,3,4,6-tetramethylbenzoyl)ethylphosphine, lithium (2-phenyl-6-methylbenzoyl)ethylphosphine, lithium (2,4,6-trimethoxybenzoyl)ethylphosphine, lithium (2,4-dimethoxybenzoyl)ethylphosphine, lithium (2,3,6-trimethoxybenzoyl)ethylphosphine, lithium (2,6-diethoxybenzoyl)ethylphosphine, lithium (2,6-dimethoxy-3,5-dimethylbenzoyl)ethylphosphine, lithium (2,6-dimethoxy-4-methylbenzoyl)ethylphosphine, lithium (2,6-dimethoxy-3-bromobenzoyl)ethylphosphine, lithium (2,6-dimethoxy-3-chlorobenzoyl)ethylphosphine, lithium (2,6-dimethoxy-3-chloro-5-bromobenzoyl)ethylphosphine, lithium (2,6-dimethoxy-3,5-dichlorobenzoyl)ethylphosphine, lithium (2,3,6-trimethoxy-5-bromobenzoyl)ethylphosphine, lithium (2,6-dichlorobenzoyl)ethylphosphine, lithium (2,4,6-trichlorobenzoyl)ethylphosphine, lithium (2,3,6-trichlorobenzoyl)ethylphosphine, lithium (2,3,5,6-tetrachlorobenzoyl)ethy1-phosphine, lithium (2,3,4,5,6-pentachlorobenzoyl)ethylphosphine, lithium (2,6-dichloro-3-methylbenzoyl)ethylphosphine, lithium (2-chloro-6-methylbenzoyl)ethylphosphine, lithium (2-methoxy-3,6-dichlorobenzoyl)ethylphosphine, lithium (2-methoxy-6-chlorobenzoyl)ethylphosphine, lithium (2,6-bis(trifluoromethyl)benzoyl)ethylphosphine, lithium (2-chloro-6-methylthiobenzoyl)ethylphosphine, lithium (2,6-dibromobenzoyl)ethylphosphine, lithium (2,6-dimethylbenzoyl)-n-butylphosphine, lithium (2,6-diethylbenzoyl)-n-butylphosphine, lithium (2,4,6-trimethylbenzoyl)-n-butylphosphine, lithium (2,3,4,5,6-pentamethylbenzoyl)-n-butylphosphine, lithium (2,3,5,6-tetramethylbenzoyl)-n-butylphosphine, lithium (2,4,6-triisopropylbenzoyl)-n-butylphosphine, lithium (2,4,5,6-tetramethylbenzoyl)-n-butylphosphine, lithium (2,4,6-tri-tertbutylbenzoyl)-n-butylphosphine, lithium (2,6-dimethyl-4-tert-butylbenzoyl)-n-butylphosphine, lithium (2,6-diphenoxymethylbenzoyl)-n-butylphosphine, lithium (2,3,6-trimethylbenzoyl)-n-butylphosphine, lithium (2,3,4,6-tetramethylbenzoyl)-n-butylphosphine, lithium (2-phenyl-6-methylbenzoyl)-n-butylphosphine, lithium (2,4,6-trimethoxybenzoyl)-n-butylphosphine, lithium (2,4-dimethoxybenzoyl)-n-butylphosphine, lithium (2,3,6-trimethoxybenzoyl)-n-butylphosphine, lithium (2,6-diethoxybenzoyl)-n-butylphosphine, lithium (2,6-dimethoxy-3,5-dimethylbenzoyl)-n-butylphosphine, lithium (2,6-dimethoxy-4-methylbenzoyl)-n-butylphosphine, lithium (2,6-dimethoxy-3-bromobenzoyl)-n-butylphosphine, lithium (2,6-dimethoxy-3-chlorobenzoyl)-n-butylphosphine, lithium (2,6-dimethoxy-3-chloro-5-bromobenzoyl)-n-butylphosphine, lithium (2,6-dimethoxy-3,5-dichlorobenzoyl)-n-butylphosphine, lithium (2,3,6-trimethoxy-5-bromobenzoyl)-n-butylphosphine, lithium (2,6-dichlorobenzoyl)-n-butylphosphine, lithium (2,4,6-trichlorobenzoyl)-n-butylphosphine, lithium (2,3,6-trichlorobenzoyl)-n-butylphosphine, lithium (2,3,5,6-tetrachlorobenzoyl)-n-butylphosphine, lithium (2,3,4,5,6-pentachlorobenzoyl)-n-butylphosphine, lithium (2,6-dichloro-3-methylbenzoyl)-n-butylphosphine, lithium (2-chloro-6-methylbenzoyl)-n-butylphosphine, lithium (2-methoxy-3,6-dichlorobenzoyl)-n-butylphosphine, lithium (2-methoxy-6-chlorobenzoyl)-n-butylphosphine, lithium (2,6-bis(trifluoromethyl)benzoyl)-n-butylphosphine, lithium (2-chloro-6-methylthiobenzoyl)-n-butylphosphine, lithium (2,6-dibromobenzoyl)-n-butylphosphine, lithium (2,6-dimethylbenzoyl)isobutylphosphine, lithium (2,6-diethylbenzoyl)isobutylphosphine, lithium (2,4,6-trimethylbenzoyl)isobutylphosphine, lithium (2,3,4,5,6-pentamethylbenzoyl)isobutylphosphine, lithium (2,3,5,6-tetramethylbenzoyl)isobutylphosphine, lithium (2,4,6-triisopropylbenzoyl)isobutylphosphine, lithium (2,4,5,6-tetramethylbenzoyl)isobutylphosphine, lithium (2,4,6-tri-tertbutylbenzoyl)isobutylphosphine, lithium (2,6-dimethyl-4-tert-butylbenzoyl)isobutylphosphine, lithium (2,6-diphenoxymethylbenzoyl)isobutylphosphine, lithium (2,3,6-trimethylbenzoyl)isobutylphosphine, lithium (2,3,4,6-tetramethylbenzoyl)isobutylphosphine, lithium (2-phenyl-6-methylbenzoyl)isobutylphosphine, lithium (2,4,6-trimethoxybenzoyl)isobutylphosphine, lithium (2,4-dimethoxybenzoyl)isobutylphosphine, lithium (2,3,6-trimethoxybenzoyl)isobutylphosphine, lithium (2,6-diethoxybenzoyl)isobutylphosphine, lithium (2,6-dimethoxy-3,5-dimethylbenzoyl)isobutylphosphine, lithium (2,6-dimethoxy-4-methylbenzoyl)isobutylphosphine, lithium (2,6-dimethoxy-3-bromobenzoyl)isobutylphosphine, lithium (2,6-dimethoxy-3-chlorobenzoyl)isobutylphosphine, lithium (2,6-dimethoxy-3-chloro-5-bromobenzoyl)isobutylphosphine, lithium (2,6-dimethoxy-3,5-dichlorobenzoyl)isobutylphosphine, lithium (2,3,6-trimethoxy-5-bromobenzoyl)isobutylphosphine, lithium (2,6-dichlorobenzoyl)isobutylphosphine, lithium (2,4,6-trichlorobenzoyl)isobutylphosphine, lithium (2,3,6-trichlorobenzoyl)isobutylphosphine, lithium (2,3,5,6-tetrachlorobenzoyl)isobutylphosphine, lithium (2,3,4,5,6-pentachlorobenzoyl)isobutylphosphine, lithium (2,6- dichloro-3-methylbenzoyl)isobutylphosphine, lithium (2-chloro-6-methylbenzoyl)isobutylphosphine, lithium (2-methoxy-3,6-dichlorobenzoyl)isobutylphosphine, lithium (2-methoxy-6-chlorobenzoyl)isobutylphosphine, lithium (2,6-bis(trifluoromethyl)-benzoyl) isobutylphosphine, lithium (2-chloro-6-methylthiobenzoyl) isobutylphosphine, lithium (2,6-dibromobenzoyl) isobutylphosphine, lithium (2,6-dimethylbenzoyl)-o-methylpropylphosphine, lithium (2,6-diethylbenzoyl)-1-methylpropylphosphine, lithium (2,4,6-trimethylbenzoyl)-1-methylpropylphosphine, lithium (2,3,4,5,6-pentamethylbenzoyl)-1-methylpropylphosphine, lithium (2,3,5,6-tetramethylbenzoyl)-1-methylpropylphosphine, lithium (2,4,6-triisopropylbenzoyl)-1-methylpropylphosphine, lithium (2,4,5,6-tetramethylbenzoyl)-1-methylpropylphosphine, lithium (2,4,6-tri-tert-butylbenzoyl)-1-methylpropylphosphine, lithium (2,6-dimethyl-4-tert-butylbenzoyl)-1-methylpropylphosphine, lithium (2,6-diphenoxymethylbenzoyl)-1-methylpropylphosphine, lithium (2,3,6-trimethylbenzoyl)-1-methylpropylphosphine, lithium (2,3,4,6-tetramethylbenzoyl)-1-methylpropylphosphine, lithium (2-phenyl-6-methylbenzoyl)-1-methylpropylphosphine, lithium (2,4,6-trimethoxybenzoyl)-1-methylpropylphosphine, lithium (2,4-dimethoxybenzoyl)-1-methylpropylphosphine, lithium (2,3,6-trimethoxybenzoyl)-1-methylpropylphosphine, lithium (2,6-diethoxybenzoyl)-1-methylpropylphosphine, lithium (2,6-dimethoxy-3,5-dimethylbenzoyl)-1-methylpropylphosphine, lithium (2,6-dimethoxy-4-methylbenzoyl)-1-methylpropylphosphine, lithium (2,6-dimethoxy-3-bromobenzoyl)-1-methylpropylphosphine, lithium (2,6-dimethoxy-3-chlorobenzoyl)-1-methylpropylphosphine, lithium (2,6-dimethoxy-3-chloro-5-bromobenzoyl)-1-methylpropylphosphine, lithium (2,6-dimethoxy-3,5-dichlorobenzoyl)-1-methylpropylphosphine, lithium (2,3,6-trimethoxy-5-bromobenzoyl)-1-methylpropylphosphine, lithium (2,6-dichlorobenzoyl)-1-methylpropylphosphine, lithium (2,4,6-trichlorobenzoyl)-1-methylpropylphosphine, lithium (2,3,6-trichlorobenzoyl)-1-methylpropylphosphine, lithium (2,3,5,6-tetrachlorobenzoyl)-1-methylpropylphosphine, lithium (2,3,4,5,6-pentachlorobenzoyl)-1-methylpropylphosphine, lithium (2,6-dichloro-3-methylbenzoyl)-1-methylpropylphosphine, lithium (2-chloro-6-methylbenzoyl)-1-methylpropylphosphine, lithium (2-methoxy-3,6-dichlorobenzoyl)-1-methylpropylphosphine, lithium (2-methoxy-6-chlorobenzoyl)-1-methylpropylphosphine, lithium (2,6-bis-(trifluoromethyl)benzoyl)-1-methylpropylphosphine, lithium (2-chloro-6-methylthiobenzoyl)-1-methylpropylphosphine, lithium (2,6-dibromobenzoyl)-1-methylpropylphosphine, lithium (2,6-dimethylbenzoyl)-2,4,4-trimethylpentylphosphine, lithium (2,6-diethylbenzoyl)-2,4,4-trimethylpentylphosphine, lithium (2,4,6-trimethylbenzoyl)-2,4,4-trimethylpentylphosphine, lithium (2,3,4,5,6-pentamethylbenzoyl)-2,4,4-trimethylpentylphosphine, lithium (2,3,5,6-tetramethylbenzoyl)-2,4,4-trimethylpentylphosphine, lithium (2,4,6-triisopropylbenzoyl)-2,4,4-trimethylpentylphosphine, lithium (2,4,5,6-tetramethylbenzoyl)-2,4,4-trimethylpentylphosphine, lithium (2,4,6-tri-tert-butylbenzoyl)-2,4,4-trimethylpentylphosphine, lithium (2,6-dimethyl-4-tertbutylbenzoyl)-2,4,4-trimethylpentylphosphine, lithium (2,6-diphenoxymethylbenzoyl)-2,4,4-trimethylpentylphosphine, lithium (2,3,6-trimethylbenzoyl)-2,4,4-trimethylpentylphosphine, lithium (2,3,4,6-tetramethylbenzoyl)-2,4,4-trimethylpentylphosphine, lithium (2-phenyl-6-methylbenzoyl)-2,4,4-trimethylpentylphosphine, lithium (2,4,6-trimethoxybenzoyl)-2,4,4-trimethylpentylphosphine, lithium (2,4-dimethoxybenzoyl)-2,4,4-trimethylpentylphosphine, lithium (2,3,6-trimethoxybenzoyl)-2,4,4-trimethylpentylphosphine, lithium (2,6-diethoxybenzoyl)-2,4,4-trimethylpentylphosphine, lithium (2,6-dimethoxy-3,5-dimethylbenzoyl)-2,4,4-trimethylpentylphosphine, lithium (2,6-dimethoxy-4-methylbenzoyl)-2,4,4-trimethylpentylphosphine, lithium (2,6-dimethoxy-3-bromobenzoyl)-2,4,4-trimethylpentylphosphine, lithium (2,6-dimethoxy-3-chlorobenzoyl)-2,4,4-trimethylpentylphosphine, lithium (2,6-dimethoxy-3-chloro-5-bromobenzoyl)-2,4,4-trimethylpentylphosphine, lithium (2,6-dimethoxy-3,5-dichlorobenzoyl)-2,4,4-trimethylpentylphosphine, lithium (2,3,6-trimethoxy-5-bromobenzoyl)-2,4,4-trimethylpentylphosphine, lithium (2,6-dichlorobenzoyl)-2,4,4-trimethylpentylphosphine, lithium (2,4,6-trichlorobenzoyl)-2,4,4-trimethylpentylphosphine, lithium (2,3,6-trichlorobenzoyl)-2,4,4-trimethylpentylphosphine, lithium (2,3,5,6-tetrachlorobenzoyl)-2,4,4-trimethylpentylphosphine, lithium (2,3,4,5,6-pentachlorobenzoyl)-2,4,4-trimethylpentylphosphine, lithium (2,6-dichloro-3-methylbenzoyl)-2,4,4-trimethylpentylphosphine, lithium (2-chloro-6-methylbenzoyl)-2,4,4-trimethylpentylphosphine, lithium (2-methoxy-3,6-dichlorobenzoyl)-2,4,4-trimethylpentylphosphine, lithium (2-methoxy-6-chlorobenzoyl)-2,4,4-trimethylpentylphosphine, lithium (2,6-bis(trifluoromethyl) benzoyl)-2,4,4-trimethylpentylphosphine, lithium (2-chloro-6-methylthiobenzoyl)-2,4,4-trimethylpentylphosphine, lithium (2,6-dibromobenzoyl)-2,4,4-trimethylpentylphosphine, lithium (2,6-dimethylbenzoyl)cyclopentylphosphine, lithium (2,6-diethylbenzoyl)cyclopentylphosphine, lithium (2,4,6-trimethylbenzoyl)cyclopentylphosphine, lithium (2,3,4,5,6-pentamethylbenzoyl)cyclopentylphosphine, lithium (2,3,5,6-tetramethylbenzoyl)cyclopentylphosphine, lithium (2,4,6-trisopropylbenzoyl)cyclopentylphosphine, lithium (2,4,5,6-tetramethylbenzoyl)cyclopentylphosphine, lithium (2,4,6-tri-tert-butylbenzoyl)cyclopentylphosphine, lithium (2,6-dimethyl-4-tert-butylbenzoyl)cyclopentylphosphine, lithium (2,6-diphenoxymethylbenzoyl) cyclopentylphosphine, lithium (2,3,6-trimethylbenzoyl) cyclopentylphosphine, lithium (2,3,4,6-tetramethylbenzoyl) cyclopentylphosphine, lithium (2-phenyl-6-methylbenzoyl) cyclopentylphosphine, lithium (2,4,6-trimethoxybenzoyl) cyclopentylphosphine, lithium (2,4-dimethoxybenzoyl) cyclopentylphosphine, lithium (2,3,6-trimethoxybenzoyl) cyclopentylphosphine, lithium (2,6-diethoxybenzoyl) cyclopentylphosphine, lithium (2,6-dimethoxy-3,5-dimethylbenzoyl)cyclopentylphosphine, lithium (2,6-dimethoxy-4-methylbenzoyl)cyclopentylphosphine, lithium (2,6-dimethoxy-3-bromobenzoyl)cyclopentylphosphine, lithium (2,6-dimethoxy-3-chlorobenzoyl) cyclopentylphosphine, lithium (2,6-dimethoxy-3-chloro-5-bromobenzoyl)cyclopentylphosphine, lithium (2,6-dimethoxy-3,5-dichlorobenzoyl)cyclopentylphosphine, lithium (2,3,6-trimethoxy-5-bromobenzoyl) cyclopentylphosphine, lithium (2,6-dichlorobenzoyl) cyclopentylphosphine, lithium (2,4,6-trichlorobenzoyl) cyclopentylphosphine, lithium (2,3,6-trichlorobenzoyl) cyclopentylphosphine, lithium (2,3,5,6-tetrachlorobenzoyl)

cyclopentylphosphine, lithium (2,3,4,5,6-pentachlorobenzoyl)cyclopentylphosphine, lithium (2,6-dichloro-3-methylbenzoyl)cyclopentylphosphine, lithium (2-chloro-6-methylbenzoyl)cyclopentylphosphine, lithium (2-methoxy-3,6-dichlorobenzoyl)cyclopentylphosphine, lithium (2-methoxy-6-chlorobenzoyl)-cyclopentylphosphine, lithium (2,6-bis(trifluoromethyl) benzoyl)cyclopentylphosphine, lithium (2-chloro-6-methylthiobenzoyl)cyclopentylphosphine, lithium (2,6-dibromobenzoyl)cyclopentylphosphine, lithium (2,6-dimethylbenzoyl)cyclohexylphosphine, lithium (2,6-diethylbenzoyl)cyclohexylphosphine, lithium (2,4,6-trimethylbenzoyl)cyclohexylphosphine, lithium (2,3,4,5,6-pentamethylbenzoyl)cyclohexylphosphine, lithium (2,3,5,6-tetramethylbenzoyl)cyclohexylphosphine, lithium (2,4,6-triisopropylbenzoyl)cyclohexylphosphine, lithium (2,4,5,6-tetramethylbenzoyl)cyclohexylphosphine, lithium (2,4,6-tri-tert-butylbenzoyl)cyclohexylphosphine, lithium (2,6-dimethyl-4-tert-butylbenzoyl)cyclohexylphosphine, lithium (2,6-diphenoxymethylbenzoyl)cyclohexylphosphine, lithium (2,3,6-trimethylbenzoyl)cyclohexylphosphine, lithium (2,3,4,6-tetramethylbenzoyl)cyclohexylphosphine, lithium (2-phenyl-6-methylbenzoyl)cyclohexylphosphine, lithium (2,4,6-trimethoxybenzoyl)cyclohexylphosphine, lithium (2,4-dimethoxybenzoyl)cyclohexylphosphine, lithium (2,3,6-trimethoxybenzoyl)cyclohexylphosphine, lithium (2,6-diethoxybenzoyl)cyclohexylphosphine, lithium (2,6-dimethoxy-3,5-dimethylbenzoyl)cyclohexylphosphine, lithium (2,6-dimethoxy-4-methylbenzoyl) cyclohexylphosphine, lithium (2,6-dimethoxy-3-bromobenzoyl)cyclohexylphosphine, lithium (2,6-dimethoxy-3-chlorobenzoyl)cyclohexylphosphine, lithium (2,6-dimethoxy-3-chloro-5-bromobenzoyl) cyclohexylphosphine, lithium (2,6-dimethoxy-3,5-dichlorobenzoyl)cyclohexylphosphine, lithium (2,3,6-trimethoxy-5-bromobenzoyl)cyclohexylphosphine, lithium (2,6-dichlorobenzoyl)cyclohexylphosphine, lithium (2,4,6-trichlorobenzoyl)cyclohexylphosphine, lithium (2,3,6-trichlorobenzoyl)cyclohexylphosphine, lithium (2,3,5,6-tetrachlorobenzoyl)cyclohexylphosphine, lithium (2,3,4,5,6-pentachlorobenzoyl)cyclohexylphosphine, lithium (2,6-dichloro-3-methylbenzoyl)cyclohexylphosphine, lithium (2-chloro-6-methylbenzoyl)cyclohexylphosphine, lithium (2-methoxy-3,6-dichlorobenzoyl)cyclohexylphosphine, lithium (2-methoxy-6-chlorobenzoyl)cyclohexylphosphine, lithium (2,6-bis(trifluoromethyl)benzoyl) cyclohexylphosphine, lithium (2-chloro-6-methylthiobenzoyl)cyclohexylphosphine, lithium (2,6-dibromobenzoyl)cyclohexylphosphine.

The compounds of the formula (I') are, for example, selectively obtained by reaction of acyl halides (IV) with dimetalated organophosphines (V):

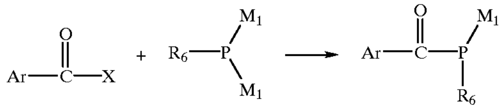

(IV) (V) (I')

Ar and $R_6$ have the meanings described above. X is Cl or Br and $M_1$ is Na, Li or K.

The starting materials are advantageously reacted in the molar ratio 1:1. A slight excess of one or other of the components, e.g. up to 20%, is not, however, critical. In this case too the desired product is formed, although the proportion of undesired byproduct may be influenced.

The reaction is advantageously carried out in a solvent. In particular, as solvents, it is possible to use ethers which are liquid at atmospheric pressure and room temperature. Examples are dimethyl ether, diethyl ether, methyl propyl ether, 1,2-dimethoxyethane, bis-(2-methoxyethyl) ether, dioxane or tetrahydrofuran. Preference is given to using tetrahydrofuran.

The reaction temperatures are advantageously −60° C. to +120° C., e.g. −40° C. to 100° C., for example −20° C. to +80° C.

It is advisable to stir the reaction mixture.

It is advantageous to initially introduce the compound of the formula V and to add dropwise the compound of the formula IV at the temperatures given above. Here, the compound of the formula IV can be added without a diluent or else diluted with the reaction solvent. If desired, the course of the reaction can be monitored using methods customary in the art, for example NMR, for example $^{31}$P-NMR, chromatography (thin-layer, HPLC, GC) etc.

In the reactions described above, it is essential to work in an inert gas atmosphere, e.g. with a protective gas such as argon or nitrogen, in order to exclude atmospheric oxygen.

In order to prepare compounds of the formula I in which M is hydrogen, the reaction given above is followed by a hydrolysis step:

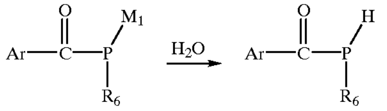

(I') (I)

The procedure for such hydrolysis reactions is known to the person skilled in the art and is carried out under generally customary conditions. The hydrolysis of metalated primary and secondary phosphines is described, for example, in Houben-Weyl, XII/1, pages 56–57. Likewise conceivable is the preparation of compounds of the formula (I) where M=hydrogen, by reaction between a compound of the formula (IV) and an alkylphosphine compound in the presence of an acid-binding agent, such as barium carbonate, calcium carbonate or potassium carbonate, as described, for example, in Houben-Weyl, XII/1, pages 73–74 or in K. Issleib and R. Kümmel, Z. Naturf. B (1967), 22, 784.

The compounds of the formula I according to the invention are identified by $^{31}$P-NMR spectroscopy and are stable in the solution under inert gas at room temperature for a number of weeks.

The invention also provides a process for the selective preparation of compounds of the formula I by (1) reaction of an acyl halide of the formula IV (IV)

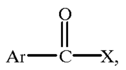

in which

Ar is as defined above, and

X is Cl or Br;

with a dimetalated organophosphine of the formula V (V)

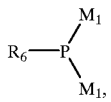

in which $R_6$ is as defined above; and $M_1$ is Na, Li or K;

in the molar ratio 1:1; and (2) where appropriate, subsequent hydrolysis if compounds of the formula I in which M is hydrogen are to be obtained.

The acyl halides (IV) used as starting material are known substances, some of which are available commercially, or can be prepared analogously to known compounds.

A method for the preparation of metalated alkylphosphines is, for example, the reaction of suitable alkylphosphines with the corresponding alkali metal, alkali metal hydride or an alkyllithium compound.

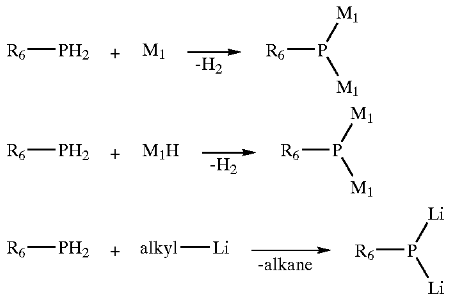

($M_1$ is as defined above)

The reaction is advantageously carried out with the exclusion of air in an inert solvent at temperatures of, for example, −80° C. to +120° C. Advantageously, 2 to 4 mole equivalents of the alkali metals, alkali metal hydrides or alkyllithium compound are used. Suitable solvents are e.g. ethers, as described above, or inert solvents, such as alkanes, cycloalkanes, aromatic solvents such as toluene, xylene, mesitylene.

The preparation of the alkylphosphines $R_6$-$PH_2$ is generally known. For example, the compounds can, for example, be obtained by reacting $PH_3$ with alkenes in the presence of a free-radical former or by reducing alkylphosphine chlorides e.g. with lithium aluminium hydride. These and other methods are, for example, described in "Organic Phosphorous Compounds, Vol. 1–7, Wiley-Interscience 1972, Editors R. M. Kosalapoff and L. Maier".

The compounds of the formula I are particularly suitable for the preparation of unsymmetrical mono- and bisacylphosphines, mono- and bisacylphosphine oxides, and mono- and bisacylphosphine sulfides. "Unsymmetrical" means in this connection that in the bisacylphosphines, bisacylphosphine oxides and sulfides, two different acyl groups are present, and in the monoacylphosphines, monoacylphosphine oxides and sulfides, in addition to the acyl group, two different radicals are bonded to the phosphorus atom.

Such "unsymmetrical" mono- and bisacylphosphines, mono- and bisacylphosphine oxides, and mono- and bisacylphosphine sulfides are, with a few exceptions, novel.

Accordingly, the invention also provides compounds of the formula II (II)

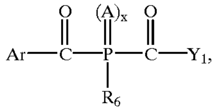

wherein

A is O or S;

x is 0 or 1;

Ar is a group

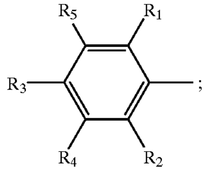

or Ar is cyclopentyl, cyclohexyl, naphthyl, anthracyl, biphenylyl or an O-, S- or N-containing 5- or 6-membered heterocyclic ring, where the radicals cyclopentyl, cyclohexyl, naphthyl, anthracyl, biphenylyl and 5- or 6-membered heterocyclic ring are unsubstituted or substituted by halogen, $C_1$–$C_4$alkyl and/or $C_1$–$C_4$alkoxy;

$R_1$ and $R_2$ independently of one another are $C_1$–$C_{20}$alkyl, $OR_{11}$, $CF_3$ or halogen;

$R_3$, $R_4$ and $R_5$ independently of one another are hydrogen, $C_1$–$C_{20}$alkyl, $OR_{11}$ or halogen;

or in each case two of the radicals $R_1$, $R_2$, $R_3$, $R_4$ and $R_5$ together form $C_1$–$C_{20}$alkylene which can be interrupted by O, S or $NR_{14}$;

$R_6$ is $C_1$–$C_{24}$alkyl, unsubstituted or substituted by $C_5$–$C_{24}$cycloalkenyl, phenyl, CN, $C(O)R_{11}$, $C(O)OR_{11}$, $C(O)N(R_{14})_2$, $OC(O)R_{11}$, $OC(O)OR_{11}$, $N(R_{14})C(O)N(R_{14})$, $OC(O)NR_{14}$, $N(R_{14})C(O)OR_{11}$, cycloalkyl, halogen, $OR_{11}$, $SR_{11}$, $N(R_{12})(R_{13})$ or

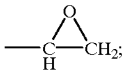

$C_2$–$C_{24}$alkyl which is interrupted once or more than once by nonconsecutive O, S or $NR_{14}$ and which is unsubstituted or substituted by phenyl, $OR_{11}$, $SR_{11}$, $N(R_{12})(R_{13})$, CN, $C(O)R_{11}$, $C(O)OR_{11}$, $C(O)N(R_{14})_2$ and/or

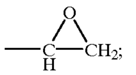

$C_2$–$C_{24}$alkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_5$–$C_{24}$cycloalkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_7$–$C_{24}$arylalkyl which is unsubstituted or substituted on the aryl group by $C_1$–$C_{12}$alkyl, $C_1$–$C_{12}$alkoxy or halogen;

$C_4$–$C_{24}$cycloalkyl which is uninterrupted or interrupted once or more than once by O, S and/or $NR_{14}$ and which is unsubstituted or substituted by $OR_{11}$, $SR_{11}$ or $N(R_{12})(R_{13})$;

or $C_8$–$C_{24}$arylcycloalkyl or C8–$C_{24}$arylcycloalkenyl;

$R_{11}$ is H, $C_1$–$C_{20}$alkyl, $C_2$–$C_{20}$alkenyl, $C_3$–$C_8$cycloalkyl, phenyl, benzyl or $C_2$–$C_{20}$alkyl which is interrupted once or more than once by nonconsecutive O atoms and which is unsubstituted or substituted by OH and/or SH;

$R_{12}$ and $R_{13}$ independently of one another are hydrogen, $C_1$–$C_{20}$alkyl, $C_3$–$C_8$cycloalkyl, phenyl, benzyl or $C_2$–$C_{20}$alkyl which is interrupted once or more than once by O or S and which is unsubstituted or substituted by OH and/or SH; or $R_{12}$ and $R_{13}$ together are $C_3$–$C_5$alkylene which is uninterrupted or interrupted by O, S or $NR_{14}$;

$Y_1$ is $C_1$–$C_{18}$alkyl which is unsubstituted or substituted by one or more phenyl; $C_1$–$C_{18}$-halogenoalkyl; $C_2$–$C_{18}$alkyl which is interrupted once or more than once by O or S and which can be substituted by OH and/or SH; unsubstituted $C_3$–$C_{18}$cycloalkyl or $C_3$–$C_{18}$cycloalkyl substituted by $C_1$–$C_{20}$alkyl, $OR_{11}$, $CF_3$ or halogen; $C_2$–$C_{18}$alkenyl; or $Y_1$ is $OR_{11}$, $N(R_{12})(R_{13})$ or one of the radicals

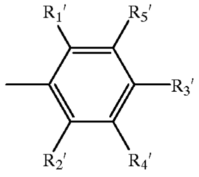

or

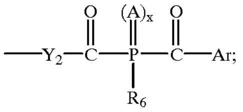

or $Y_1$ is cyclopentyl, cyclohexyl, naphthyl, anthracyl, biphenylyl or an O-, S- or N-containing 5- or 6-membered heterocyclic ring, where the radicals cyclopentyl, cyclohexyl, naphthyl, anthracyl, biphenylyl and 5- or 6-membered heterocyclic ring are unsubstituted or substituted by halogen, $C_1$–$C_4$alkyl and/or $C_1$–$C_4$alkoxy;

$Y_2$ is a direct bond; unsubstituted or phenyl-substituted $C_1$–$C_{18}$alkylene; unsubstituted $C_4$–$C_{18}$-cycloalkylene or $C_4$–$C_{18}$cycloalkylene substituted by $C_1$–$C_{12}$alkyl, $OR_{11}$, halogen and/or phenyl; unsubstituted $C_5$–$C_{18}$cycloalkenylene or $C_5$–$C_{18}$cycloalkenylene substituted by $C_1$–$C_{12}$alkyl, $OR_{11}$, halogen and/or phenyl; unsubstituted phenylene or phenylene substituted one to four times by $C_1$–$C_{12}$alkyl, $OR_{11}$, halogen, —(CO)$OR_{14}$, —(CO)N$(R_{12})(R_{13})$ and/or phenyl;

or $Y_2$ is a radical

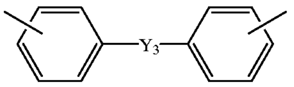

or

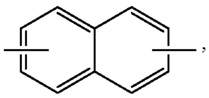

, where these radicals are unsubstituted or are substituted one to four times on one or both aromatic ring(s) by $C_1$–$C_{12}$alkyl, $OR_{11}$, halogen and/or phenyl;

$Y_3$ is O, S, SO, $SO_2$, $CH_2$, $C(CH_3)_2$, $CHCH_3$, $C(CF_3)_2$, (CO), or a direct bond;

$R_{14}$ is hydrogen, phenyl, $C_1$–$C_{12}$alkyl or $C_2$–$C_{12}$alkyl which is interrupted once or more than once by O or S and which can be substituted by OH and/or SH;

$R_1$' and $R_2$' independently of one another have the same meanings as given for $R_1$ and $R_2$; and $R_3$', $R_4$' and $R_5$' independently of one another have the same meanings as given for $R_3$, $R_4$ and $R_5$; or in each case two of the radicals $R_1$', $R_2$', $R_3$', $R_4$' and $R_5$' together form $C_1$–$C_{20}$alkylene which may be interrupted by O, S or —$NR_{14}$;

with the proviso that $Y_1$ is not identical to Ar.

In the compounds of the formula II, the preferred meanings of the radicals $R_1$, $R_2$, $R_3$, $R_4$, $R_5$ and $R_6$ are analogous to those given above for the compounds of the formula I.

In the compounds of the formula II, x is preferably 1. In particular, A is oxygen and Ar is a group

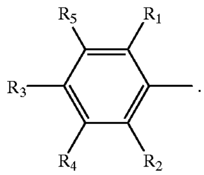

.

Of particular importance are compounds of the formula II in which $Y_1$ is $C_1$–$C_{12}$alkyl, in particular branched $C_1$–$C_{12}$alkyl; unsubstituted $C_3$–$C_{18}$cycloalkyl or $C_3$–$C_{18}$cycloalkyl substituted by $C_1$–$C_{20}$alkyl, $OR_{11}$, $CF_3$ or halogen; or is

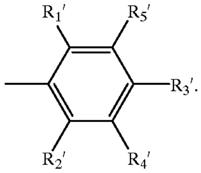

.

$Y_1$ as $C_1$–$C_{12}$alkyl is preferably branched in the a-position relative to the bond to the CO group. The carbon atom in the α-position relative to the CO group is preferably a tertiary carbon atom.

The preferred meanings for $R_1$', $R_2$', $R_3$', $R_4$' and $R_5$' are analogous to those preferred meanings of $R_1$, $R_2$, $R_3$, $R_4$ and $R_5$ given above for formula I.

Also of interest are compounds of the formula II in which $R_1$, $R_2$ and $R_3$ are $C_1$–$C_4$alkyl, in particular methyl; $R_1$' and $R_2$' are $C_1$–$C_4$alkoxy, in particular methoxy, or chlorine; and $R_4$, $R_5$, $R_3$', $R_4$' and $R_5$' are hydrogen.

In preferred compounds of the formula II,

A is oxygen and x is 1;

$R_1$ and $R_2$ are $C_1$–$C_4$alkyl, $C_1$–$C_4$alkoxy, Cl or $CF_3$;

$R_3$ is hydrogen, $C_1$–$C_4$alkyl or $C_1$–$C_4$alkoxy;

$R_4$ and $R_5$ are hydrogen;

$R_6$ is $C_1$–$C_{12}$alkyl, unsubstituted or substituted by cycloalkenyl, CN, C(O)$R_{11}$, C(O)$OR_{11}$, phenyl, C(O)N$(R_{14})_2$, cycloalkyl; $C_2$–$C_{12}$alkyl which is interrupted once or more than once by nonconsecutive O, S or $NR_{14}$ and which is unsubstituted or substituted by $OR_{11}$, $SR_{11}$, $N(R_{12})(R_{13})$, CN, C(O)$R_{11}$, C(O)$OR_{11}$ and/or C(O)N$(R_{14})_2$; $C_2$–$C_{12}$alkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$; benzyl, cyclopentyl, cyclohexyl, $C_4$–$C_{12}$cycloalkyl which is uninterrupted or interrupted once or more than once by O, S and/or $NR_{14}$; or $C_8$–$C_{12}$arylcycloalkyl;

$R_{11}$ is H, $C_1$–$C_{12}$alkyl, cyclohexyl, cyclopentyl, phenyl or benzyl;

$R_{12}$ and $R_{13}$ independently of one another are $C_1$–$C_{12}$alkyl, cyclopentyl, cyclohexyl, phenyl, benzyl or $C_2$–$C_{12}$alkyl which is interrupted once or more than once by nonconsecutive O atoms and which is unsubstituted or substituted by OH and/or SH; or $R_{12}$ and $R_{13}$ together are piperidino, morpholino or piperazino;

$R_{14}$ is hydrogen or $C_1$–$C_{12}$alkyl; and $Y_1$ is $C_1$–$C_{12}$alkyl or

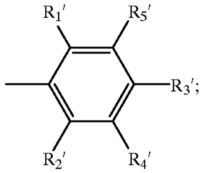

$R_1$' and $R_2$' have the same meanings as given for $R_1$ and $R_2$; and $R_3$', $R_4$' and $R_5$' independently of one another have the same meanings as given for $R_3$, $R_4$ and $R_5$.

Examples of preferred compounds of the formula II are (2,4,6-trimethylbenzoyl)-(2,6-dimethylbenzoyl) ethylphosphine oxide, (2,4,6-trimethylbenzoyl)-(2,6-diethylbenzoyl)ethylphosphine oxide, (2,4,6-trimethylbenzoyl)-(2,6-dimethyl-4-tert-butylbenzoyl) ethylphosphine oxide, (2,4,6-trimethylbenzoyl)-(2,4,6-trimethoxybenzoyl)ethylphosphine oxide, (2,4,6-trimethylbenzoyl)-(2,4-dimethoxybenzoyl)ethylphosphine oxide, (2,4,6-trimethylbenzoyl)-(2,6-diethoxybenzoyl) ethylphosphine oxide, (2,4,6-trimethylbenzoyl)-(2,6-dimethoxy-4-methylbenzoyl)ethylphosphine oxide, (2,4,6-trimethylbenzoyl)-(2,6-dichlorobenzoyl)ethylphosphine oxide, (2,4,6-trimethylbenzoyl)-(2,4,6-trichlorobenzoyl) ethylphosphine oxide, (2,4,6-trimethylbenzoyl)-{2,6-bis (trifluoromethyl)benzoyl}ethylphosphine oxide, (2,6-dimethoxybenzoyl)-(2,6-dimethylbenzoyl)ethylphosphine oxide, (2,6-dimethoxybenzoyl)-(2,6-diethylbenzoyl) ethylphosphine oxide, (2,6-dimethoxybenzoyl)-(2,4,6-trimethylbenzoyl)ethylphosphine oxide, (2,6-dimethoxybenzoyl)-(2,6-dimethyl-4-tert-butylbenzoyl) ethylphosphine oxide, (2,6-dimethoxybenzoyl)-(2,4,6-trimethoxybenzoyl)ethylphosphine oxide, (2,6-dimethoxybenzoyl)-(2,4-dimethoxybenzoyl)ethylphosphine oxide, (2,6-dimethoxybenzoyl)-(2,6-diethoxybenzoyl) ethylphosphine oxide, (2,6-dimethoxybenzoyl)-(2,6-dimethoxy-4-methylbenzoyl)ethylphosphine oxide, (2,6-dimethoxybenzoyl)-(2,6-dichlorobenzoyl)ethylphosphine oxide, (2,6-dimethoxybenzoyl)-(2,4,6-trichlorobenzoyl) ethylphosphine oxide, (2,6-dimethoxybenzoyl)-{2,6-bis (trifluoromethyl)benzoyl}ethylphosphine oxide, (2,6-dimethylbenzoyl)-(2,6-diethylbenzoyl)ethylphosphine oxide, (2,6-dimethylbenzoyl)-(2,4,6-trimethylbenzoyl) ethylphosphine oxide, (2,6-dimethylbenzoyl)-(2,6-dimethyl-4-tert-butylbenzoyl)ethylphosphine oxide, (2,6-dimethylbenzoyl)-(2,4,6-trimethoxybenzoyl) ethylphosphine oxide, (2,6-dimethylbenzoyl)-(2,4-dimethoxybenzoyl)ethylphosphine oxide, (2,6-dimethylbenzoyl)-(2,6-diethoxybenzoyl)ethylphosphine oxide, (2,6-dimethylbenzoyl)-(2,6-dimethoxy-4-methylbenzoyl)ethylphosphine oxide, (2,6-dimethylbenzoyl)-(2,6-dichlorobenzoyl)ethylphosphine oxide, (2,6-dimethylbenzoyl)-(2,4,6-trichlorobenzoyl) ethylphosphine oxide, (2,6-dimethylbenzoyl)-{2,6-bis (trifluoromethyl)benzoyl}ethylphosphine oxide, (2,4,6-trimethoxybenzoyl)-(2,6-dimethylbenzoyl)ethylphosphine oxide, (2,4,6-trimethoxybenzoyl)-(2,6-diethylbenzoyl) ethylphosphine oxide, (2,4,6-trimethoxybenzoyl)-(2,4,6-trimethylbenzoyl)ethylphosphine oxide, (2,4,6-trimethoxybenzoyl)-(2,6-dimethyl-4-tert-butylbenzoyl) ethylphosphine oxide, (2,4,6-trimethoxybenzoyl)-(2,4-dimethoxybenzoyl)ethylphosphine oxide, (2,4,6-trimethoxybenzoyl)-(2,6-diethoxybenzoyl)ethylphosphine oxide, (2,4,6-trimethoxybenzoyl)-(2,6-dichlorobenzoyl) ethylphosphine oxide, (2,4,6-trimethoxybenzoyl)-{2,6-bis (trifIuoromethyl)benzoyl}ethylphosphine oxide, (2,6-dimethyl-4-tert-butylbenzoyl)-(2,6-dimethylbenzoyl) ethylphosphine oxide, (2,6-dimethyl-4-tert-butylbenzoyl)-(2,6-diethylbenzoyl)ethylphosphine oxide, (2,6-dimethyl-4-tert-butylbenzoyl)-(2,4,6-trimethylbenzoyl)ethylphosphine oxide, (2,6-dimethyl-4-tert-butylbenzoyl)-(2,6-dimethyl-4-tert-butylbenzoyl)ethylphosphine oxide, (2,6-dimethyl-4-tert-butylbenzoyl)-(2,4,6-trimethoxybenzoyl) ethylphosphine oxide, (2,6-dimethyl-4-tert-butylbenzoyl)-(2,4-dimethoxybenzoyl)ethylphosphine oxide, (2,6-dimethyl-4-tert-butylbenzoyl)-(2,6-diethoxybenzoyl) ethylphosphine oxide, (2,6-dimethyl-4-tert-butylbenzoyl)-(2,6-diethoxybenzoyl)ethylphosphine oxide, (2,6-dimethyl-4-tert-butylbenzoyl)-(2,6-dichlorobenzoyl)ethylphosphine oxide, (2,6-dimethyl-4-tert-butylbenzoyl)-(2,4,6-trichlorobenzoyl)ethylphosphine oxide, (2,6-dimethyl-4-tert-butylbenzoyl)-{2,6-bis(trifluoromethyl) benzoyl}ethylphosphine oxide, (2,4,6-trimethylbenzoyl)-(2,6-dimethylbenzoyl)-n-butylphosphine oxide, (2,4,6-trimethylbenzoyl)-(2,6-diethylbenzoyl)-n-butylphosphine oxide, (2,4,6-trimethylbenzoyl)-(2,6-dimethyl-4-tert-butylbenzoyl)-n-butylphosphine oxide, (2,4,6-trimethylbenzoyl)-(2,4,6-trimethoxybenzoyl)-n-butylphosphine oxide, (2,4,6-trimethylbenzoyl)-(2,4-dimethoxybenzoyl)-n-butylphosphine oxide, (2,4,6-trimethylbenzoyl)-(2,6-diethoxybenzoyl)-n-butylphosphine oxide, (2,4,6-trimethylbenzoyl)-(2,6-dimethoxy-4-methylbenzoyl)-n-butylphosphine oxide, (2,4,6-trimethylbenzoyl)-(2,6-dichlorobenzoyl)-n-butylphosphine oxide, (2,4,6-trimethylbenzoyl)-(2,4,6-trichlorobenzoyl)-n-butylphosphine oxide, (2,4,6-trimethylbenzoyl)-{2,6-bis (trifluoromethyl)benzoyl}-n-butylphosphine oxide, (2,6-dimethoxybenzoyl)-(2,6-dimethylbenzoyl)-n-butylphosphine oxide, (2,6-dimethoxybenzoyl)-(2,6-diethylbenzoyl)-n-butylphosphine oxide, (2,6-dimethoxybenzoyl)-(2,4,6-trimethylbenzoyl)-n-butylphosphine oxide, (2,6-dimethoxybenzoyl)-(2,6-dimethyl-4-tert-butylbenzoyl)-n-butylphosphine oxide, (2,6-dimethoxybenzoyl)-(2,4,6-trimethoxybenzoyl)-n-butylphosphine oxide, (2,6-dimethoxybenzoyl)-(2,4-dimethoxybenzoyl)-n-butylphosphine oxide, (2,6-dimethoxybenzoyl)-(2,6-diethoxybenzoyl)-n-butylphosphine oxide, (2,6-dimethoxybenzoyl)-(2,6-dimethoxy-4-methylbenzoyl)-n-butylphosphine oxide, (2,6-dimethoxybenzoyl)-(2,6-dichlorobenzoyl)-n-butylphosphine oxide, (2,6-dimethoxybenzoyl)-(2,4,6-trichlorobenzoyl)-n-butylphosphine oxide, (2,6-dimethoxybenzoyl)-{2,6-bis-(trifluoromethyl)benzoyl}-n-butylphosphine oxide, (2,6-dimethylbenzoyl)-(2,6-diethylbenzoyl)-n-butylphosphine oxide, (2,6-dimethylbenzoyl)-(2,4,6-trimethylbenzoyl)-n-butylphosphine oxide, (2,6-dimethylbenzoyl)-(2,6-dimethyl-4-tert-butylbenzoyl)-n-butylphosphine oxide, (2,6-dimethylbenzoyl)-(2,4,6-trimethoxybenzoyl)-n-butylphosphine oxide, (2,6-dimethylbenzoyl)-(2,4-dimethoxybenzoyl)-n-butylphosphine oxide, (2,6-dimethylbenzoyl)-(2,6-diethoxybenzoyl)-n-butylphosphine oxide, (2,6-dimethylbenzoyl)-(2,6-dimethoxy-4-methylbenzoyl)-n-butylphosphine oxide, (2,6-dimethylbenzoyl)-(2,6-dichlorobenzoyl)-n-butylphosphine oxide, (2,6-dimethylbenzoyl)-(2,4,6-trichlorobenzoyl)-n-butylphosphine oxide, (2,6-dimethylbenzoyl)-{2,6-bis (trifluoromethyl)benzoyl}-n-butylphosphine oxide, (2,4,6-trimethoxybenzoyl)-(2,6-dimethylbenzoyl)-n-butylphosphine oxide, (2,4,6-trimethoxybenzoyl)-(2,6-diethylbenzoyl)-n-butylphosphine oxide, (2,4,6- trimethoxybenzoyl)-(2,4,6-trimethylbenzoyl)-n-butylphosphine oxide, (2,4,6-trimethoxybenzoyl)-(2,6-dimethyl-4-tert-butylbenzoyl)-n-butylphosphine oxide, (2,4,6-trimethoxybenzoyl)-(2,4-dimethoxybenzoyl)-n-butylphosphine oxide, (2,4,6-trimethoxybenzoyl)-(2,6-diethoxybenzoyl)-n-butylphosphine oxide, (2,4,6-trimethoxybenzoyl)-(2,6-dichlorobenzoyl)-n-butylphosphine oxide, (2,4,6-trimethoxybenzoyl)-{2,6-bis(trifluoromethyl)benzoyl}-n-butylphosphine oxide, (2,6-dimethyl-4-tert-butylbenzoyl)-(2,6-dimethylbenzoyl)-n-butylphosphine oxide, (2,6-dimethyl-4-tert-butylbenzoyl)-(2,6-diethylbenzoyl)-n-butylphosphine oxide, (2,6-dimethyl-4-tert-butylbenzoyl)-(2,4,6-trimethylbenzoyl)-n-butylphosphine oxide, (2,6-dimethyl-4-tert-butylbenzoyl)-(2,6-dimethyl-4-tert-butylbenzoyl)-n-butylphosphine oxide, (2,6-dimethyl-4-tert-butylbenzoyl)-(2,4,6-trimethoxybenzoyl)-n-butylphosphine oxide, (2,6-dimethyl-4-tert-butylbenzoyl)-(2,4-dimethoxybenzoyl)-n-butylphosphine oxide, (2,6-dimethyl-4-tert-butylbenzoyl)-(2,6-diethoxybenzoyl)-n-butylphosphine oxide, (2,6-dimethyl-4-tert-butylbenzoyl)-(2,6-dimethoxy-4-methylbenzoyl)-n-butylphosphine oxide, (2,6-dimethyl-4-tert-butylbenzoyl)-(2,6-dichlorobenzoyl)-n-butylphosphine oxide, (2,6-dimethyl-4-tert-butylbenzoyl)-(2,4,6-trichlorobenzoyl)-n-butylphosphine oxide, (2,6-dimethyl-4-tert-butylbenzoyl)-{2,6-bis(trifluoromethyl)benzoyl}-n-butylphosphine oxide, (2,4,6-trimethylbenzoyl)-(2,6-dimethylbenzoyl)isobutylphosphine oxide, (2,4,6-trimethylbenzoyl)-(2,6-diethylbenzoyl)isobutylphosphine oxide, (2,4,6-trimethylbenzoyl)-(2,6-dimethyl-4-tert-butylbenzoyl)isobutylphosphine oxide, (2,4,6-trimethylbenzoyl)-(2,4,6-trimethoxybenzoyl)isobutylphosphine oxide, (2,4,6-trimethylbenzoyl)-(2,4-dimethoxybenzoyl)isobutylphosphine oxide, (2,4,6-trimethylbenzoyl)-(2,6-diethoxybenzoyl)isobutylphosphine oxide, (2,4,6-trimethylbenzoyl)-(2,6-dimethoxy-4-methylbenzoyl)isobutylphosphine oxide, (2,4,6-trimethylbenzoyl)-(2,6-dichlorobenzoyl)isobutylphosphine oxide, (2,4,6-trimethylbenzoyl)-(2,4,6-trichlorobenzoyl)isobutylphosphine oxide, (2,4,6-trimethylbenzoyl)-{2,6-bis(trifluoromethyl)benzoyl}isobutylphosphine oxide, (2,6-dimethoxybenzoyl)-(2,6-dimethylbenzoyl)isobutylphosphine oxide, (2,6-dimethoxybenzoyl)-(2,6-diethylbenzoyl)isobutylphosphine oxide, (2,6-dimethoxybenzoyl)-(2,4,6-trimethylbenzoyl)isobutylphosphine oxide, (2,6-dimethoxybenzoyl)-(2,6-dimethyl-4-tert-butylbenzoyl)isobutylphosphine oxide, (2,6-dimethoxybenzoyl)-(2,4,6-trimethoxybenzoyl)isobutylphosphine oxide, (2,6-dimethoxybenzoyl)-(2,4-dimethoxybenzoyl)isobutylphosphine oxide, (2,6-dimethoxybenzoyl)-(2,6-diethoxybenzoyl)isobutylphosphine oxide, (2,6-dimethoxybenzoyl)-(2,6-dimethoxy-4-methylbenzoyl)isobutylphosphine oxide, (2,6-dimethoxybenzoyl)-(2,6-dichlorobenzoyl)isobutylphosphine oxide, (2,6-dimethoxybenzoyl)-(2,4,6-trichlorobenzoyl)isobutylphosphine oxide, (2,6-dimethoxybenzoyl)-{2,6-bis(trifluoromethyl)benzoyl}isobutylphosphine oxide, (2,6-dimethylbenzoyl)-(2,6-diethylbenzoyl)isobutylphosphine oxide, (2,6-dimethylbenzoyl)-(2,4,6-trimethylbenzoyl)isobutylphosphine oxide, (2,6-dimethylbenzoyl)-(2,6-dimethyl-4-tert-butylbenzoyl)isobutylphosphine oxide, (2,6-dimethylbenzoyl)-(2,4,6-trimethoxybenzoyl)isobutylphosphine oxide, (2,6-dimethylbenzoyl)-(2,4-dimethoxybenzoyl)isobutylphosphine oxide, (2,6-dimethylbenzoyl)-(2,6-diethoxybenzoyl)isobutylphosphine oxide, (2,6-dimethylbenzoyl)-(2,6-dimethoxy-4-methylbenzoyl)isobutylphosphine oxide, (2,6-dimethylbenzoyl)-(2,6-dichlorobenzoyl)isobutylphosphine oxide, (2,6-dimethylbenzoyl)-(2,4,6-trichlorobenzoyl)isobutylphosphine oxide, (2,6-dimethylbenzoyl)-{2,6-bis(trifluoromethyl)benzoyl}isobutylphosphine oxide, (2,4,6-trimethoxybenzoyl)-(2,6-dimethylbenzoyl)isobutylphosphine oxide, (2,4,6-trimethoxybenzoyl)-(2,6-diethylbenzoyl)isobutylphosphine oxide, (2,4,6-trimethoxybenzoyl)-(2,4,6-trimethylbenzoyl)isobutylphosphine oxide, (2,4,6-trimethoxybenzoyl)-(2,6-dimethyl-4-tert-butylbenzoyl)isobutylphosphine oxide, (2,4,6-trimethoxybenzoyl)-(2,4-dimethoxybenzoyl)isobutylphosphine oxide, (2,4,6-trimethoxybenzoyl)-(2,6-diethoxybenzoyl)isobutylphosphine oxide, (2,4,6-trimethoxybenzoyl)-(2,6-dichlorobenzoyl)isobutylphosine oxide, (2,4,6-trimethoxybenzoyl)-{2,6-bis(trifluoromethyl)benzoyl}-isobutylphosphine oxide, (2,6-dimethyl-4-tert-butylbenzoyl)-(2,6-dimethylbenzoyl)isobutylphosphine oxide, (2,6-dimethyl-4-tert-butylbenzoyl)-(2,6-diethylbenzoyl)isobutylphosphine oxide, (2,6-dimethyl-4-tert-butylbenzoyl)-(2,4,6-trimethylbenzoyl)isobutylphosphine oxide, (2,6-dimethyl-4-tert-butylbenzoyl)-(2,6-dimethyl-4-tert-butylbenzoyl)isobutylphosphine oxide, (2,6-dimethyl-4-tert-butylbenzoyl)-(2,4,6-trimethoxybenzoyl)isobutylphosphine oxide, (2,6-dimethyl-4-tert-butylbenzoyl)-(2,4-dimethoxybenzoyl)isobutylphosphine oxide, (2,6-dimethyl-4-tert-butylbenzoyl)-(2,6-diethoxybenzoyl)isobutylphosphine oxide, (2,6-dimethyl-4-tert-butylbenzoyl)-(2,6-dimethoxy-4-methylbenzoyl)isobutylphosphine oxide, (2,6-dimethyl-4-tert-butylbenzoyl)-(2,6-dichlorobenzoyl)isobutylphosphine oxide, (2,6-dimethyl-4-tert-butylbenzoyl)-(2,4,6-trichlorobenzoyl)isobutylphosphine oxide, (2,6-dimethyl-4-tert-butylbenzoyl)-{2,6-bis-(trifluoromethyl)benzoyl}isobutylphosphine oxide, (2,4,6-trimethylbenzoyl)-(2,6-dimethylbenzoyl)-(1-methylpropyl)phosphine oxide, (2,4,6-trimethylbenzoyl)-(2,6-diethylbenzoyl)-(1-methylpropyl)phosphine oxide, (2,4,6-trimethylbenzoyl)-(2,6-dimethyl-4-tert-butylbenzoyl)-(1-methylpropyl)phosphine oxide, (2,4,6-trimethylbenzoyl)-(2,4,6-trimethoxybenzoyl)-(b-methylpropyl)phosphine oxide, (2,4,6-trimethylbenzoyl)-(2,4-dimethoxybenzoyl)-(1-methylpropyl)phosphine oxide, (2,4,6-trimethylbenzoyl)-(2,6-diethoxybenzoyl)-(1-methylpropyl)phosphine oxide, (2,4,6-trimethylbenzoyl)-(2,6-dimethoxy-4-methylbenzoyl)-(1-methylpropyl)phosphine oxide, (2,4,6-trimethylbenzoyl)-(2,6-dichlorobenzoyl)-(1-methylpropyl)phosphine oxide, (2,4,6-trimethylbenzoyl)-(2,4,6-trichlorobenzoyl)-(1-methylpropyl)phosphine oxide, (2,4,6-trimethylbenzoyl)-{2,6-bis(trifluoromethyl)benzoyl}-(1-methylpropyl)phosphine oxide, (2,6-dimethoxybenzoyl)-(2,6-dimethylbenzoyl)-(1-methylpropyl)phosphine oxide, (2,6-dimethoxybenzoyl)-(2,6-diethylbenzoyl)-(1-methylpropyl)phosphine oxide, (2,6-dimethoxybenzoyl)-(2,4,6-trimethylbenzoyl)-(1-methylpropyl)phosphine oxide, (2,6-dimethoxybenzoyl)-(2,6-dimethyl-4-tert-butylbenzoyl)-(1-methylpropyl)phosphine oxide, (2,6-dimethoxybenzoyl)-(2,4,6-trimethoxybenzoyl)-(1-methylpropyl)phosphine oxide, (2,6-dimethoxybenzoyl)-(2,4-dimethoxybenzoyl)-(1-methylpropyl)phosphine oxide, (2,6-dimethoxybenzoyl)-(2,6-diethoxybenzoyl)-(1-methylpropyl)phosphine oxide, (2,6-dimethoxybenzoyl)-(2,6-dimethoxy-4-methylbenzoyl)-(1-methylpropyl)phosphine oxide, (2,6-dimethoxybenzoyl)-(2,6-dichlorobenzoyl)-(1-methylpropyl)phosphine oxide, (2,6-dimethoxybenzoyl)-(2,4,6-trichlorobenzoyl)-(1-methylpropyl)phosphine oxide, (2,6-dimethoxybenzoyl)-{2, 6-bis(trifluoromethyl)benzoyl}-(1-methylpropyl)phosphine oxide, (2,6-dimethylbenzoyl)-(2,6-diethylbenzoyl)-(1-methylpropyl)-phosphine oxide, (2,6-dimethylbenzoyl)-(2,4,6-trimethylbenzoyl)-(1-methylpropyl)phosphine oxide, (2,6-dimethylbenzoyl)-(2,6-dimethyl-4-tert-butylbenzoyl)-(1-methylpropyl)phosphine oxide, (2,6-dimethylbenzoyl)-(2,4,6-trimethoxybenzoyl)-(1-methylpropyl)phosphine oxide, (2,6-dimethylbenzoyl)-(2,4-dimethoxybenzoyl)-(1-methylpropyl)phosphine oxide, (2,6-dimethylbenzoyl)-(2,6-diethoxybenzoyl)-(1-methylpropyl)phosphine oxide, (2,6-dimethylbenzoyl)-(2,6-dimethoxy-4-methylbenzoyl)-(1-methylpropyl)phosphine oxide, (2,6-dimethylbenzoyl)-(2,6-dichlorobenzoyl)-(1-methylpropyl)phosphine oxide, (2,6-dimethylbenzoyl)-(2,4,6-trichlorobenzoyl)-(1-methylpropyl)phosphine oxide, (2,6-dimethylbenzoyl)-{2,6-bis(trifluoromethyl)benzoyl}-(1-methylpropyl)phosphine oxide, (2,4,6-trimethoxybenzoyl)-(2,6-dimethylbenzoyl)-(1-methylpropyl)phosphine oxide, (2,4,6-trimethoxybenzoyl)-(2,6-diethylbenzoyl)-(1-methylpropyl)phosphine oxide, (2,4,6-trimethoxybenzoyl)-(2,4,6-trimethylbenzoyl)-(1-methylpropyl)phosphine oxide, (2,4,6-trimethoxybenzoyl)-(2,6-dimethyl-4-tert-butylbenzoyl)-(1-methylpropyl)phosphine oxide, (2,4,6-trimethoxybenzoyl)-(2,4-dimethoxybenzoyl)-(1-methylpropyl)phosphine oxide, (2,4,6-trimethoxybenzoyl)-(2,6-diethoxybenzoyl)-(1-methylpropyl)phosphine oxide, (2,4,6-trimethoxybenzoyl)-(2,6-dichlorobenzoyl)-(1-methylpropyl)phosphine oxide, (2,4,6-trimethoxybenzoyl)-{2,6-bis(trifluoromethyl)benzoyl}-(1-methylpropyl)phosphine oxide, (2,6-dimethyl-4-tert-butylbenzoyl)-(2,6-dimethylbenzoyl)-(1-methylpropyl)phosphine oxide, (2,6-dimethyl-4-tert-butylbenzoyl)-(2,6-diethylbenzoyl)-(1-methylpropyl)phosphine oxide, (2,6-dimethyl-4-tert-butylbenzoyl)-(2,4,6-trimethylbenzoyl)-(1-methylpropyl)phosphine oxide, (2,6-dimethyl-4-tert-butylbenzoyl)-(2,6-dimethyl-4-tert-butylbenzoyl)-(1-methylpropyl)phosphine oxide, (2,6-dimethyl-4-tert-butylbenzoyl)-(2,4,6-trimethoxybenzoyl)-(1-methylpropyl)phosphine oxide, (2,6-dimethyl-4-tert-butylbenzoyl)-(2,4-dimethoxybenzoyl)-(1-methylpropyl)phosphine oxide, (2,6-dimethyl-4-tert-butylbenzoyl)-(2,6-diethoxybenzoyl)-(1-methylpropyl)phosphine oxide, (2,6-dimethyl-4-tert-butylbenzoyl)-(2,6-dimethoxy-4-methylbenzoyl)-(1-methylpropyl)phosphine oxide, (2,6-dimethyl-4-tert-butylbenzoyl)-(2,6-dichlorobenzoyl)-(1-methylpropyl)phosphine oxide, (2,6-dimethyl-4-tert-butylbenzoyl)-(2,4,6-trichlorobenzoyl)-(1-methylpropyl)phosphine oxide, (2,6-dimethyl-4-tert-butylbenzoyl)-{2,6-bis(trifluoromethyl)benzoyl}-(1-methylpropyl)phosphine oxide, (2,4,6-trimethylbenzoyl)-(2,6-dimethylbenzoyl)-(2,4,4-trimethylpentyl)phosphine oxide, (2,4,6-trimethylbenzoyl)-(2,6-diethylbenzoyl)-(2,4,4-trimethylpentyl)phosphine oxide, (2,4,6-trimethylbenzoyl)-(2,6-diethylbenzoyl)-(2,4,4-trimethylpentyl)phosphine oxide, (2,4,6-trimethylbenzoyl)-(2,4,6-trimethoxybenzoyl)-(2,4,4-trimethylpentyl)phosphine oxide, (2,4,6-trimethylbenzoyl)-(2,4-dimethoxybenzoyl)-(2,4,4-trimethylpentyl)phosphine oxide, (2,4,6-trimethylbenzoyl)-(2,6-diethoxybenzoyl)-(2,4,4-trimethylpentyl)phosphine oxide, (2,4,6-trimethylbenzoyl)-(2,6-dimethoxy-4-methylbenzoyl)-(2,4,4-trimethylpentyl)phosphine oxide, (2,4,6-trimethylbenzoyl)-(2,6-dichlorobenzoyl)-(2,4,4-trimethylpentyl)phosphine oxide, (2,4,6-trimethylbenzoyl)-(2,4,6-trichlorobenzoyl)-(2,4,4-trimethylpentyl)phosphine oxide, (2,4,6-trimethylbenzoyl)-{2,6-bis(trifluoromethyl)benzoyl}-(2,4,4-trimethylpentyl)phosphine oxide, (2,6-dimethoxybenzoyl)-(2,6-dimethylbenzoyl)-(2,4,4-trimethylpentyl)phosphine oxide, (2,6-dimethoxybenzoyl)-(2,6-diethylbenzoyl)-(2,4,4-trimethylpentyl)phosphine oxide, (2,6-dimethoxybenzoyl)-(2,4,6-trimethylbenzoyl)-(2,4,4-trimethylpentyl)phosphine oxide, (2,6-dimethoxybenzoyl)-(2,6-dimethyl-4-tert-butylbenzoyl)-(2,4,4-trimethylpentyl)phosphine oxide, (2,6-dimethoxybenzoyl)-(2,4,6-trimethoxybenzoyl)-(2,4,4-trimethylpentyl)phosphine oxide, (2,6-dimethoxybenzoyl)-(2,4-dimethoxybenzoyl)-(2,4,4-trimethylpentyl)phosphine oxide, (2,6-dimethoxybenzoyl)-(2,6-diethoxybenzoyl)-(2,4,4-trimethylpentyl)phosphine oxide, (2,6-dimethoxybenzoyl)-(2,6-dimethoxy-4-methylbenzoyl)-(2,4,4-trimethylpentyl)phosphine oxide, (2,6-dimethoxybenzoyl)-(2,6-dichlorobenzoyl)-(2,4,4-trimethylpentyl)phosphine oxide, (2,6-dimethoxybenzoyl)-(2,4,6-trichlorobenzoyl)-(2,4,4-trimethylpentyl)phosphine oxide, (2,6-dimethoxybenzoyl)-{2,6-bis(trifluoromethyl)benzoyl}-(2,4,4-trimethylpentyl)phosphine oxide, (2,6-dimethylbenzoyl)-(2,4,6-trimethylbenzoyl)-(2,4,4-trimethylpentyl)phosphine oxide, (2,6-dimethylbenzoyl)-(2,6-dimethyl-4-tert-butylbenzoyl)-(2,4,4-trimethylpentyl)phosphine oxide, (2,6-dimethylbenzoyl)-(2,4,6-trimethoxybenzoyl)-(2,4,4-trimethylpentyl)phosphine oxide, (2,6-dimethylbenzoyl)-(2,4-dimethoxybenzoyl)-(2,4,4-trimethylpentyl)phosphine oxide, (2,6-dimethylbenzoyl)-(2,6-diethoxybenzoyl)-(2,4,4-trimethylpentyl)phosphine oxide, (2,6-dimethylbenzoyl)-(2,6-dimethoxy-4-methylbenzoyl)-(2,4,4-trimethylpentyl)phosphine oxide, (2,6-dimethylbenzoyl)-(2,6-dichlorobenzoyl)-(2,4,4-trimethylpentyl)phosphine oxide, (2,6-dimethylbenzoyl)-(2,4,6-trichlorobenzoyl)-(2,4,4-trimethylpentyl)phosphine oxide, (2,6-dimethylbenzoyl)-{2,6-bis(trifluoromethyl)benzoyl}-(2,4,4-trimethylpentyl)phosphine oxide, (2,4,6-trimethoxybenzoyl)-(2,6-dimethylbenzoyl)-(2,4,4-trimethylpentyl)phosphine oxide, (2,4,6-trimethoxybenzoyl)-(2,6-diethylbenzoyl)-(2,4,4-trimethylpentyl)phosphine oxide, (2,4,6-trimethoxybenzoyl)-(2,4,6-trimethylbenzoyl)-(2,4,4-trimethylpentyl)phosphine oxide, (2,4,6-trimethoxybenzoyl)-(2,6-dimethyl-4-tert-butylbenzoyl)-(2,4,4-trimethylpentyl)phosphine oxide, (2,4,6-trimethoxybenzoyl)-(2,4-dimethoxybenzoyl)-(2,4,4-trimethylpentyl)phosphine oxide, (2,4,6-trimethoxybenzoyl)-(2,6-diethoxybenzoyl)-(2,4,4-trimethylpentyl)phosphine oxide, (2,4,6-trimethoxybenzoyl)-(2,6-dichlorobenzoyl)-(2,4,4-trimethylpentyl)phosphine oxide, (2,4,6-trimethoxybenzoyl)-{2,6-bis(trifluoromethyl)benzoyl}-(2,4,4-trimethylpentyl)phosphine oxide, (2,6-dimethyl-4-tert-butylbenzoyl)-(2,6-dimethylbenzoyl)-(2,4,4-trimethylpentyl)phosphine oxide, (2,6-dimethyl-4-tert-butylbenzoyl)-(2,6-diethylbenzoyl)-(2,4,4-trimethylpentyl)phosphine oxide, (2,6-dimethyl-4-tert-butylbenzoyl)-(2,4,6-trimethylbenzoyl)-(2,4,4-trimethylpentyl)phosphine oxide, (2,6-dimethyl-4-tert-butylbenzoyl)-(2,6-dimethyl-4-tert-butylbenzoyl)-(2,4,4-trimethylpentyl)phosphine oxide, (2,6-dimethyl-4-tert-butylbenzoyl)-(2,4,6-trimethoxybenzoyl)-(2,4,4-trimethylpentyl)phosphine oxide, (2,6-dimethyl-4-tert-butylbenzoyl)-(2,4-dimethoxybenzoyl)-(2,4,4-trimethylpentyl)phosphine oxide, (2,6-dimethyl-4-tert-butylbenzoyl)-(2,6-diethoxybenzoyl)-(2,4,4-trimethylpentyl)phosphine oxide, (2,6-dimethyl-4-tert-butylbenzoyl)-(2,6-dimethoxy-4-methylbenzoyl)-(2,4,4-trimethylpentyl)phosphine oxide, (2,6-dimethyl-4-tert-butylbenzoyl)-(2,6-dichlorobenzoyl)-(2,4,4-trimethylpentyl)phosphine oxide, (2,6-dimethyl-4-tert-butylbenzoyl)-(2,4,6-trichlorobenzoyl)-(2,4,4- trimethylpentyl)phosphine oxide, (2,6-dimethyl-4-tert-butylbenzoyl)-{2,6-bis(trifluoromethyl)benzoyl}-(2,4,4-trimethylpentyl)phosphine oxide, (2,4,6-trimethylbenzoyl)-(2,6-dimethylbenzoyl)cyclopentylphosphine oxide, (2,4,6-trimethylbenzoyl)-(2,6-diethylbenzoyl)cyclopentylphosphine oxide, (2,4,6-trimethylbenzoyl)-(2,6-dimethyl-4-tert-butylbenzoyl)cyclopentylphosphine oxide, (2,4,6-trimethylbenzoyl)-(2,4,6-trimethoxybenzoyl)cyclopentylphosphine oxide, (2,4,6-trimethylbenzoyl)-(2,4-dimethoxybenzoyl)cyclopentylphosphine oxide, (2,4,6-trimethylbenzoyl)-(2,6-diethoxybenzoyl)cyclopentylphosphine oxide, (2,4,6-trimethylbenzoyl)-(2,6-dimethoxy-4-methylbenzoyl)cyclopentylphosphine oxide, (2,4,6-trimethylbenzoyl)-(2,6-dichlorobenzoyl)cyclopentylphosphine oxide, (2,4,6-trimethylbenzoyl)-(2,4,6-trichlorobenzoyl)cyclopentylphosphine oxide, (2,4,6-trimethylbenzoyl)-{2,6-bis(trifluoromethyl)benzoyl}-cyclopentylphosphine oxide, (2,6-dimethoxybenzoyl)-(2,6-dimethylbenzoyl)cyclopentylphosphine oxide, (2,6-dimethoxybenzoyl)-(2,6-diethylbenzoyl)cyclopentylphosphine oxide, (2,6-dimethoxybenzoyl)-(2,4,6-trimethylbenzoyl)cyclopentylphosphine oxide, (2,6-dimethoxybenzoyl)-(2,6-dimethyl-4-tert-butylbenzoyl)cyclopentylphosphine oxide, (2,6-dimethoxybenzoyl)-(2,4,6-trimethoxybenzoyl)cyclopentylphosphine oxide, (2,6-dimethoxybenzoyl)-(2,4-dimethoxybenzoyl)cyclopentylphosphine oxide, (2,6-dimethoxybenzoyl)-(2,6-diethoxybenzoyl)cyclopentylphosphine oxide, (2,6-dimethoxybenzoyl)-(2,6-dimethoxy-4-methylbenzoyl)cyclopentylphosphine oxide, (2,6-dimethoxybenzoyl)-(2,6-dichlorobenzoyl)cyclopentylphosphine oxide, (2,6-dimethoxybenzoyl)-(2,4,6-trichlorobenzoyl)cyclopentylphosphine oxide, (2,6-dimethoxybenzoyl)-{2,6-bis(trifluoromethyl)benzoyl}cyclopentylphosphine oxide, (2,6-dimethylbenzoyl)-(2,6-diethylbenzoyl)cyclopentylphosphine oxide, (2,6-dimethylbenzoyl)-(2,4,6-trimethylbenzoyl)cyclopentylphosphine oxide, (2,6-dimethylbenzoyl)-(2,6-dimethyl-4-tert-butylbenzoyl)cyclopentylphosphine oxide, (2,6-dimethylbenzoyl)-(2,4,6-trimethoxybenzoyl)cyclopentylphosphine oxide, (2,6-dimethylbenzoyl)-(2,4-dimethoxybenzoyl)cyclopentylphosphine oxide, (2,6-dimethylbenzoyl)-(2,6-diethoxybenzoyl)cyclopentylphosphine oxide, (2,6-dimethylbenzoyl)-(2,6-dimethoxy-4-methylbenzoyl)cyclopentylphosphine oxide, (2,6-dimethylbenzoyl)-(2,6-dichlorobenzoyl)cyclopentylphosphine oxide, (2,6-dimethylbenzoyl)-(2,4,6-trichlorobenzoyl)cyclopentylphosphine oxide, (2,6-dimethylbenzoyl)-{2,6-bis(trifluoromethyl)benzoyl}cyclopentylphosphine oxide, (2,4,6-trimethoxybenzoyl)-(2,6-dimethylbenzoyl)cyclopentylphosphine oxide, (2,4,6-trimethoxybenzoyl)-(2,6-diethylbenzoyl)cyclopentylphosphine oxide, (2,4,6-trimethoxybenzoyl)-(2,4,6-trimethylbenzoyl)cyclopentylphosphine oxide, (2,4,6-trimethoxybenzoyl)-(2,6-dimethyl-4-tert-butylbenzoyl)cyclopentylphosphine oxide, (2,4,6-trimethoxybenzoyl)-(2,4-dimethoxybenzoyl)cyclopentylphosphine oxide, (2,4,6-trimethoxybenzoyl)-(2,6-diethoxybenzoyl)cyclopentylphosphine oxide, (2,4,6-trimethoxybenzoyl)-(2,6-dichlorobenzoyl)cyclopentylphosphine oxide, (2,4,6-trimethoxybenzoyl)-{2,6-bis(trifluoromethyl)benzoyl}cyclopentylphosphine oxide, (2,6-dimethyl-4-tert-butylbenzoyl)-(2,6-dimethylbenzoyl)cyclopentylphosphine oxide, (2,6-dimethyl-4-tert-butylbenzoyl)-(2,6-diethylbenzoyl)cyclopentylphosphine oxide, (2,6-dimethyl-4-tert-butylbenzoyl)-(2,4,6-trimethylbenzoyl)cyclopentylphosphine oxide, (2,6-dimethyl-4-tert-butylbenzoyl)-(2,6-dimethyl-4-tert-butylbenzoyl)cyclopentylphosphine oxide, (2,6-dimethyl-4-tert-butylbenzoyl)-(2,4,6-trimethoxybenzoyl)cyclopentylphosphine oxide, (2,6-dimethyl-4-tert-butylbenzoyl)-(2,4-dimethoxybenzoyl)cyclopentylphosphine oxide, (2,6-dimethy-4-tert-butylbenzoyl)-(2,6-diethoxy benzoyl)cyclopentylphosphine oxide, (2,6-dimethyl-4-tert-butylbenzoyl)-(2,6-dimethoxy-4-methylbenzoyl)cyclopentylphosphine oxide, (2,6-dimethyl-4-tert-butylbenzoyl)-(2,6-dichlorobenzoyl)cyclopentylphosphine oxide, (2,6-dimethyl-4-tert-butylbenzoyl)-(2,4,6-trichlorobenzoyl)cyclopentylphosphine oxide, (2,6-dimethyl-4-tert-butylbenzoyl)-(2,6-bis(trifluoromethyl)benzoylcyclopentylphosphine oxide, (2,4,6-trimethylbenzoyl)-(2,6-dimethylbenzoyl)cyclohexylphosphine oxide, (2,4,6-trimethylbenzoyl)-(2,6-diethylbenzoyl)cyclohexylphosphine (2,4,6-trimethylbenzoyl)-(2,4,6-trimethoxybenzoyl)cyclohexylphosphine oxide, (2,4,6-trimethylbenzoyl)-(2,4-dimethoxybenzoyl)cyclohexylphosphine oxide, (2,4,6-trimethylbenzoyl)-(2,6-diethoxybenzoyl)cyclohexylphosphine oxide, (2,4,6-trimethylbenzoyl)-(2,6-dimethoxy-4-methylbenzoyl)cyclohexylphosphine oxide, (2,4,6-trimethylbenzoyl)-(2,6-dichlorobenzoyl)cyclohexylphosphine oxide, (2,4,6-trimethylbenzoyl)-(2,4,6-trichlorobenzoyl)cyclohexylphosphine oxide, (2,4,6-trimethylbenzoyl)-{2,6-bimethyl-benzoyl}cyclohexylphosphine oxide, (2,6-dimethoxybenzoyl)-(2,6-dimethylbenzoyl)cyclohexylphosphine oxide, (2,6-dimethoxybenzoyl)-(2,6-diethylbenzoyl)cyclohexylphosphine oxide, (2,6-dimethoxybenzoyl)-(2,4,6-trimethylbenzoyl)cyclohexylphosphine oxide, (2,6-dimethoxybenzoyl)-(2,6-dimethy-4-tert-butylbenzoyl)cyclohexylphosphine oxide, (2,6-dimethoxybenzoyl)-(2,4,6-trimethoxybenzoyl)cyclohexylphosphine oxide, (2,6-dimethoxybenzoyl)-(2,4-dimethoxybenzoyl)cyclohexylphosphine oxide, (2,6-dimethoxybenzoyl)-(2,6-diethoxybenzoyl)cxcyclohexphosphine oxide, (2,6-dimethoxybenzoyl)-(2,6-dimethoxy-4-methylbenzoyl)cyclohexylphosphine oxide, (2,6-dimethoxybenzoyl)-(2,6-dichlorobenzoyl)cyclohexylphosphine oxide, (2,6-dimethoxybenzoyl)-(2,4,6-trichlorobenzoyl)cyclohexylphosphine oxide, (2,6-dimethoxybenzoyl)-{2,6-bis(trifluoromethyl)benzoyl}cyclohexylphosphine oxide, (2,6-dimethylbenzoyl)-(2,6-diethylbenzoyl)cyclohexylphosphine oxide, (2,6-dimethylbenzoyl)-(2,4,6-trimethylbenzoyl)cyclohexylphosphine oxide, (2,6-dimethylbenzoyl)-(2,6-dimethyl-4-tert-butylbenzoyl)cyclohexylphosphine oxide, (2,6-dimethylbenzoyl)-(2,4,6-trimethoxybenzoyl)cyclohexylphosphine oxide, (2,6-dimethylbenzoyl)-(2,4-dimethoxybenzoyl)cyclohexylphosphine oxide, (2,6-dimethylbenzoyl)-(2,6-diethoxybenzoyl)cyclohexylphosphine oxide, (2,6-dimethylbenzoyl)-(2,6-dimethoxy-4-methylbenzoyl)cyclohexylphosphine oxide, (2,6-dimethylbenzoyl)-(2,6-dichlorobenzoyl)cyclohexylphosphine oxide, (2,6-dimethylbenzoyl)-(2,4,6-trichlorobenzoyl)cyclohexylphosphine oxide, (2,6-dimethylbenzoyl)-{2,6-bis(trifluoromethyl)benzoyl}cyclohexylphosphine oxide, (2,4,6-trimethoxybenzoyl)-(2,6-dimethylbenzoyl)cyclohexylphosphine oxide, (2,4,6-trimethoxybenzoyl)-(2,6-diethylbenzoyl)cyclohexylphosphine oxide, (2,4,6-trimethoxybenzoyl)-(2,4,6-trimethylbenzoyl)cyclohexylphosphine oxide, (2,4,6-trimethoxybenzoyl)-(2,6-dimethyl-4-tert-butylbenzoyl)cyclohexylphosphine oxide, (2,4,6-trimethoxybenzoyl)-(2,4-dimethoxybenzoyl)

cyclohexylphosphine oxide, (2,4,6-trimethoxybenzoyl)-(2,6-diethoxybenzoyl)cyclohexylphosphine oxide, (2,4,6-trimethoxybenzoyl)-(2,6-dichlorobenzoyl)cyclohexylphosphine oxide, (2,4,6-trimethoxybenzoyl)-{2,6-bis(trifluoromethyl)benzoyl}cyclohexylphosphine oxide, (2,6-dimethyl-4-tert-butylbenzoyl)-(2,6-dimethylbenzoyl)cyclohexylphosphine oxide, (2,6-dimethyl-4-tert-butylbenzoyl)-(2,6-diethylbenzoyl)cyclohexylphosphine oxide, (2,6-dimethyl-4-tert-butylbenzoyl)-(2,4,6-trimethylbenzoyl)cyclohexylphosphine oxide, (2,6-dimethyl-4-tert-butylbenzoyl)-(2,6-dimethyl-4-tert-butylbenzoyl)cyclohexylphosphine oxide, (2,6-dimethyl-4-tert-butylbenzoyl)-(2,4,6-trimethoxybenzoyl)cyclohexylphosphine oxide, (2,6-dimethyl-4-tert-butylbenzoyl)-(2,4-dimethoxybenzoyl)cyclohexylphosphine oxide, (2,6-dimethyl-4-tert-butylbenzoyl)-(2,6-diethoxybenzoyl)cyclohexylphosphine oxide, (2,6-dimethyl-4-tert-butylbenzoyl)-(2,6-dimethoxy-4-methylbenzoyl)cyclohexylphosphine oxide, (2,6-dimethyl-4-tert-butylbenzoyl)-(2,6-dichlorobenzoyl)cyclohexylphosphine oxide, (2,6-dimethyl-4-tert-butylbenzoyl)-(2,4,6-trichlorobenzoyl)cyclohexylphosphine oxide, (2,6-dimethyl-4-tert-butylbenzoyl)-{2,6-bis(trifluoromethyl)benzoyl}cyclohexylphosphine oxide.

The compounds of the formula II where x=0 (formula II') are obtained by reacting an alkylacylphosphine of the formula I with an acid halide of the formula (IV):

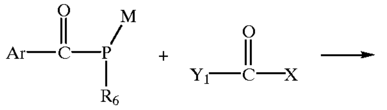

(I) (IV)

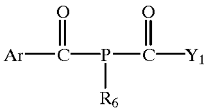

(II')

The meanings of the radicals Ar, $R_6$, M, X and Y, are as described above. The starting materials are advantageously reacted in a molar ratio of 1:1. A slight excess of one or other of the components, e.g. up to 20%, is, however, not critical. The desired product forms in this case too, although the proportion of undesired byproduct can be influenced. The reaction conditions for this reaction correspond to those given above in connection with the preparation of the compounds of the formula I.

Compounds of the formula II where x=1 and A is oxygen are prepared by oxidation of the compounds of the formula (II'), and compounds of the formula II where A is sulfur are prepared by sulfurization of the compounds of the formula II':

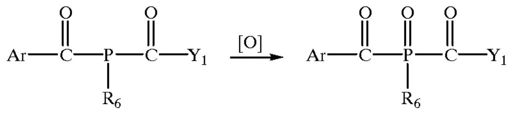

-continued

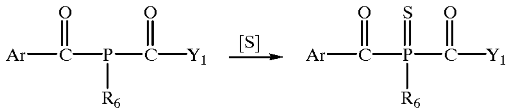

(II') (II)

Prior to the oxidation or sulfurization, the phosphine II' can be isolated by customary separation methods familiar to the person skilled in the art, although the reaction can also be carried out immediately after the previous reaction step without isolation of the phosphine.

During the preparation of the oxide, the oxidation of the phosphine is carried out using oxidizing agents customary in the art. Suitable oxidizing agents are primarily hydrogen peroxide and organic peroxy compounds, for example peracetic acid or t-butyl hydroperoxide, air or pure oxygen.

The oxidation is advantageously carried out in solution. Suitable solvents are aromatic hydrocarbons, for example benzene, toluene, m-xylene, p-xylene, ethylbenzene or mesitylene, or aliphatic hydrocarbons, e.g. alkanes and alkane mixtures, such as petroleum ether, hexane or cyclohexane. Further suitable examples are dimethyl ether, diethyl ether, methyl propyl ether, 1,2-dimethoxyethane, bis(2-methoxyethyl) ether, dioxane or tetrahydrofuran. Preference is given to using toluene.

The reaction temperature during the oxidation is advantageously kept between 0° and 120° C., preferably between 20° and 80° C.

The reaction products of the formula (II) can be isolated and purified by customary processing measures familiar to the person skilled in the art.

The preparation of the respective sulfide is carried out by reaction with sulfur. The bisacylphosphines (II') are here reacted with an equimolar to 2-fold molar amount of elemental sulfur e.g. without a diluent or optionally in a suitable inert organic solvent. Examples of suitable solvents are those described for the oxidation reaction. It is, however, also possible to use, for example, aliphatic or aromatic ethers, for example dibutyl ether, dioxane, diethylene glycol dimethyl ether or diphenyl ether at temperatures of from 20° to 250° C., preferably 60° to 120° C. The resulting bisacylphosphine sulfide, or its solution is advantageously freed from any elemental sulfur which may still be present by filtration. Following removal of the solvent, the bisacylphosphine sulfide can be isolated in pure form by distillation, recrystallization or chromatographic separation methods.

It is advantageous to carry out all of the reactions described above with the exclusion of air in an inert gas atmosphere, e.g. under nitrogen or argon gas. Moreover, stirring of the respective reaction mixture is advantageously appropriate.

The invention likewise provides a process for the preparation of the compounds of the formula II, from compounds of the formula I as starting materials, by (1) reaction of an acyl halide of the formula IV (IV)

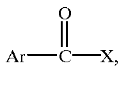

in which

Ar is as defined above, and

X is Cl or Br;

with a dimetalated organophosphine of the formula V (V)

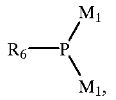

in which $R_6$ is as defined above; and $M_1$ is Na, Li or K;

in the molar ratio of approximately 1:1;

(2) subsequent reaction of the product with an acyl halide of the formula IVa (IVa)

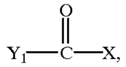

in which $Y_1$ is as defined above; and

X is as defined above;

with the proviso that the acyl halide of the formula IV is not identical to the acyl halide of the formula IVa;

in the molar ratio of approximately 1:1; and, (3) if compounds of the formula II in which A is oxygen or sulfur are to be obtained, subsequent oxidation or sulfurization of the resulting phosphine compounds.

Furthermore, the compounds of the formula II can also be prepared by reacting the compound of the formula I with phosgene, analogously to the description in "W. A. Henderson et al., J. Am. Chem. Soc. 1960, 82, 5794" or "GB 904 086" or in "Organic Phosphorous Compounds, Editors: R. M. Kosolapoff and L. Maier, Wiley-Interscience 1972, Vol.1, page 28" or "Houben-Weyl, Methoden der Organischen Chemie, Vol. XII/1, page 201", to give the corresponding phosphine chloride (Ii). Compounds of the formula (Ii) can, as described in "Organic Phosphorous Compounds, Editors: R. M. Kosolapoff and L. Maier, Wiley-Interscience 1972, Vol.4, pages 268–269", be reacted with alcohols to give compounds of the formula (Iii), which are then reacted directly with an acyl halide of the formula IVa, in analogy with the description in U.S. Pat. No. 4,324,744 (by Michaelis-Arbuzov reaction), to give compounds of the formula II. In this case, the oxidation step is superfluous.

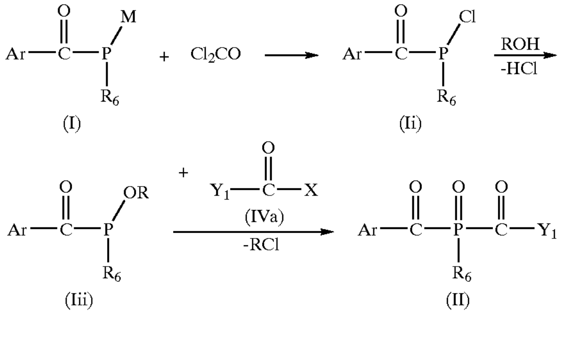

Ar and $Y_1$ are as defined in claim 1, although Ar and $Y_1$ in this case may also be the same radical; X is Cl or Br; M and $R_6$ are likewise as defined in claim 1, and R is any alcohol radical, e.g. $C_1$–$C_{12}$alkyl, $C_5$–$C_8$cycloalkyl, for example cyclopentyl or cyclohexyl, or benzyl.

The chlorination with phosgene with the elimination of carbon monoxide is advantageously carried out by introducing phosgene, with stirring, into a solution of (I) in an inert solvent. For example, phosgene is introduced at −70° C. to 20° C., in particular at −40°C. to 0° C. Solvents which may be used are, for example, chlorinated alkanes, for example dichloromethane, dichloroethane or tetrachloromethane; alkanes, for example hexane; cycloalkanes, for example cyclohexane, or aromatic solvents, for example toluene. The isolation of (Ii) is carried out, for example, by distillation under reduced pressure.

Such reactions are also described e.g. by R. Schmutzler et al. in, Z. Anorg. Allg. Chemie 1999, 625, pages 1979–1984.

The conversion of (Ii) to (Iii) is carried out for example in an inert solvent in the presence of a tertiary amine, for example triethylamine, tributylamine or pyridine. Here, the alcohol (ROH) is advantageously added dropwise to a solution (Ii) and tertiary amine in the solvent. The addition is preferably carried out at a temperature of from 60° C. to 140° C. Solvents which may be used are, for example, chlorinated alkanes, such as tetrachloromethane, dichloromethane, dichloroethane; alkanes, for example hexane; cycloalkanes, for example cyclohexane; or aromatic solvents, for example toluene. The isolation of (Iii) is carried out, for example, by distillation under reduced pressure. Such reactions have also been published e.g. by Y. A. Veits et al., in J. Gen. Chem. (USSR) 1991, 61, pages 108 ff.

The conversion of compounds of the formula (Iii) to compounds of the formula (II) is carried out by adding corresponding acyl halides (IVa) to a solution of (Iii) in an inert solvent. Here, the acyl halide is advantageously dissolved in the same solvent in which the previous reaction step has taken place. The addition is carried out, for example, at a temperature of from 40° C. to 140° C., preferably at 60° C. to 120° C., the alkyl halide (RCl) liberated during the reaction advantageously being removed by distillation from the reaction solution. Solvents which may be used here are, for example, alkanes, for example hexane, octane; cycloalkanes, for example cyclohexane; ethers, for example tert-butyl methyl ether, tetrahydrofuran, dioxane; or aromatic solvents, for example toluene or xylene. The compounds of the structure (II) are advantageously isolated and purified, for example, by distillation under reduced pressure, crystallization or by chromatography.

Compounds of the formula (Iii) can be oxidized using suitable oxidizing agents, such as peroxo acids, hydrogen peroxide or hydrogen peroxide/urea, to give the corresponding phosphinic esters (Iiii):

(Iiii)

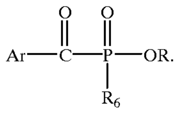

This preparation process is novel. The compounds prepared in this way are also photoinitiators and are, for example, as those described in U.S. Pat. No. 4,324,744.

The invention thus also provides a process for the preparation of compounds of the formula II in which A is oxygen and x is 1, by (1) reaction of the compounds of the formula (I), as described above, (I)

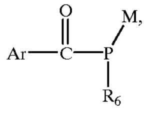

in which

Ar, M and $R_6$ are as described above, with phosgene to give the corresponding phosphine chloride (Ii)

(Ii)

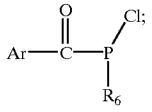

(2) subsequent reaction with an alcohol to give the compound of the formula (Iii)

(Iii)

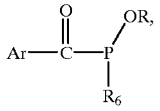

in which

R is the radical of an alcohol, in particular $C_1$–$C_{12}$alkyl, $C_5$–$C_8$cycloalkyl or benzyl; and (3) reaction of the resulting compound of the formula (Iii) with an acyl halide

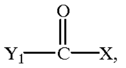

in which $Y_1$ is as defined above, and

X is Cl or Br, to give a compound of the formula II in which $Y_1$ and Ar do not necessarily have to be different.

As already mentioned, slightly unsymmetrical monoacylphosphines, monoacylphosphine oxides or sulfides can also be obtained from the compounds of the formula I.

The invention thus also provides compounds of the formula III (III)

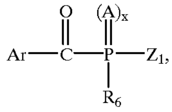

in which

A is O or S;

x is 0 or 1;

Ar is a group

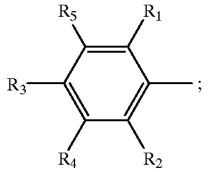

or Ar is cyclopentyl, cyclohexyl, naphthyl, anthracyl, biphenylyl or an O-, S- or N-containing 5- or 6-membered heterocyclic ring, where the radicals cyclopentyl, cyclohexyl, naphthyl, anthracyl, biphenylyl and 5- or 6-membered heterocyclic ring are unsubstituted or substituted by halogen, $C_1$–$C_4$alkyl and/or $C_1$–$C_4$alkoxy;

$R_1$ and $R_2$ independently of one another are $C_1$–$C_2$alkyl, $OR_{11}$, $CF_3$ or halogen;

$R_3$, $R_4$ and $R_5$ independently of one another are hydrogen, $C_1$–$C_{20}$alkyl, $OR_{11}$ or halogen;

or in each case two of the radicals $R_1$, $R_2$, $R_3$, $R_4$ and $R_5$ together form $C_1$–$C_{20}$alkylene which can be interrupted by O, S or -$NR_{14}$;

$R_6$ is $C_1$–$C_{24}$alkyl, unsubstituted or substituted by $C_5$–$C_{24}$cycloalkenyl, phenyl, CN, $C(O)R_{11}$, $C(O)OR_{11}$, $C(O)N(R_{14})_2$, $OC(O)R_{11}$, $OC(O)OR_{11}$, $N(R_{14})C(O)N(R_{14})$, $OC(O)NR_{14}$, $N(R_{14})C(O)OR_{11}$, cycloalkyl, halogen, $OR_{11}$, $SR_{11}$, $N(R_{12})(R_{13})$ or

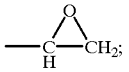

$C_2$–$C_{24}$alkyl which is interrupted once or more than once by nonconsecutive O, S or $NR_{14}$ and which is unsubstituted or substituted by phenyl, $OR_{11}$, $SR_{11}$, $N(R_{12})(R_{13})$, CN, $C(O)R_{11}$, $C(O)OR_{11}$, $C(O)N(R_{14})_2$ and/or

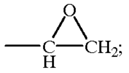

$C_2$–$C_{24}$alkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_5$–$C_{24}$cycloalkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_7$–$C_{24}$arylalkyl which is unsubstituted or substituted on the aryl group by $C_1$–$C_{12}$alkyl, $C_1$–$C_{12}$alkoxy or halogen;

$C_4$–$C_{24}$cycloalkyl which is uninterrupted or interrupted once or more than once by O, S and/or $NR_{14}$ and which is unsubstituted or substituted by $OR_{11}$, $SR_{11}$ or $N(R_{12})(R_{13})$;

or $C_8$–$C_{24}$arylcycloalkyl or $C_8$–$C_{24}$arylcycloalkenyl;

$R_{11}$ is H, $C_1$–$C_{20}$alkyl, $C_2$–$C_{20}$alkenyl, $C_3$–$C_8$cycloalkyl, phenyl, benzyl or $C_2$–$C_{20}$alkyl which is interrupted once or more than once by nonconsecutive O atoms and which is unsubstituted or substituted by OH and/or SH;

$R_{12}$ and $R_{13}$ independently of one another are hydrogen, $C_1$–$C_{20}$alkyl, $C_3$–$C_8$cycloalkyl, phenyl, benzyl or $C_2$–$C_{20}$alkyl, which is interrupted once or more than once by O or S and which is unsubstituted or substituted by OH and/or SH; or $R_{12}$ and $R_{13}$ together are $C_3$–$C_5$alkylene which is uninterrupted or interrupted by O, S or $NR_{14}$;

$Z_1$ is $C_1$–$C_{24}$alkyl which is unsubstituted or substituted once or more than once by $OR_{15}$, $SR_{15}$, $N(R_{16})(R_{17})$, phenyl, halogen, CN, —N═C═A,

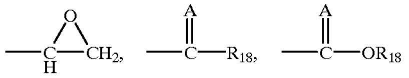

and/or

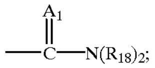

or $Z_1$ is $C_2$–$C_{24}$alkyl which is interrupted once or more than once by O, S or $NR_{14}$ and which can be substituted by $OR_{15}$, $SR_{15}$, $N(R_{16})(R_{17})$, phenyl, halogen,

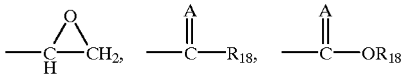

and/or

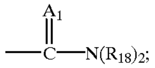

or $Z_1$ is $C_1$–$C_{24}$alkoxy, which is substituted once or more than once by phenyl, CN, —N═C═A,

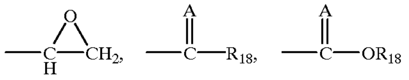

and/or

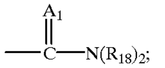

or $Z_1$ is

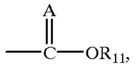

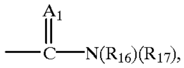

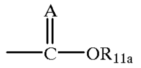

or

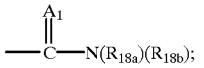

or $Z_1$ is unsubstituted $C_3$–$C_{24}$cycloalkyl or $C_3$–$C_{24}$cycloalkyl substituted by $C_1$–$C_{20}$alkyl, $OR_{11}$, $CF_3$ or halogen; unsubstituted $C_2$–$C_{24}$alkenyl or $C_2$–$C_{24}$alkenyl substituted by $C_6$–$C_{12}$aryl, CN, $(CO)OR_{15}$ or $(CO)N(R_{18})_2$; or $Z_1$ is $C_3$–$C_{24}$cycloalkenyl or is one of the radicals (f)

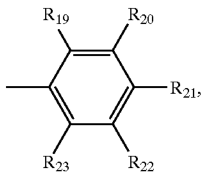

(g)

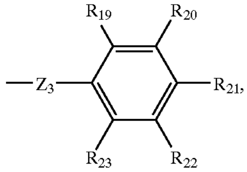

(h)

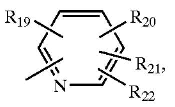

-continued (i)

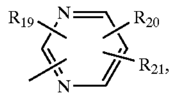

(k)

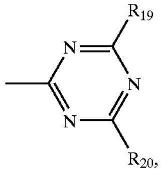

(l)

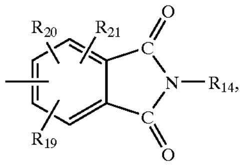

(m)

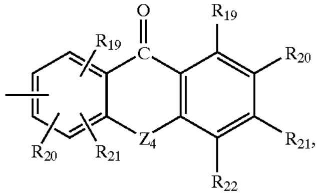

(n)

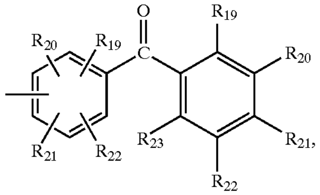

(o)

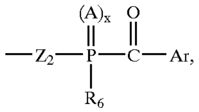

(p)

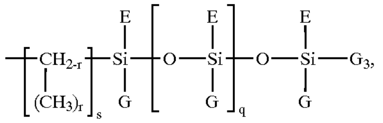

(q)

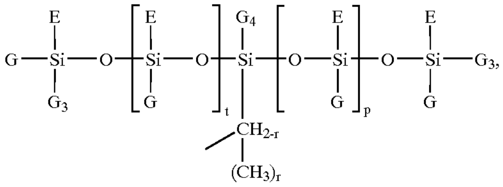

(t)

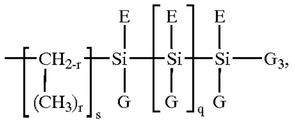

-continued (v)

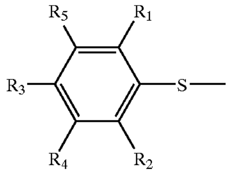

or (w)

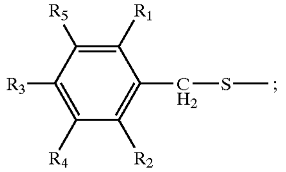

or $Z_1$ is $C_1$–$C_{24}$alkylthio, in which the alkyl radical is uninterrupted or interrupted once or more than once by nonconsecutive O or S, and is unsubstituted or substituted by $OR_{15}$, $SR_{15}$ and/or halogen; with the proviso that $Z_1$ and $R_6$ are not identical;

$A_1$ is O, S or $NR_{18a}$;

$Z_2$ is $C_1$–$C_{24}$alkylene; $C_2$–$C_{24}$alkylene interrupted once or more than once by O, S or $NR_{14}$; $C_2$–$C_{24}$alkenylene; $C_2$–$C_{24}$alkenylene interrupted once or more than once by O, S or $NR_{14}$; $C_3$–$C_{24}$cycloalkylene; $C_3$–$C_{24}$cycloalkylene interrupted once or more than once by O, S or $NR_{14}$; $C_3$–$C_{24}$cycloalkylene; $C_3$–$C_{24}$cycloalkenylene interrupted once or more than once by O, S or $NR_{14}$;

where the radicals $C_1$–$C_{24}$alkylene, $C_2$–$C_{24}$alkylene, $C_2$–$C_{24}$alkenylene, $C_3$–$C_{24}$cycloalkylene and $C_3$–$C_{24}$cycloalkenylene are unsubstituted or are substituted by $OR_{11}$, $SR_{11}$, $N(R_{12})(R_{13})$ and/or halogen; or $Z_2$ is one of the radicals

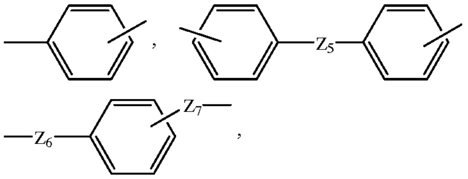

or where these radicals are unsubstituted or are substituted on the aromatic by $C_1$–$C_{20}$alkyl; $C_2$–$C_{20}$alkyl which is interrupted once or more than once by nonconsecutive O atoms and which is unsubstituted or substituted by OH and/or SH; $OR_{11}$, $SR_{11}$, $N(R_{12})(R_{13})$, phenyl, halogen, $NO_2$, CN, (CO)—$OR_{11}$, (CO)—$R_{11}$, (CO)—$N(R_{12})(R_{13})$, $SO_2R_{24}$, $OSO_2R_{24}$, $CF_3$ and/or $CCl_3$;

or $Z_2$ is a group (r)

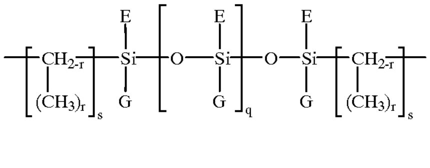

or

-continued (u)

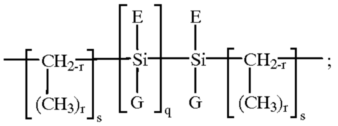

$Z_3$ is $CH_2$, CH(OH), $CH(CH_3)$ or $C(CH_3)_2$;

$Z_4$ is S, O, $CH_2$, C═O, $NR_{14}$ or a direct bond;

$Z_5$ is S, O, $CH_2$, $CHCH_3$, $C(CH_3)_2$, $C(CF_3)_2$, SO, $SO_2$, CO;

$Z_6$ and $Z_7$ independently of one another are $CH_2$, $CHCH_3$ or $C(CH_3)_2$;

r is0, 1 or2;

s is a number from 1 to 12;

q is a number from 0 to 50;

t and p are each a number from 0 to 20;

E, G, $G_3$ and $G_4$ independently of one another are unsubstituted $C_1$–$C_{12}$alkyl or $C_1$–$C_{12}$alkyl substituted by halogen, or are unsubstituted phenyl or phenyl substituted by one or more $C_1$–$C_4$alkyl; or are $C_2$–$C_{12}$alkenyl;

$R_{11a}$ is $C_1$–$C_{20}$alkyl substituted once or more than once by $OR_{15}$ or

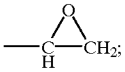

or is $C_2$–$C_{20}$alkyl which is interrupted once or more than once by nonconsecutive O atoms and is unsubstituted or substituted once or more than once by $OR_{15}$, halogen or

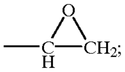

or $R_{11a}$ is $C_2$–$C_{20}$alkenyl, $C_3$–$C_{12}$alkynyl; or $R_{11a}$ is $C_3$–$C_{12}$cycloalkenyl which is substituted once or more than once by halogen, $NO_2$, $C_1$–$C_6$alkyl, $OR_{11}$ or $C(O)OR_{18}$; or $C_7$–$C_{16}$arylalkyl or $C_8$–$C_{16}$arylcycloalkyl;

$R_{14}$ is hydrogen, phenyl, $C_1$–$C_{12}$alkoxy, $C_1$–$C_{12}$alkyl or $C_2$–$C_{12}$alkyl which is interrupted once or more than once by O or S and which is unsubstituted or substituted by OH and/or SH;

$R_{15}$ has one of the meanings given for $R_{11}$ or is a radical

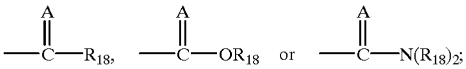

$R_{16}$ and $R_{17}$ independently of one another have one of the meanings given for $R_{12}$ or are a radical

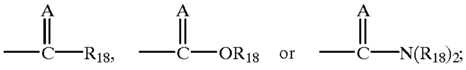

$R_{18}$ is hydrogen, $C_1$–$C_{24}$alkyl, $C_2$–$C_{12}$alkenyl, $C_3$–$C_8$cycloalkyl, phenyl, benzyl; $C_2$–$C_{20}$alkyl which is interrupted once or more than once by O or S and which is unsubstituted or substituted by OH;

$R_{18a}$ and $R_{18b}$ independently of one another are hydrogen; $C_1$–$C_{20}$alkyl, which is substituted once or more than once by $OR_{15}$, halogen, styryl, methylstyryl, —N═C═A or

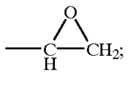

or $C_2$–$C_{20}$alkyl, which is interrupted once or more than once by nonconsecutive O atoms and which is unsubstituted or substituted once or more than once by $OR_{15}$, halogen, styryl, methylstyryl or

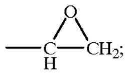

or $R_{18a}$ and $R_{18b}$ are $C_2$–$C_{12}$alkenyl; $C_5$–$C_{12}$cycloalkyl, which is substituted by —N=C=A or —$CH_2$—N=C=A and is additionally unsubstituted or substituted by one or more $C_1$–$C_4$alkyl; or $R_{18a}$ and $R_{18b}$ are $C_6$–$C_{12}$aryl, unsubstituted or substituted once or more than once by halogen, $NO_2$, $C_1$–$C_6$alkyl, $C_2$–$C_4$alkenyl, $OR_{11}$, —N=C=A, —$CH_2$—N=C=A or $C(O)OR_{18}$; or $R_{18a}$ and $R_{18b}$ are $C_7$–$C_{16}$arylalkyl; or $R_{18a}$ and $R_{18b}$ together are $C_8$–$C_{16}$arylcycloalkyl; or $R_{18a}$ and $R_{18b}$ independently of one another are

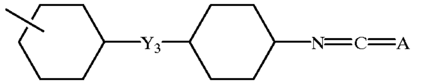

or

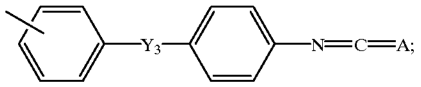

$Y_3$ is O, S, SO, $SO_2$, $CH_2$, $C(CH_3)_2$, $CHCH_3$, $C(CF_3)_2$, (CO), or a direct bond;

$R_{19}$, $R_{20}$, $R_{21}$, $R_{22}$ and $R_{23}$ independently of one another are hydrogen, $C_1$–$C_{20}$alkyl;

$C_2$–$C_{20}$alkyl, which is interrupted once or more than once by nonconsecutive O atoms and which is unsubstituted or substituted by OH and/or SH; or $R_{19}$, $R_{20}$, $R_{21}$, $R_{22}$ and $R_{23}$ are $OR_{11}$, $SR_{11}$, $N(R_{12})(R_{13})$, $NO_2$, CN, $SO_2R_{24}$, $OSO_2R_{24}$, $CF_3$, CCl3, halogen; or phenyl which is unsubstituted or substituted once or more than once by $C_1$–$C_4$alkyl or $C_1$–$C_4$alkoxy;

or in each case two of the radicals $R_{19}$, $R_{20}$, $R_{21}$, $R_{22}$ and $R_{23}$ together form $C_1$–$C_{20}$alkylene which is uninterrupted or interrupted by O, S or —$NR_{14}$;

$R_{24}$ is $C_1$–$C_{12}$alkyl, halogen-substituted $C_1$–$C_{12}$alkyl, phenyl, or phenyl substituted by $OR_{11}$ and/or $SR_{11}$;

with the proviso that $R_6$ and $Z_1$ are not identical.

In the compounds of the formula III the preferred meanings for the radicals Ar, $R_1$, $R_2$, $R_3$, $R_4$, $R_5$ and $R_6$ are analogous to those given above for the compounds of the formula I.

A in formula III is, in particular, oxygen, x is preferably 1 and Ar is preferably a group

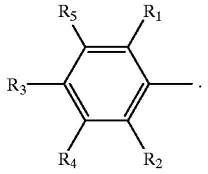

Preference is given to compounds of the formula III, in which Ar is a group

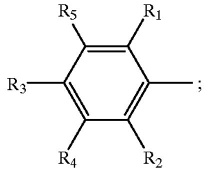

A is O; and x is 1; $R_1$ and $R_2$ independently of one another are $C_1$–$C_{12}$alkyl, $C_1$–$C_{12}$alkoxy, $CF_3$ or halogen; $R_3$, $R_4$ and $R_5$ independently of one another are hydrogen, $C_1$–$C_{12}$alkyl, $C_1$–$C_{12}$alkoxy or halogen; $R_6$ is $C_1$–$C_{12}$alkyl, unsubstituted or substituted by $OR_{11}$, cycloalkenyl, CN, $C(O)R_{11}$, $C(O)OR_{11}$, $C(O)N(R_{14})_2$, phenyl, cycloalkyl; $C_2$–$C_{12}$alkyl, which is interrupted once or more than once by nonconsecutive O, S or $NR_{14}$ and which is unsubstituted or substituted by $OR_{11}$, $SR_{11}$, $N(R_{12})(R_{13})$, CN, $C(O)R_{11}$, $C(O)OR_{11}$ and/or $C(O)N(R_{14})_2$; $C_2$–$C_{12}$alkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$; benzyl, cyclopentyl, cyclohexyl, $C_4$–$C_{12}$cycloalkyl which is uninterrupted or interrupted once or more than once by O, S and/or $NR_{14}$; or $C_8$–$C_{12}$arylcycloalkyl; $R_{12}$ and $R_{13}$ independently of one another are hydrogen, $C_1$–$C_4$alkyl, $C_3$–$C_6$cycloalkyl, phenyl, benzyl or $C_2$–$C_{12}$alkyl, which is interrupted once or more than once by O or S and which is unsubstituted or substituted by OH and/or SH, or $R_{12}$ and $R_{13}$ together are piperidino, morpholino or piperazino; $Z_1$ has the same meaning as $R_6$ with the proviso that $Z_1$ and $R_6$ are not identical, or $Z_1$ is $C_3$–$C_{12}$cycloalkyl which is unsubstituted or substituted by $C_1$–$C_{20}$alkyl, $OR_{11}$, $CF_3$ or halogen; $C_2$–$C_{12}$alkenyl, or $C_3$–$C_{12}$cycloalkenyl, or $Z_1$ is one of the radicals (g), (h), (i), (k), (l), (m), (n), (o), (p), (q), (t), (u), (v) or (w); $Z_2$ is $C_1$–$C_{18}$alkylene; $C_2$–$C_{12}$alkylene interrupted once or more than once by O, S, or $NR_{14}$; $C_2$–$C_{12}$alkenylene; $C_2$–$C_{12}$alkenylene interrupted once or more than once by O, S, or $NR_{14}$; $C_3$–$C_{12}$Cycloalkylene; $C_3$–$C_{12}$cycloalkylene interrupted once or more than once by O, S, or $NR_{14}$; $C_3$–$C_{12}$cycloalkenylene; $C_3$–$C_{12}$cycloalkenylene interrupted once or more than once by O, S, or $NR_{14}$; where the radicals $C_1$–$C_{18}$alkylene, $C_2$–$C_{12}$alkylene, $C_2$–$C_{12}$alkenylene, $C_3$–$C_{12}$cycloalkylene and $C_3$–$C_{12}$cycloalkenylene are unsubstituted or substituted by $OR_{11}$, $SR_{11}$, $N(R_{12})(R_{13})$ and/or halogen; or $Z_2$ is one of the radicals

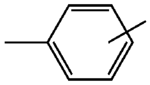

,

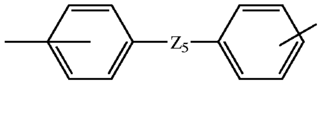

or

-continued

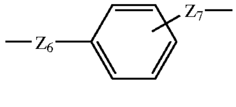

, where these radicals are unsubstituted or substituted on the aromatic by $C_1$–$C_{12}$alkyl; $C_2$–$C_{12}$alkyl, which is interrupted once or more than once by nonconsecutive O atoms and which is unsubstituted or substituted by OH and/or SH; $OR_{11}$, $SR_{11}$, $N(R_{12})(R_{13})$, phenyl, halogen, $NO_2$, CN, (CO)—$OR_{18}$, (CO)—$R_{18}$, (CO)—$N(R_{18})_2$, $SO_2R_{24}$, and/or $CF_3$; or $Z_2$ is a group (r); $Z_3$ is $CH_2$, $CHCH_3$ or $C(CH_3)_2$; $Z_4$ is S, O, $CH_2$, C═O, $NR_{14}$ or a direct bond; $Z_5$ is S, O, $CH_2$, $CHCH_3$, $C(CH_3)_2$, $C(CF_3)_2$, SO, $SO_2$; $Z_6$ and $Z_7$ independently of one another are $CH_2$, $CHCH_3$ or $C(CH_3)_2$; r is 0, 1 or 2; s is a number from 1 to 12; q is a number from 0 to 50; t and p are each numbers from 0 to 20; E, G, $G_3$ and $G_4$ independently of one another are $C_1$–$C_{12}$alkyl, or phenyl which is unsubstituted or substituted by one or more $C_1$–$C_4$alkyl; $R_{14}$ is hydrogen, phenyl, $C_1$–$C_4$alkyl or $C_1$–$C_4$alkoxy; $R_{19}$, $R_{20}$, $R_{21}$, $R_{22}$ and $R_{23}$ have one of the meanings given for $R_6$ or are $NO_2$, CN, $SO_2R_{24}$, $CF_3$, or halogen; $R_{24}$ is $C_1$–$C_{12}$alkyl, halogen-substituted $C_1$–$C_{12}$alkyl, phenyl, or $OR_{11}$- and/or $SR_{11}$-substituted phenyl.

Preferred $R_6$ are as given above for formula I.

$R_{12}$ and $R_{13}$ in the compounds of the formula III are preferably $C_1$–$C_4$alkyl, $C_1$–$C_4$alkoxy or $R_{12}$ and $R_{13}$ together form a morpholino ring.

Also of interest are compounds of the formula III, in which Ar is a group

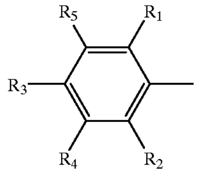

,

A is O; and x is 1; $R_1$ and $R_2$ independantly of one another are $C_1$–$C_4$alkyl, $C_1$–$C_4$alkoxy, $CF_3$ or halogen; $R_3$, $R_4$ and $R_5$ independently of one another are hydrogen, $C_1$–$C_4$alkyl, $C_1$–$C_4$alkoxy or chlorine; $R_6$ is $C_1$–$C_{12}$alkyl unsubstituted or substituted by $OR_{11}$, cycloalkenyl, CN, $C(O)R_{11}$, C(O)$OR_{11}$, $C(O)N(R_{14})_2$, phenyl, cycloalkyl; $C_2$–$C_{12}$alkyl which is interrupted once or more than once by nonconsecutive O, S or $NR_{14}$ and which is unsubstituted or substituted by $OR_{11}$, $SR_{11}$, $N(R_{12})(R_{13})$, CN, $C(O)R_{11}$, $C(O)OR_{11}$ and/or C(O)N$(R_{14})_2$; $C_2$–$C_{12}$alkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$; benzyl, cyclopentyl, cyclohexyl, $C_4$–$C_{12}$cycloalkyl which is uninterrupted or interrupted once or more than once by O, S and/or $NR_{14}$; or $C_8$–$C_{12}$arylcycloalkyl; $R_{11}$ is H, $C_1$–$C_8$alkyl, cyclopentyl, cyclohexyl, phenyl, benzyl or $C_2$–$C_6$alkyl which is interrupted once or twice by nonconsecutive O atoms and which is unsubstituted or substituted by OH; $R_{12}$ and $R_{13}$ independently of one another are hydrogen, $C_1$–$C_4$alkyl, cyclopentyl, cyclohexyl, phenyl, benzyl or $C_2$–$C_6$alkyl which is interrupted once or twice by O and which is unsubstituted or substituted by OH; or $R_{12}$ and $R_{13}$ together are morpholino; $Z_1$ has the same meaning as $R_6$ with the proviso that $Z_1$ and $R_6$ are not identical; or $Z_1$ is one of the radicals (g), (h), (i), (k), (l), (m), (n), (o), (p), (q), (t), (u), (v) or (w); $Z_2$ is $C_1$–$C_{12}$alkylene; $C_2$–$C_{12}$alkylene interrupted once or more than once by O; $C_2$–$C_{12}$alkenylene; $C_2$–$C_{12}$alkenylene interrupted once or more than once by O; $C_5$–$C_8$cycloalkylene; $C_3$–$C_5$cycloalkylene interrupted by O, S, or $NR_{14}$; $C_5$–$C_8$cycloalkenylene; $C_3$–$C_5$cycloalkenylene interrupted by O, S, or $NR_{14}$; where the radicals $C_1$–$C_{12}$alkylene, $C_2$–$C_{12}$alkylene, $C_2$–$C_{12}$alkenylene, $C_5$–$C_8$cycloalkylene and $C_3$–$C_8$cycloalkenylene are unsubstituted or substituted by $OR_{11}$; or $Z_2$ is one of the radicals

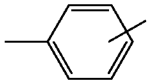

,

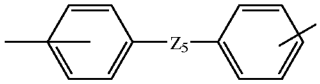

or

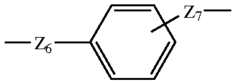

, where these radicals are unsubstituted or substituted on the aromatic by $C_1$–$C_4$alkyl, $OR_{11}$, phenyl, (CO)—$OR_{18}$, (CO)—$R_{18}$ and/or (CO)—$N(R_{18})_2$; or $Z_2$ is a group (r); $Z_3$ is $CH_2$, $CHCH_3$ or $C(CH_3)_2$; $Z_4$ is S, O, $CH_2$, C═O, $NR_{14}$ or a direct bond; $Z_5$ is O, $CH_2$, $CHCH_3$, $C(CH_3)_2$, $C(CF_3)_2$; $Z_6$ and $Z_7$ independently of one another are $CH_2$, $CHCH_3$ or $C(CH_3)_2$; r is 0, 1 or 2; s is a number from 1 to 12; q is a number from 0 to 50; t and p in each case are a number from 0 to 20; E, G, $G_3$ and $G_4$ independently of one another are $C_1$–$C_{12}$alkyl, or phenyl which is unsubstituted or substituted by one or more $C_1$–$C_4$alkyl; $R_{14}$ is hydrogen, phenyl or $C_1$–$C_4$alkyl.

Examples of compounds of the formula III according to the invention are 2,4,6-trimethylbenzoyl-n-butylmethylphosphine oxide, 2,4,6-trimethylbenzoyl-n-butylethylphosphine oxide, 2,4,6-trimethylbenzoyl-n-butylpropylphosphine oxide, 2,4,6-trimethylbenzoyl-di(n-butyl)phosphine oxide, 2,4,6-trimethylbenzoyl-n-butylpentylphosphine oxide, 2,4,6-trimethylbenzoyl-n-butylhexylphosphine oxide, 2,4,6-trimethylbenzoyl-n-butylheptyl phosphine oxide, 2,4,6-trimethylbenzoyl-n-butyyoctylphosphine oxide, 2,4,6-trimethylbenzoyl-n-butyldodecylphosphine oxide, 2,4,6-trimethylbenzoyl-n-butylisopropylphosphine oxide, 2,4,6-trimethylbenzoyl-n-butylisobutylphosphine oxide, 2,4,6-trimethylbenzoyl-n-butylamyl phosphine oxide, (2,4,6-trimethylbenzoyl)-n-butyl-(2-ethylhexyl)phosphine oxide, (2,4,6-trimethylbenzoyl)-(n-butyl)-(tert.-butyl)phosphine oxide, (2,4,6-trimethylbenzoyl)-n-butyl-(1-methylpropyl) phosphine oxide, 2,4,6-trimethylbenzoyl-n-butylisopentylphosphine oxide, 2,4,6-trimethylbenzoyl-n-butylmethoxyethoxyphosphine oxide, 2,4,6-trimethylbenzoyl-n-butylbenzyl phosphine oxide, (2,4,6-trimethylbenzoyl)-n-butyl-(2,4,4-trimethylpentyl)phosphine oxide, (2,4,6-trimethylbenzoyl)-n-butyl-(2-propionic methyl ester)phosphine oxide, (2,4,6-trimethylbenzoyl)-n-butyl-(2-propionic ethyl ester)phosphine oxide, (2,4,6-trimethylbenzoyl)-n-butyl-(2-propionic propyl ester) phosphine oxide, (2,4,6-trimethylbenzoyl)-n-butyl-(2-propionic butyl ester)phosphine oxide, (2,4,6-trimethylbenzoyl)-n-butyl-(2-propionic pentyl ester) phosphine oxide, (2,4,6-trimethylbenzoyl)-n-butyl-(2-propionic hexyl ester)phosphine oxide, (2,4,6-trimethylbenzoyl)-n-butyl-(2-propionic octyl ester) phosphine oxide, (2,4,6-trimethylbenzoyl)-n-butyl-(2-propionic decyl ester) phosphine oxide, (2,4,6-trimethylbenzoyl)-n-butyl-(2-propionic dodecyl ester)

phosphine oxide, (2,4,6-trimethylbenzoyl)-n-butyl-(2-propionic isopropyl ester)phosphine oxide, (2,4,6-trimethylbenzoyl)-n-butyl-(2-propionic isobutyl ester) phosphine oxide, (2,4,6-trimethylbenzoyl)-n-butyl-(2-propionic amyl ester)phosphine oxide, (2,4,6-trimethylbenzoyl)-n-butyl-(2-propionic-2-ethylhexyl ester) phosphine oxide, (2,4,6-trimethylbenzoyl)-n-butyl-(2-propionic-tert-butyl ester)phosphine oxide, (2,4,6-trimethylbenzoyl)-n-butyl-(2-propionic 1-methylpropyl ester)phosphine oxide, (2,4,6-trimethylbenzoyl)-n-butyl-(2-propionic isopentyl ester)phosphine oxide, (2,4,6-trimethylbenzoyl)-n-butyl-(2-propionic methoxyethoxy ester)phosphine oxide, (2,4,6-trimethylbenzoyl)-n-butyl-(2-propionic benzyl ester)phosphine oxide, (2,4,6-trimethylbenzoyl)-n-butyl-(2-propionic 2,4,4-trimethylpentyl ester)phosphine oxide, 2,4,6-trimethylbenzoyl-n-butylacetic methyl ester phosphine oxide, 2,4,6-trimethylbenzoyl-n-butylacetic ethyl ester phosphine oxide, 2,4,6-trimethylbenzoyl-n-butylacetic propyl ester phosphine oxide, 2,4,6-trimethylbenzoyl-n-butylacetic butyl ester phosphine oxide, 2,4,6-trimethylbenzoyl-n-butylacetic pentyl ester phosphine oxide, 2,4,6-trimethylbenzoyl-n-butylacetic hexyl ester phosphine oxide, 2,4,6-trimethylbenzoyl-n-butylacetic octyl ester phosphine oxide, 2,4,6-trimethylbenzoyl-n-butylacetic decyl ester phosphine oxide, 2,4,6-trimethylbenzoyl-n-butylacetic dodecyl ester phosphine oxide, 2,4,6-trimethylbenzoyl-n-butylacetic isopropyl ester phosphine oxide, 2,4,6-trimethylbenzoyl-n-butylacetic isobutyl ester phosphine oxide, 2,4,6-trimethylbenzoyl-n-butylacetic amyl ester phosphine oxide, (2,4,6-trimethylbenzoyl)-n-butyl (acetic 2-ethylhexyl ester)phosphine oxide, (2,4,6-trimethylbenzoyl)-n-butyl(acetic tert-butyl ester phosphine oxide, (2,4,6-trimethylbenzoyl)-n-butylacetic 1-methylpropyl ester)phosphine oxide, 2,4,6-trimethylbenzoyl-n-butylacetic isopentyl ester phosphine oxide, 2,4,6-trimethylbenzoyl-n-butylacetic methoxyethoxy ester phosphine oxide, 2,4,6-trimethylbenzoyl-n-butylacetic benzyl ester phosphine oxide, (2,4,6-trimethylbenzoyl)-n-butyl(acetic 2,4,4-trimethylpentyl ester)phosphine oxide, 2,6-dimethoxybenzoyl-n-butylmethylphosphine oxide, 2,6-dimethoxybenzoyl-n-butylethylphosphine oxide, 2,6-dimethoxybenzoyl-butyl-propylphosphine oxide, 2,6-dimethoxybenzoyl-i-n-butylphosphine oxide, 2,6-dimethoxybenzoyl-n-butylpentylphosphine oxide, 2,6-dimethoxybenzoyl-n-butylhexylphosphine oxide, 2,6-dimethoxybenzoyl-n-butylheptylphosphine oxide, 2,6-dimethoxybenzoyl-n-butyloctylphosphine oxide, 2,6-dimethoxybenzoyl-n-butyldodecylphosphine oxide, 2,6-dimethoxybenzoyl-n-butylisopropylphosphine oxide, 2,6-dimethoxybenzoyl-n-butylisobutylphosphine oxide, 2,6-dimethoxybenzoyl-n-butylamylphosphine oxide, (2,6-dimethoxybenzoyl)-n-butyl-(2-ethylhexyl)phosphine oxide, 2,6-dimethoxybenzoyl-n-butyl-tert-butylphosphine oxide, (2,6-dimethoxybenzoyl)-n-butyl-(1-methylpropyl) phosphine oxide, 2,6-dimethoxybenzoyl-n-butylisopentylphosphine oxide, 2,6-dimethoxybenzoyl-n-butylmethoxyethoxyphosphine oxide, 2,6-dimethoxybenzoyl-n-butylbenzylphosphine oxide, (2,6-dimethoxybenzoyl)-n-butyl-(2,4,4-trimethylpentyl) phosphine oxide, (2,6-dimethoxybenzoyl)-n-butyl-(2-propionic methyl ester)phosphine oxide, (2,6-dimethoxybenzoyl)-n-butyl-(2-propionic ethyl ester) phosphine oxide, (2,6-dimethoxybenzoyl)-n-butyl-(2-propionic propyl ester)phosphine oxide, (2,6-dimethoxybenzoyl)-n-butyl-(2-propionic butyl ester) phosphine oxide, (2,6-dimethoxybenzoyl)-n-butyl-(2-propionic pentyl ester)phosphine oxide, (2,6-dimethoxybenzoyl)-n-butyl-(2-propionic hexyl ester)phosphine oxide, (2,6-dimethoxybenzoyl)-n-butyl-(2-propionic octyl ester) phosphine oxide, (2,6-dimethoxybenzoyl)-n-butyl-(2-propionic decyl ester)phosphine oxide, (2,6-dimethoxybenzoyl)-n-butyl-(2-propionic dodecyl ester) phosphine oxide, (2,6-dimethoxybenzoyl)-n-butyl-(2-propionic isopropyl ester)phosphine oxide, (2,6-dimethoxybenzoyl)-n-butyl-(2-propionic isobutyl ester) phosphine oxide, (2,6-dimethoxybenzoyl)-n-butyl-(2-propionic amyl ester)phosphine oxide, (2,6-dimethoxybenzoyl)-n-butyl-(2-propionic 2-ethylhexyl ester) phosphine oxide, (2,6-dimethoxybenzoyl)-n-butyl-(2-propionic tert-butyl ester)phosphine oxide, (2,6-dimethoxybenzoyl)-n-butyl-(2-propionic 1-methylpropyl ester)phosphine oxide, (2,6-dimethoxybenzoyl)-n-butyl-(2-propionic isopentyl ester)phosphine oxide, (2,6-dimethoxybenzoyl)-n-butyl-(2-propionic methoxyethoxy ester)phosphine oxide, (2,6-dimethoxybenzoyl)-n-butyl-(2-propionic benzyl ester)phosphine oxide, (2,6-dimethoxybenzoyl)-n-butyl-(2-propionic 2,4,4-trimethylpentyl ester)phosphine oxide, 2,6-dimethoxybenzoyl-n-butylacetic methyl ester phosphine oxide, 2,6-dimethoxybenzoyl-n-butylacetic ethyl ester phosphine oxide, 2,6-dimethoxybenzoyl-n-butylacetic propyl ester phosphine oxide, 2,6-dimethoxybenzoyl-n-butylacetic butyl ester phosphine oxide, 2,6-dimethoxybenzoyl-n-butylacetic pentyl ester phosphine oxide, 2,6-dimethoxybenzoyl-n-butylacetic hexyl ester phosphine oxide, 2,6-dimethoxybenzoyl-n-butylacetic octyl ester phosphine oxide, 2,6-dimethoxybenzoyl-n-butylacetic decyl ester phosphine oxide, 2,6-dimethoxybenzoyl-n-butylacetic dodecyl ester phosphine oxide, 2,6-dimethoxybenzoyl-n-butylacetic isopropyl ester phosphine oxide, 2,6-dimethoxybenzoyl-n-butylacetic isobutyl ester phosphine oxide, 2,6-dimethoxybenzoyl-n-butylacetic amyl ester phosphine oxide, (2,6-dimethoxybenzoyl)-n-butyl(acetic 2-ethylhexyl ester)phosphine oxide, 2,6-dimethoxybenzoyl-n-butyl(acetic tert-butyl ester)phosphine oxide, (2,6-dimethoxybenzoyl)-n-butyl(acetic 1-methylpropyl ester) phosphine oxide, 2,6-dimethoxybenzoyl-n-butylacetic isopentyl ester phosphine oxide, 2,6-dimethoxybenzoyl-n-butylacetic methoxyethoxy ester phosphine oxide, 2,6-dimethoxybenzoyl-n-butylacetic benzyl ester phosphine oxide, (2,6-dimethoxybenzoyl)-n-butyl(acetic 2,4,4-trimethylpentyl ester)phosphine oxide, (2,4,6-trimethylbenzoylisobutylmethylphosphine oxide, 2,4,6-trimethylbenzoylisobutylethylphosphine oxide, 2,4,6-trimethylbenzoylisobutylpropylphosphine oxide, 2,4,6-trimethylbenzoylisobutyl-(n-butyl)phosphine oxide, 2,4,6-trimethylbenzoylisobutylpentylphosphine oxide, 2,4,6-trimethylbenzoylisobutylhexylphosphine oxide, 2,4,6-trimethylbenzoylisobutylheptylphosphine oxide, 2,4,6-trimethylbenzoylisobutyloctylphosphine oxide, 2,4,6-trimethylbenzoylisobutyldodecylphosphine oxide, 2,4,6-trimethylbenzoylisobutylisopropylphosphine oxide, 2,4,6-trimethylbenzoyl-di-isobutylphosphine oxide, 2,4,6-trimethylbenzoylisobutylamylphosphine oxide, (2,4,6-trimethylbenzoyl)isobutyl-(2-ethylhexyl)phosphine oxide, 2,4,6-trimethylbenzoylisobutyl(tert-butyl)phosphine oxide, (2,4,6-trimethylbenzoyl)isobutyl-(1-methylpropyl) phosphine oxide, 2,4,6-trimethylbenzoylisobutylisopentylphosphine oxide, 2,4,6-trimethylbenzoylisobutylmethoxyethoxyphosphine oxide, 2,4,6-trimethylbenzoylisobutylbenzylphosphine oxide, (2,4,6-trimethylbenzoyl)isobutyl-(2,4,4-trimethylpentyl) phosphine oxide, 2,4,6-trimethylbenzoyl)isobutyl-(2- propionic methyl ester)phosphine oxide, (2,4,6-trimethylbenzoyl)isobutyl-(2-propionic ethyl ester) phosphine oxide, (2,4,6-trimethylbenzoyl)isobutyl(2-propionic propyl ester)phosphine oxide, (2,4,6-trimethylbenzoyl)isobutyl-(2-propionic butyl ester) phosphine oxide, (2,4,6-trimethylbenzoyl)isobutyl-(2-propionic pentyl ester)phosphine oxide, (2,4,6-trimethylbenzoyl)isobutyl-(2-propionic hexyl ester) phosphine oxide, (2,4,6-trimethylbenzoyl)isobutyl-(2-propionic octyl ester)phosphine oxide, (2,4,6-trimethylbenzoyl)isobutyl-(2-propionic decyl ester) phosphine oxide, (2,4,6-trimethylbenzoyl)isobutyl(2-propionic dodecyl ester)phosphine oxide, (2,4,6-trimethylbenzoyl)isobutyl-(2-propionic isopropyl ester) phosphine oxide, (2,4,6-trimethyl benzoyl)isobutyl-(2-propionic isobutyl ester) phosphine oxide, (2,4,6-trimethylbenzoyl)isobutyl-(2-propionic amyl ester) phosphine oxide, (2,4,6-trimethylbenzoyl)isobutyl-(2-propionic 2-ethyahexyl ester)phosphine oxide, (2,4,6-trimethylbenzoyl)isobutyl-(2-propionic tert-butyl ester) phosphine oxide, (2,4,6-trimethylbenzoyl)isobutyl-(2-propionic 1-methylpropyl ester)phosphine oxide, (2,4,6-trimethylbenzoyl)isobutyl-(2-propionic isopentyl ester) phosphine oxide, (2,4,6-trimethylbenzoyl)isobutyl-(2-propionic methoxyethoxy ester)phosphine oxide, (2,4,6-trimethylbenzoyl)isobutyl-(2-propionic benzyl ester) phosphine oxide, (2,4,6-trimethylbenzoyl)isobutyl-(2-propionic 2,4,4-trimethylpentyl ester)phosphine oxide, 2,4,6-trimethylbenzoylisobutylacetic methyl ester phosphine oxide, 2,4,6-trimethylbenzoylisobutylacetic ethyl ester phosphine oxide, 2,4,6-trimethylbenzoylisobutylacetic propyl ester phosphine oxide, 2,4,6-trimethylbenzoylisobutylacetic butyl ester phosphine oxide, 2,4,6-trimethylbenzoylisobutylacetic pentyl ester phosphine oxide, 2,4,6-trimethylbenzoylisobutylacetic hexyl ester phosphine oxide, 2,4,6-trimethylbenzoylisobutylacetic octyl ester phosphine oxide, 2,4,6-trimethylbenzoylisobutylacetic decyl ester phosphine oxide, 2,4,6-trimethylbenzoylisobutylacetic dodecyl ester phosphine oxide, 2,4,6-trimethylbenzoylisobutylacetic isopropyl ester phosphine oxide, 2,4,6-trimethylbenzoylisobutylacetic isobutyl ester phosphine oxide, 2,4,6-trimethylbenzoylisobutylacetic amyl ester phosphine oxide, (2,4,6-trimethylbenzoyl)isobutyl(acetic 2-ethylhexyl ester) phosphine oxide, (2,4,6-trimethylbenzoyl)isobutyl(acetic tert-butyl ester)phosphine oxide, (2,4,6-trimethylbenzoyl) isobutyl(acetic 1-methylpropyl ester)phosphine oxide, 2,4,6-trimethylbenzoylisobutylacetic isopentyl ester phosphine oxide, 2,4,6-trimethylbenzoylisobutylacetic methoxyethoxy ester phosphine oxide, 2,4,6-trimethylbenzoylisobutylacetic benzyl ester phosphine oxide, (2,4,6-trimethylbenzoyl) isobutyl(acetic 2,4,4-trimethylpentyl ester)phosphine oxide, 2,6-dimethoxybenzoylisobutylmethylphosphine oxide, 2,6-dimethoxybenzoylisobutylethylphosphine oxide, 2,6-dimethoxybenzoylisobutylpropylphosphine oxide, 2,6-dimethoxybenzoylisobutyl-(n-butyl)phosphine oxide, 2,6-dimethoxybenzoylisobutylpentylphosphine oxide, 2,6-dimethoxybenzoylisobutylhexylphosphine oxide, 2,6-dimethoxybenzoylisobutylheptylphosphine oxide, 2,6-dimethoxybenzoylisobutyloctylphosphine oxide, 2,6-dimethoxybenzoylisobutyldodecylphosphine oxide, 2,6-dimethoxybenzoylisobutylisopropylphosphine oxide, 2,6-dimethoxybenzoyldi-isobutylphosphine oxide, 2,6-dimethoxybenzoylisobutylamylphosphine oxide, (2,6-dimethoxybenzoyl)isobutyl-(2-ethylhexyl)phosphine oxide, 2,6-dimethoxybenzoylisobutyl(tert-butyl)phosphine oxide, (2,6-dimethoxybenzoyl)isobutyl-(1-methylpropyl) phosphine oxide, 2,6-dimethoxybenzoylisobutylisopentylphosphine oxide, 2,6-dimethoxybenzoylisobutylmethoxyethoxyphosphine oxide, 2,6-dimethoxybenzoylisobutylbenzylphosphine oxide, (2,6-dimethoxybenzoyl)isobutyl-(2,4,4-trimethylpentyl) phosphine oxide, (2,6-dimethoxybenzoyl)isobutyl-(2-propionic methyl ester)phosphine oxide, (2,6-dimethoxybenzoyl)isobutyl-(2-propionic ethyl ester) phosphine oxide, (2,6-dimethoxybenzoyl)isobutyl-(2-propionic propyl ester)phosphine oxide, (2,6-dimethoxybenzoyl)isobutyl-(2-propionic butyl ester) phosphine oxide, (2,6-dimethoxybenzoyl)isobutyl-(2-propionic pentyl ester) phosphine oxide, (2,6-dimethoxybenzoyl)isobutyl-(2-propionic hexyl ester) phosphine oxide, (2,6-dimethoxybenzoyl)isobutyl-(2-propionic octyl ester)phosphine oxide, (2,6-dimethoxybenzoyl)isobutyl-(2-propionic decyl ester) phosphine oxide, (2,6-dimethoxybenzoyl)isobutyl-(2-propionic dodecyl ester)phosphine oxide, (2,6-dimethoxybenzoyl)isobutyl-(2-propionic isopropyl ester) phosphine oxide, (2,6-dimethoxybenzoyl)isobutyl-(2-propionic isobutyl ester)phosphine oxide, (2,6-dimethoxybenzoyl)isobutyl-(2-propionic amyl ester) phosphine oxide, (2,6-dimethoxybenzoyl)isobutyl-(2-propionic 2-ethylhexyl ester)phosphine oxide, (2,6-dimethoxybenzoyl)isobutyl-(2-propionic tert-butyl ester) phosphine oxide, (2,6-dimethoxybenzoy)isobutyl-(2-propionic 1-methylpropyl ester)phosphine oxide, (2,6-dimethoxybenzoyl)isobutyl-(2-propionic isopentyl ester) phosphine oxide, (2,6-dimethoxybenzoyl)isobutyl-(2-propionic methoxyethoxy ester)phosphine oxide, (2,6-dimethoxybenzoyl)isobutyl-(2-propionic benzyl ester) phosphine oxide, (2,6-dimethoxybenzoyl)isobutyl-(2-propionic 2,4,4-trimethylpentyl ester)phosphine oxide, 2,6-dimethoxybenzoyl-isobutylacetic methyl ester phosphine oxide, 2,6-dimethoxybenzoylisobutylacetic ethyl ester phosphine oxide, 2,6-dimethoxybenzoylisobutylacetic propyl ester phosphine oxide, 2,6-dimethoxybenzoylisobutylacetic butyl ester phosphine oxide, 2,6-dimethoxybenzoylisobutylacetic pentyl ester phosphine oxide, 2,6-dimethoxybenzoylisobutylacetic hexyl ester phosphine oxide, 2,6-dimethoxybenzoylisobutylacetic octyl ester phosphine oxide, 2,6-dimethoxybenzoylisobutylacetic decyl ester phosphine oxide, 2,6-dimethoxybenzoylisobutylacetic dodecyl ester phosphine oxide, 2,6-dimethoxybenzoylisobutylacetic isopropyl ester phosphine oxide, 2,6-dimethoxybenzoylisobutylacetic isobutyl ester phosphine oxide, 2,6-dimethoxybenzoylisobutylacetic amyl ester phosphine oxide, (2,6-dimethoxybenzoyl)-isobutyl(acetic 2-ethylhexyl ester)phosphine oxide, 2,6-dimethoxybenzoylisobutylacetic tert-butyl ester phosphine oxide, (2,6-dimethoxybenzoyl) isobutyl(acetic 1-methylpropyl ester)phosphine oxide, 2,6-dimethoxybenzoylisobutylacetic isopentyl ester phosphine oxide, 2,6-dimethoxybenzoylisobutylacetic methoxyethoxy ester phosphine oxide, 2,6-dimethoxybenzoylisobutylacetic benzyl ester phosphine oxide, (2,6-dimethoxybenzoyl) isobutyl(acetic 2,4,4-trimethylpentyl ester)phosphine oxide, (2,4,6-trimethylbenzoyl)-(2,4,4-trimethylpentyl) methylphosphine oxide, (2,4,6-trimethylbenzoyl)-(2,4,4-trimethylpentyl)ethylphosphine oxide, (2,4,6-trimethylbenzoyl)-(2,4,4-trimethylpentyl)propylphosphine oxide, (2,4,6-trimethylbenzoyl)-(2,4,4-trimethylpentyl) butylphosphine oxide, (2,4,6-trimethylbenzoyl)-(2,4,4-trimethylpentyl)pentylphosphine oxide, (2,4,6-trimethylbenzoyl)-(2,4,4-trimethylpentyl)hexylphosphine oxide, (2,4,6-trimethylbenzoyl)-(2,4,4-trimethylpentyl)

heptylphosphine oxide, (2,4,6-trimethylbenzoyl)-(2,4,4-trimethylpentyl)octylphosphine oxide, (2,4,6-trimethylbenzoyl)-(2,4,4-trimethylpentyl)dodecylphosphine oxide, (2,4,6-trimethylbenzoyl)-(2,4,4-trimethylpentyl)isopropylphosphine oxide, (2,4,6-trimethylbenzoyl)-(2,4,4-trimethylpentyl)isobutylphosphine oxide, (2,4,6-trimethylbenzoyl)-(2,4,4-trimethylpentyl)-amylphosphine oxide, (2,4,6-trimethylbenzoyl)-(2,4,4-trimethylpentyl)-(2-ethylhexy)phosphine oxide, (2,4,6-trimethylbenzoyl)-(2,4,4-trimethylpentyl)-(tert-butyl)phosphine oxide, (2,4,6-trimethylbenzoyl)-(2,4,4-trimethylpentyl)-(1-methylpropyl)phosphine oxide, (2,4,6-trimethylbenzoyl)-(2,4,4-trimethylpentyl)isopentylphosphine oxide, (2,4,6-trimethylbenzoyl)-(2,4,4-trimethylpentyl)methoxyethoxyphosphine oxide, (2,4,6-trimethylbenzoyl)-(2,4,4-trimethylpentyl)benzylphosphine oxide, (2,4,6-trimethylbenzoyl)-bis(2,4,4-trimethylpentyl)phosphine oxide, (2,4,6-trimethylbenzoyl)-(2,4,4-trimethylpentyl)-(2-propionic methyl ester)phosphine oxide, (2,4,6-trimethylbenzoyl)-(2,4,4-trimethylpentyl)-(2-propionic ethyl ester)phosphine oxide, (2,4,6-trimethylbenzoyl)-(2,4,4-trimethylpentyl)-(2-propionic propyl ester)phosphine oxide, (2,4,6-trimethylbenzoyl)-(2,4,4-trimethylpentyl)-(2-propionic butyl ester)phosphine oxide, (2,4,6-trimethylbenzoyl)-(2,4,4-trimethylpentyl)-(2-propionic pentyl ester)phosphine oxide, (2,4,6-trimethylbenzoyl)-(2,4,4-trimethylpentyl)-(2-propionic hexyl ester)phosphine oxide, (2,4,6-trimethylbenzoyl)-(2,4,4-trimethylpentyl)-(2-propionic octyl ester)phosphine oxide, (2,4,6-trimethylbenzoyl)-(2,4,4-trimethylpentyl)-(2-propionic decyl ester)phosphine oxide, (2,4,6-trimethylbenzoyl)-(2,4,4-trimethylpentyl)-(2-propionic dodecyl ester)phosphine oxide, (2,4,6-trimethylbenzoyl)-(2,4,4-trimethylpentyl)-(2-propionic isopropyl ester)phosphine oxide, (2,4,6-trimethylbenzoyl)-(2,4,4-trimethylpentyl)-(2-propionic isobutyl ester)phosphine oxide, (2,4,6-trimethylbenzoyl)-(2,4,4-trimethylpentyl)-(2-propionic amyl ester)phosphine oxide, (2,4,6-trimethylbenzoyl)-(2,4,4-trimethylpentyl)-(2-propionic 2-ethylhexyl ester)phosphine oxide, (2,4,6-trimethylbenzoyl)-(2,4,4-trimethylpentyl)-(2-propionic tert-butyl ester)phosphine oxide, (2,4,6-trimethylbenzoyl)-(2,4,4-trimethylpentyl)-(2-propionic 1-methylpropyl ester)phosphine oxide, (2,4,6-trimethylbenzoyl)-(2,4,4-trimethylpentyl)-(2-propionic isopentyl ester)phosphine oxide, (2,4,6-trimethylbenzoyl)-(2,4,4-trimethylpentyl)-(2-propionic methoxyethoxy ester)phosphine oxide, (2,4,6-trimethylbenzoyl)-(2,4,4-trimethylpentyl)-(2-propionic benzyl ester)phosphine oxide, (2,4,6-trimethylbenzoyl)-(2,4,4-trimethylpentyl)-(2-propionic 2,4,4-trimethylpentyl ester)phosphine oxide, (2,4,6-trimethylbenzoyl)-(2,4,4-trimethylpentyl)acetic methyl ester phosphine oxide, (2,4,6-trimethylbenzoyl)-(2,4,4-trimethylpentyl)acetic ethyl ester phosphine oxide, (2,4,6-trimethylbenzoyl)-(2,4,4-trimethylpentyl)acetic propyl ester phosphine oxide, (2,4,6-trimethylbenzoyl)-(2,4,4-trimethylpentyl)acetic butyl ester phosphine oxide, (2,4,6-trimethylbenzoyl)-(2,4,4-trimethylpentyl)acetic pentyl ester phosphine oxide, (2,4,6-trimethylbenzoyl)-(2,4,4-trimethylpentyl)-acetic hexyl ester phosphine oxide, (2,4,6-trimethylbenzoyl)-(2,4,4-trimethylpentyl)acetic octyl ester phosphine oxide, (2,4,6-trimethylbenzoyl)-(2,4,4-trimethylpentyl)acetic decyl ester phosphine oxide, (2,4,6-trimethylbenzoyl)-(2,4,4-trimethylpentyl)acetic dodecyl ester phosphine oxide, (2,4,6-trimethylbenzoyl)-(2,4,4-trimethylpentyl)acetic isopropyl ester phosphine oxide, (2,4,6-trimethylbenzoyl)-(2,4,4-trimethylpentyl)acetic isobutyl ester phosphine oxide, (2,4,6-trimethylbenzoyl)-(2,4,4-trimethylpentyl)acetic amyl ester phosphine oxide, (2,4,6-trimethylbenzoyl)-(2,4,4-trimethylpentyl)(acetic 2- ethy hexyl ester) phosphine oxide, (2,4,6-trimethylbenzoyl)-(2,4,4-trimethylpentyl)(acetic tert-butyl ester)phosphine oxide, (2,4,6-trimethylbenzoyl)-(2,4,4-trimethylpentyl)(acetic 1-methyl-propyl ester)phosphine oxide, (2,4,6-trimethylbenzoyl)-(2,4,4-trimethylpentyl)acetic isopentyl ester phosphine oxide, (2,4,6-trimethylbenzoyl)-(2,4,4-trimethylpentyl)acetic methoxy-ethoxy ester phosphine oxide, (2,4,6-trimethylbenzoyl)-(2,4,4-trimethylpentyl)acetic benzyl ester phosphine oxide, (2,4,6-trimethylbenzoyl)-(2,4,4-trimethylpentyl)(acetic 2,4,4-trimethylpentyl ester)phosphine oxide, (2,6-dimethoxybenzoyl)-(2,4,4-trimethylpentyl)methylphosphine oxide, (2,6-dimethoxybenzoyl)-(2,4,4-trimethylpentyl)ethylphosphine oxide, (2,6-dimethoxybenzoyl)-(2,4,4-trimethylpentyl)propylphosphine oxide, (2,6-dimethoxybenzoyl)-(2,4,4-trimethylpentyl)butyl-phosphine oxide, (2,6-dimethoxybenzoyl)-(2,4,4-trimethylpentyl)pentylphosphine oxide, (2,6-dimethoxybenzoyl)-(2,4,4-trimethylpentyl)hexylphosphine oxide, (2,6-dimethoxybenzoyl)-(2,4,4-trimethylpentyl)heptylphosphine oxide, (2,6-dimethoxybenzoyl)-(2,4,4-trimethylpentyl)-octylphosphine oxide, (2,6-dimethoxybenzoyl)-(2,4,4-trimethylpentyl)dodecylphosphine oxide, (2,6-dimethoxybenzoyl)-(2,4,4-trimethylpentyl)isopropylphosphine oxide, (2,6-dimethoxybenzoyl)-(2,4,4-trimethylpentyl)isobutylphosphine oxide, (2,6-dimethoxybenzoyl)-(2,4,4-trimethylpentyl)amylphosphine oxide, (2,6-dimethoxybenzoyl)-(2,4,4-trimethylpentyl)-(2-ethylhexyl)phosphine oxide, (2,6-dimethoxybenzoyl)-(2,4,4-trimethylpentyl)-(tert-butyl)phosphine oxide, (2,6-dimethoxybenzoyl)-(2,4,4-trimethylpentyl)-(1-methylpropyl)phosphine oxide, (2,6-dimethoxybenzoyl)-(2,4,4-trimethylpentyl)isopentylphosphine oxide, (2,6-dimethoxybenzoyl)-(2,4,4-trimethylpentyl)methoxyethoxyphosphine oxide, (2,6-dimethoxybenzoyl)-(2,4,4-trimethylpentyl)benzylphosphine oxide, (2,6-dimethoxybenzoyl)-bis(2,4,4-trimethylpentyl)phosphine oxide, (2,6-dimethoxybenzoyl)-(2,4,4-trimethylpentyl)-(2-propionic methyl ester)phosphine oxide, (2,6-dimethoxybenzoyl)-(2,4,4-trimethylpentyl)-(2-propionic ethyl ester)phosphine oxide, (2,6-dimethoxybenzoyl)-(2,4,4-trimethylpentyl)-(2-propionic propyl ester)phosphine oxide, (2,6-dimethoxybenzoyl)-(2,4,4-trimethylpentyl)-(2-propionic butyl ester)phosphine oxide, (2,6-dimethoxybenzoyl)-(2,4,4-trimethylpentyl)-(2-propionic pentyl ester)phosphine oxide, (2,6-dimethoxybenzoyl)-(2,4,4-trimethylpentyl)-(2-propionic hexyl ester)phosphine oxide, (2,6-dimethoxybenzoyl)-(2,4,4-trimethylpentyl)-(2-propionic octyl ester)phosphine oxide, (2,6-dimethoxybenzoyl)-(2,4,4-trimethylpentyl)-(2-propionic decyl ester)phosphine oxide, (2,6-dimethoxybenzoyl)-(2,4,4-trimethylpentyl)-(2-propionic dodecyl ester)phosphine oxide, (2,6-dimethoxybenzoyl)-(2,4,4-trimethylpentyl)-(2-propionic isopropyl ester)phosphine oxide, (2,6-dimethoxybenzoyl)-(2,4,4-trimethylpentyl)-(2-propionic isobutyl ester)phosphine oxide, (2,6-dimethoxybenzoyl)-(2,4,4-trimethylpentyl)-(2-propionic amyl ester)phosphine oxide, (2,6-dimethoxybenzoyl)-(2,4,4-trimethylpentyl)-(2-propionic 2-ethylhexyl ester)phosphine oxide, (2,6-dimethoxybenzoyl)-(2,4,4-trimethylpentyl)-(2-propionic tert-butyl ester)phosphine oxide, (2,6-dimethoxybenzoyl)-(2,4,4-trimethylpentyl)-(2-propionic 1-methylpropyl ester)phosphine oxide, (2,6-dimethoxybenzoyl)-(2,4,4-trimethylpentyl)-(2-propionic isopentyl ester)phosphine oxide, (2,6-dimethoxybenzoyl)-(2,4,4-trimethylpentyl)-(2- propionic methoxyethoxy ester)phosphine oxide, (2,6-dimethoxybenzoyl)-(2,4,4-trimethylpentyl)-(2-propionic benzyl ester)phosphine oxide, (2,6-dimethoxybenzoyl)-(2,4,4-trimethylpentyl)-(2-propionic 2,4,4-trimethylpentyl ester) phosphine oxide, (2,6-dimethoxybenzoyl)-(2,4,4-trimethylpentyl)acetic methyl ester phosphine oxide, (2,6-dimethoxybenzoyl)-(2,4,4-trimethylpentyl)acetic ethyl ester phosphine oxide, (2,6-dimethoxybenzoyl)-(2,4,4-trimethylpentyl)acetic propyl ester phosphine oxide, (2,6-dimethoxybenzoyl)-(2,4,4-trimethylpentyl)acetic butyl ester phosphine oxide, (2,6-dimethoxybenzoyl)-(2,4,4-trimethylpentyl)acetic pentyl ester phosphine oxide, (2,6-dimethoxybenzoyl)-(2,4,4-trimethylpentyl)acetic hexyl ester phosphine oxide, (2,6-dimethoxybenzoyl)-(2,4,4-trimethylpentyl)acetic octyl ester phosphine oxide, (2,6-dimethoxybenzoyl)-(2,4,4-trimethylpentyl)acetic decyl ester phosphine oxide, (2,6-dimethoxybenzoyl)-(2,4,4-trimethylpentyl)acetic dodecyl ester phosphine oxide, (2,6-dimethoxybenzoyl)-(2,4,4-trimethylpentyl)acetic isopropyl ester phosphine oxide, (2,6-dimethoxybenzoyl)-(2,4,4-trimethylpentyl)acetic isobutyl ester phosphine oxide, (2,6-dimethoxybenzoyl)-(2,4,4-trimethylpentyl)acetic amyl ester phosphine oxide, (2,6-dimethoxybenzoyl)-(2,4,4-trimethylpentyl)(acetic 2-ethylhexyl ester)phosphine oxide, (2,6-dimethoxybenzoyl)-(2,4,4-trimethylpentyl)(acetic tert-butyl ester)phosphine oxide, (2,6-dimethoxybenzoyl)-(2,4,4-trimethylpentyl)(acetic 1-methylpropyl ester)phosphine oxide, (2,6-dimethoxybenzoyl)-(2,4,4-trimethylpentyl) acetic isopentyl ester phosphine oxide, (2,6-dimethoxybenzoyl)-(2,4,4-trimethylpentyl)acetic methoxy-ethoxy ester phosphine oxide, (2,6-dimethoxybenzoyl)-(2,4,4-trimethylpentyl)acetic benzyl ester phosphine oxide, (2,6-dimethoxybenzoyl)-(2,4,4-trimethylpentyl)(acetic 2,4,4-trimethylpentyl ester)phosphine oxide, (2,4,6-trimethylbenzoylcyclopentylmethylphosphine oxide, 2,4,6-trimethylbenzoylcyclopentylethylphosphine oxide, 2,4,6-trimethylbenzoylcyclopentylpropylphosphine oxide, 2,4,6-trimethyl benzoylcyclopentylbutylphosphine oxide, 2,4,6-trimethylbenzoylcyclopentylpentylphosphine oxide, 2,4,6-trimethylbenzoylcyclopentylhexylphosphine oxide, 2,4,6-trimethyl benzoylcyclopentylheptylphosphine oxide, 2,4,6-trimethylbenzoylcyclopentyloctylphosphine oxide, 2,4,6-trimethylbenzoylcyclopentyldodecylphosphine oxide, 2,4,6-trimethylbenzoylcyclopentylisopropyl phosphine oxide, 2,4,6-trimethylbenzoylcyclopentylisobutylphosphine oxide, 2,4,6-trimethylbenzoylcyclopentylamylphosphine oxide, (2,4,6-trimethylbenzoyl)cyclopentyl-(2-ethylhexyl) phosphine oxide, (2,4,6-trimethylbenzoyl)cyclopentyl-(tert-butyl)phosphine oxide, (2,4,6-trimethylbenzoyl) cyclopentyl-(1-methylpropyl)phosphine oxide, 2,4,6-trimethylbenzoylcyclopentylisopentyyphosphine oxide, 2,4,6-trimethylbenzoylcyclopentylmethoxyethoxyphosphine oxide, 2,4,6-trimethylbenzoylcyclopentylbenzyl phosphine oxide, (2,4,6-trimethylbenzoyl)cyclopentyl-(2,4,4-trimethylpentyl)phosphine oxide, (2,4,6-trimethylbenzoyl) cyclopentyl-(2-propionic methyl ester) phosphine oxide, (2,4,6-trimethylbenzoyl)cyclopentyl-(2-propionic ethyl ester)phosphine oxide, (2,4,6-trimethylbenzoyl) cyclopentyl-(2-propionic propyl ester)phosphine oxide, (2,4,6-trimethylbenzoyl)cyclopentyl-(2-propionic butyl ester)phosphine oxide, (2,4,6-trimethylbenzoyl) cyclopentyl-(2-propionic pentyl ester)phosphine oxide, (2,4,6-trimethylbenzoyl)cyclopentyl-(2-propionic hexyl ester) phosphine oxide,(2,4,6-trimethylbenzoyl)cyclopentyl-(2-propionic octyl ester) phosphine oxide, (2,4,6-trimethylbenzoyl)cyclopentyl-(2-propionic decyl ester) phosphine oxide, (2,4,6-trimethylbenzoyl)cyclopentyl-(2-propionic dodecyl ester)phosphine oxide, (2,4,6-trimethylbenzoyl)cyclopentyl-(2-propionic isopropyl ester) phosphine oxide, (2,4,6-trimethylbenzoyl)cyclopentyl-(2-propionic isobutyl ester)phosphine oxide, (2,4,6-trimethylbenzoyl)cyclopentyl-(2-propionic amyl ester) phosphine oxide, (2,4,6-trimethylbenzoyl)cyclopentyl-(2-propionic 2-ethylhexyl ester)phosphine oxide, (2,4,6-trimethylbenzoyl)cyclopentyl-(2-propionic tert-butyl ester) phosphine oxide, (2,4,6-trimethylbenzoyl)cyclopentyl-(2-propionic 1-methylpropyl ester)phosphine oxide, (2,4,6-trimethylbenzoyl)cyclopentyl-(2-propionic isopentyl ester) phosphine oxide, (2,4,6-trimethylbenzoyl)cyclopentyl-(2-propionic methoxyethoxy ester)phosphine oxide, (2,4,6-trimethylbenzoyl)cyclopentyl-(2-propionic benzyl ester) phosphine oxide, (2,4,6-trimethylbenzoyl)cyclopentyl-(2-propionic 2,4,4-trimethylpentyl ester)phosphine oxide, 2,4,6-trimethylbenzoylcyclopentylacetic methyl ester phosphine oxide, 2,4,6-trimethylbenzoylcyclopentylacetic ethyl ester phosphine oxide, 2,4,6-trimethylbenzoylcyclopentylacetic propyl ester phosphine oxide, 2,4,6-trimethylbenzoylcyclopentylacetic butyl ester phosphine oxide, 2,4,6-trimethylbenzoylcyclopentylacetic pentyl ester phosphine oxide, 2,4,6-trimethylbenzoylcyclopentylacetic hexyl ester phosphine oxide, 2,4,6-trimethyl-benzoylcyclopentylacetic octyl ester phosphine oxide, 2,4,6-trimethylbenzoylcyclopentylacetic decyl ester phosphine oxide, 2,4,6-trimethylbenzoylcyclopentylacetic dodecyl ester phosphine oxide, 2,4,6-trimethylbenzoylcyclopentylacetic isopropy ester phosphine oxide, 2,4,6-trimethylbenzoylcyclopentylacetic isobutyl ester phosphine oxide, 2,4,6-trimethylbenzoylcyclopentylacetic amyl ester phosphine oxide, (2,4,6-trimethylbenzoyl)cyclopentyl (acetic 2-ethylhexyl ester)phosphine oxide, 2,4,6-trimethylbenzoylcyclopentyl(acetic tert-butyl ester) phosphine oxide, (2,4,6-trimethylbenzoyl)cyclopentylacetic 1-methylpropyl ester)phosphine oxide, 2,4,6-trimethylbenzoylcyclopentylacetic isopentyl ester phosphine oxide, 2,4,6-trimethylbenzoylcyclopentylacetic methoxyethoxy ester phosphine oxide, 2,4,6-trimethylbenzoylcyclopentylacetic benzyl ester phosphine oxide, (2,4,6-trimethylbenzoyl)cyclopentyl(acetic 2,4,4-trimethylpentyl ester)phosphine oxide, 2,6-dimethoxybenzoylcyclopentylmethylphosphine oxide, 2,6-dimethoxybenzoylcyclopentylethylphosphine oxide, 2,6-dimethoxybenzoylcyclopentylpropylphosphine oxide, 2,6-dimethoxybenzoylcyclopentylbutylphosphine oxide, 2,6-dimethoxybenzoylcyclopentylpentylphosphine oxide, 2,6-dimethoxybenzoylcyclopentylhexylphosphine oxide, 2,6-dimethoxybenzoylcyclopentylheptylphosphine oxide, 2,6-dimethoxybenzoylcyclopentyloctylphosphine oxide, 2,6-dimethoxybenzoylcyclopentyldodecylphosphine oxide, 2,6-dimethoxybenzoylcyclopentylisopropylphosphine oxide, 2,6-dimethoxybenzoylcyclopentylisobutylphosphine oxide, 2,6-dimethoxybenzoylcyclopentylamylphosphine oxide, (2,6-dimethoxybenzoyl)cyclopentyl-(2-ethylhexyl) phosphine oxide, (2,6-dimethoxybenzoyl)cyclopentyl-(tert-butyl)phosphine oxide, (2,6-dimethoxybenzoyl) cyclopentyl-(1-methylpropyl)phosphine oxide, 2,6-dimethoxybenzoylcyclopentylisopentylphosphine oxide, 2,6-dimethoxybenzoylcyclopentylmethoxyethoxyphosphine oxide, 2,6-dimethoxybenzoylcyclopentylbenzylphosphine oxide, (2,6-dimethoxybenzoyl)cyclopentyl-(2,4,4-trimethylpentyl)phosphine oxide, (2,6-dimethoxybenzoyl) cyclopentyl-(2-propionic methyl ester)phosphine oxide, (2,6-dimethoxybenzoyl)cyclopentyl-(2-propionic ethyl ester)phosphine oxide, (2,6-dimethoxybenzoyl)cyclopentyl-(2-propionic propyl ester)phosphine oxide, (2,6-dimethoxybenzoyl)cyclopentyl-(2-propionic butyl ester) phosphine oxide, (2,6-dimethoxybenzoyl)cyclopentyl-(2-propionic pentyl ester)phosphine oxide, (2,6-dimethoxybenzoyl)cyclopentyl-(2-propionic hexyl ester) phosphine oxide, (2,6-dimethoxybenzoyl)cyclopentyl-(2-propionic octyl ester)phosphine oxide, (2,6-dimethoxybenzoyl)cyclopentyl-(2-propionic decyl ester) phosphine oxide, (2,6-dimethoxybenzoyl)cyclopentyl-(2-propionic dodecyl ester) phosphine oxide, (2,6-dimethoxybenzoyl)cyclopentyl-(2-propionic isopropyl ester)phosphine oxide, (2,6-dimethoxybenzoyl)cyclopentyl-(2-propionic isobutyl ester)phosphine oxide, (2,6-dimethoxybenzoyl)cyclopentyl-(2-propionic amyl ester) phosphine oxide, (2,6-dimethoxybenzoyl)cyclopentyl-(2-propionic 2-ethylhexyl ester)phosphine oxide, (2,6-dimethoxybenzoyl)cyclopentyl-(2-propionic tert-butyl ester)phosphine oxide, (2,6-dimethoxybenzoyl)cyclopentyl-(2-propionic 1-methylpropyl ester) phosphine oxide, (2,6-dimethoxybenzoyl)cyclopentyl-(2-propionic isopentyl ester)phosphine oxide, (2,6-dimethoxybenzoyl)cyclopentyl-(2-propionic methoxyethoxy ester)phosphine oxide, (2,6-dimethoxybenzoyl)cyclopentyl-(2-propionic benzyl ester) phosphine oxide, (2,6-dimethoxybenzoyl)cyclopentyl-(2-propionic 2,4,4-trimethylpentyl ester)phosphine oxide, 2,6-dimethoxybenzoylcyclopentyl-acetic methyl ester phosphine oxide, 2,6-dimethoxybenzoylcyclopentylacetic ethyl ester phosphine oxide, 2,6-dimethoxybenzoylcyclopentylacetic propyl ester phosphine oxide, 2,6-dimethoxybenzoylcyclopentylacetic butyl ester phosphine oxide, 2,6-dimethoxybenzoylcyclopentylacetic pentyl ester phosphine oxide, 2,6-dimethoxybenzoylcyclopentylacetic hexyl ester phosphine oxide, 2,6-dimethoxybenzoylcyclopentylacetic octyl ester phosphine oxide, 2,6-dimethoxybenzoylcyclopentylacetic decyl ester phosphine oxide, 2,6-dimethoxybenzoyl-cyclopentylacetic dodecyl ester phosphine oxide, 2,6-dimethoxybenzoylcyclopentylacetic isopropyl ester phosphine oxide, 2,6-dimethoxybenzoylcyclopentylacetic isobutyl ester phosphine oxide, 2,6-dimethoxybenzoylcyclopentylacetic amyl ester phosphine oxide, (2,6-dimethoxybenzoyl)cyclopentyl(acetic 2-ethylhexyl ester)phosphine oxide, (2,6-dimethoxybenzoyl)cyclopentyl(acetic tert-butyl ester) phosphine oxide, (2,6-dimethoxybenzoyl)cyclopentyl(acetic 1-methylpropyl ester)phosphine oxide, 2,6-dimethoxybenzoylcyclopentylacetic isopentyl ester phosphine oxide, 2,6-dimethoxybenzoylcyclopentylacetic methoxyethoxy ester phosphine oxide, 2,6-dimethoxybenzoylcyclopentylacetic benzyl ester phosphine oxide, (2,6-dimethoxybenzoyl)cyclopentyl(acetic 2,4,4-trimethylpentyl ester)phosphine oxide, 2,4,6-trimethylbenzoylcyclohexylmethylphosphine oxide, 2,4,6-trimethylbenzoylcyclohexylethylphosphine oxide, 2,4,6-trimethylbenzoylcyclohexylpropylphosphine oxide, 2,4,6-trimethylbenzoylcyclohexylbutylphosphine oxide, 2,4,6-trimethylbenzoylcyclohexylpentylphosphine oxide, 2,4,6-trimethylbenzoylcyclohexylhexylphosphine oxide, 2,4,6-trimethylbenzoylcyclohexylheptylphosphine oxide, 2,4,6-trimethylbenzoylcyclohexyloctylphosphine oxide, 2,4,6-trimethylbenzoylcyclohexyldodecylphosphine oxide, 2,4,6-trimethylbenzoylcyclohexylisopropylphosphine oxide, 2,4,6-trimethylbenzoylcyclohexylisobutylphosphine oxide, 2,4,6-trimethylbenzoylcyclohexylamylphosphine oxide, (2,4,6-trimethylbenzoyl)cyclohexyl-(2-ethylhexyl)phosphine oxide, (2,4,6-trimethylbenzoyl)cyclohexyl(tert.-butyl) phosphine oxide, (2,4,6-trimethylbenzoyl)cyclohexyl-(1-methylpropyl)phosphine oxide, 2,4,6-trimethylbenzoylcyclohexylisopentylphosphine oxide, 2,4,6-trimethylbenzoylcyclohexylmethoxyethoxyphosphine oxide, 2,4,6-trimethylbenzoylcyclohexylbenzylphosphine oxide, (2,4,6-trimethylbenzoyl)cyclohexyl-(2,4,4-trimethylpentyl)phosphine oxide, (2,4,6-trimethylbenzoyl) cyclohexyl-(2-propionic methyl ester)phosphine oxide, (2,4,6-trimethylbenzoyl)cyclohexyl-(2-propionic ethyl ester) phosphine oxide, (2,4,6-trimethylbenzoyl)cyclohexyl-(2-propionic propyl ester)phosphine oxide, (2,4,6-trimethylbenzoyl)cyclohexyl-(2-propionic butyl ester) phosphine oxide, (2,4,6-trimethylbenzoyl)cyclohexyl-(2-propionic pentyl ester)phosphine oxide, (2,4,6-trimethylbenzoyl)cyclohexyl-(2-propionic hexyl ester) phosphine oxide, (2,4,6-trimethylbenzoyl)cyclohexyl-(2-propionic octyl ester)phosphine oxide, (2,4,6-trimethylbenzoyl)cyclohexyl-(2-propionic decyl ester) phosphine oxide, (2,4,6-trimethyl benzoyl)cyclohexyl-(2-propionic dodecyl ester)phosphine oxide, (2,4,6-trimethylbenzoyl)cyclohexyl-(2-propionic isopropyl ester) phosphine oxide, (2,4,6-trimethylbenzoyl)cyclohexyl-(2-propionic isobutyl ester) phosphine oxide, (2,4,6-trimethylbenzoyl)cyclohexyl-(2-propionic amyl ester) phosphine oxide, (2,4,6-trimethylbenzoyl)cyclohexyl-(2-propionic 2-ethylhexyl ester)phosphine oxide, (2,4,6-trimethylbenzoylcyclohexyl-(2-propionic tert-butyl ester) phosphine oxide, (2,4,6-trimethylbenzoyl)cyclohexyl-(2-propionic 1-methylpropyl ester)phosphine oxide, (2,4,6-trimethylbenzoyl)cyclohexyl-(2-propionic isopentyl ester) phosphine oxide, (2,4,6-trimethylbenzoyl) cyclohexyl-(2-propionic methoxyethoxy ester)phosphine oxide, (2,4,6-trimethylbenzoyl)cyclohexyl-(2-propionic benzyl ester) phosphine oxide, (2,4,6-trimethylbenzoyl)cyclohexyl-(2-propionic 2,4,4-trimethylpentyl ester)phosphine oxide, 2,4,6-trimethylbenzoylcyclohexylacetic methyl ester phosphine oxide, 2,4,6-trimethylbenzoylcyclohexylacetic ethyl ester phosphine oxide, 2,4,6-trimethylbenzoylcyclohexylacetic propyl ester phosphine oxide, 2,4,6-trimethylbenzoylcyclohexylacetic butyl ester phosphine oxide, 2,4,6-trimethylbenzoylcyclohexylacetic pentyl ester phosphine oxide, 2,4,6-trimethylbenzoylcyclohexylacetic hexyl ester phosphine oxide, 2,4,6-trimethylbenzoylcyclohexylacetic octyl ester phosphine oxide, 2,4,6-trimethylbenzoylcyclohexylacetic decyl ester phosphine oxide, 2,4,6-trimethylbenzoylcyclohexylacetic dodecyl ester phosphine oxide, 2,4,6-trimethylbenzoylcyclohexylacetic isopropyl ester phosphine oxide, 2,4,6-trimethylbenzoylcyclohexylacetic isobutyl ester phosphine oxide, 2,4,6-trimethylbenzoylcyclohexylacetic amyl ester phosphine oxide, (2,4,6-trimethylbenzoyl)cyclohexyl(acetic 2-ethylhexyl ester)phosphine oxide, (2,4,6-trimethylbenzoyl)cyclohexyl(acetic tert-butyl ester) phosphine oxide, (2,4,6-trimethylbenzoyl)cyclohexyl(acetic 1-methylpropyl ester)phosphine oxide, 2,4,6-trimethylbenzoylcyclohexylacetic isopentyl ester phosphine oxide, 2,4,6-trimethylbenzoylcyclohexylacetic methoxyethoxy ester phosphine oxide, 2,4,6-trimethylbenzoylcyclohexylacetic benzyl ester phosphine oxide, (2,4,6-trimethylbenzoyl)cyclohexyl(acetic 2,4,4-trimethylpentyl ester)phosphine oxide, 2,6-dimethoxybenzoylcyclohexylmethylphosphine oxide, 2,6-dimethoxybenzoylcyclohexylethylphosphine oxide, 2,6-dimethoxybenzoylcyclohexylpropylphosphine oxide, 2,6-dimethoxybenzoylcyclohexylbutylphosphine oxide, 2,6-dimethoxybenzoylcyclohexylpentylphosphine oxide, 2,6- dimethoxybenzoylcyclohexylhexylphosphine oxide, 2,6-dimethoxybenzoylcyclohexylheptylphosphine oxide, 2,6-dimethoxybenzoylcyclohexyloctylphosphine oxide, 2,6-dimethoxybenzoylcyclohexyldodecylphosphine oxide, 2,6-dimethoxybenzoylcyclohexylisopropylphosphine oxide, 2,6-dimethoxybenzoylcyclohexylisobutylphosphine oxide, 2,6-dimethoxybenzoylcyclohexylamylphosphine oxide, (2,6-dimethoxybenzoyl)cyclohexyl-(2-ethylhexyl)phosphine oxide, (2,6-dimethoxybenzoyl)cyclohexyl-(tert-butyl)phosphine oxide, (2,6-dimethoxybenzoyl)cyclohexyl-(1-methylpropyl)phosphine oxide, 2,6-dimethoxybenzoylcyclohexylisopentylphosphine oxide, 2,6-dimethoxybenzoylcyclohexylmethoxyethoxyphosphine oxide, 2,6-dimethoxybenzoylcyclohexylbenzylphosphine oxide, (2,6-dimethoxybenzoyl)cyclohexyl-(2,4,4-trimethylpentyl)phosphine oxide, (2,6-dimethoxybenzoyl)cyclohexyl-(2-propionic methyl ester)phosphine oxide, (2,6-dimethoxybenzoyl)cyclohexyl-(2-propionic ethyl ester)phosphine oxide, (2,6-dimethoxybenzoyl)cyclohexyl-(2-propionic propyl ester)phosphine oxide, (2,6-dimethoxybenzoyl)cyclohexyl-(2-propionic butyl ester)phosphine oxide, (2,6-dimethoxybenzoyl)cyclohexyl-(2-propionic pentyl ester)phosphine oxide, (2,6-dimethoxybenzoyl)cyclohexyl-(2-propionic hexyl ester)phosphine oxide, (2,6-dimethoxybenzoyl)cyclohexyl-(2-propionic octyl ester)phosphine oxide, (2,6-dimethoxybenzoyl)cyclohexyl-(2-propionic decyl ester)phosphine oxide, (2,6-dimethoxybenzoyl)cyclohexyl-(2-propionic dodecyl ester)phosphine oxide, (2,6-dimethoxybenzoyl)cyclohexyl-(2-propionic isopropyl ester)phosphine oxide, (2,6-dimethoxybenzoyl)cyclohexyl-(2-propionic isobutyl ester)phosphine oxide, (2,6-dimethoxybenzoyl)cyclohexyl-(2-propionic amyl ester)phosphine oxide, (2,6-dimethoxybenzoyl)cyclohexyl-(2-propionic 2-ethylhexyl ester)phosphine oxide, (2,6-dimethoxybenzoyl)cyclohexyl-(2-propionic tert-butyl ester)phosphine oxide, (2,6-dimethoxybenzoyl)cyclohexyl-(2-propionic 1-methylpropyl ester)phosphine oxide, (2,6-dimethoxybenzoyl)cyclohexyl-(2-propionic isopentyl ester)phosphine oxide, (2,6-dimethoxybenzoyl)cyclohexyl-(2-propionic methoxyethoxy ester)phosphine oxide, (2,6-dimethoxybenzoyl)cyclohexyl-(2-propionic benzyl ester)phosphine oxide, (2,6-dimethoxybenzoyl)cyclohexyl-(2-propionic 2,4,4-trimethylpentyl ester)phosphine oxide, 2,6-dimethoxybenzoyl-cyclohexylacetic methyl ester phosphine oxide, 2,6-dimethoxybenzoylcyclohexylacetic ethyl ester phosphine oxide, 2,6-dimethoxybenzoylcyclohexylacetic propyl ester phosphine oxide, 2,6-dimethoxybenzoylcyclohexylacetic butyl ester phosphine oxide, 2,6-dimethoxybenzoylcyclohexylacetic pentyl ester phosphine oxide, 2,6-dimethoxybenzoylcyclohexylacetic hexyl ester phosphine oxide, 2,6-dimethoxybenzoylcyclohexylacetic octyl ester phosphine oxide, 2,6-dimethoxybenzoylcyclohexylacetic decyl ester phosphine oxide, 2,6-dimethoxybenzoylcyclohexylacetic dodecyl ester phosphine oxide, 2,6-dimethoxybenzoylcyclohexylacetic isopropyl ester phosphine oxide, 2,6-dimethoxybenzoylcyclohexylacetic isobutyl ester phosphine oxide, 2,6-dimethoxybenzoylcyclohexylacetic amyl ester phosphine oxide, (2,6-dimethoxybenzoyl)cyclohexyl(acetic 2-ethylhexyl ester)phosphine oxide, (2,6-dimethoxybenzoyl)cyclohexyl(acetic tert-butyl ester)phosphine oxide, (2,6-dimethoxybenzoyl)cyclohexyl(acetic 1-methylpropyl ester)phosphine oxide, 2,6-dimethoxybenzoylcyclohexylacetic isopentyl ester phosphine oxide, 2,6-dimethoxybenzoylcyclohexylacetic methoxyethoxy ester phosphine oxide, 2,6-dimethoxybenzoylcyclohexylacetic benzyl ester phosphine oxide, (2,6-dimethoxybenzoyl)cyclohexyl(acetic 2,4,4-trimethylpentyl ester)phosphine oxide.

The compounds of the formula III are obtained by reaction of a corresponding compound of the formula I with a compound $Z_1$—X (VI), where firstly the compound of the formula III in which x=0 (III') is prepared:

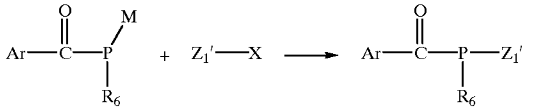

(I) (VI) (III')

Ar, M, X, and $R_6$ are as defined above and in the claims. $Z_1$' has the meanings as given in claim 1, with the exception of the groups (v), (w) and $C_1$–$C_{24}$alkylthio. (The preparation of compounds of the formula III in which $Z_1$ is (v), (w) or $C_1$–$C_{24}$alkylthio is described below.) If compounds of the formula III where A═O or S are to be prepared, an oxidation or sulfurization of the compound of the formula (III') is then carried out, either after the compounds of the formula (III') have been separated off by customary methods, or without isolation thereof. The conditions for such reactions are analogous to those described for the preparation of the compounds of the formula II.

If a compound of the formula (III) in which $Z_1$ is a radical (v)

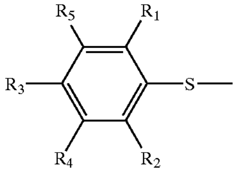

or (w)

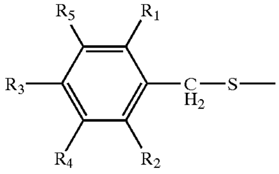

in which $Z_1$ $C_1$–$C_{24}$alkylthio, then the compound of the formula (I) is reacted with a compound of the formula $Z_1$—$SO_2$—X, where, without an intermediate stage, a compound of the formula (III) where A═O and x=1 is directly obtained. ($Z_1$ is defined as above, X is defined as in the claims.) The carrying out of the oxidation step is therefore unnecessary.

Similar reactions are described, for example, in Houben-Weyl, E2, Methoden der Organischen Chemie, 4$^{th}$ edition, pages 222–225.

If compounds of the formula (III) in which $Z_1$ is a radical (v) or (w) or $C_1$–$C_{24}$alkylthio and in which A is sulfur are to be prepared, then it is, for example, possible to convert the corresponding oxide compound as described above into the sulfide. This is possible, for example, by reacting the corresponding phosphine oxide with an excess of $P_2S_5$ or elemental sulfur in a high-boiling solvent. Such reactions, i.e. reactions in which a P═O bond is converted into a P═S bond, are described, for example, in L. Horner et al., Chem. Ber. 92, 2088 (1959) and U.S. Pat. No. 2,642,461. In principle, it is also possible to firstly reduce the corresponding phosphine oxide compound to give the respective phosphine and then to sulfurize the phosphine. I.e. the P═O bond is reduced to give the phosphine using a suitable reducing agent, and is then sulfurized with elemental sulfur to give the P═S bond. Reducing agents which may be used are, for example, $LiAlH_4$, $Ca(AlH_4)_2$, $CaH_2$, $AlH_3$, $SiHCl_3$, $PhSiH_3$ and the agents as described in "Organic Phosphorous Compounds, Wiley-Interscience 1972, Vol. 1, pages 45–46 and Vol.3, pages 408–413".

The invention provides a process for the preparation of compounds of the formula III from the novel starting materials of the formula I, (1) by reaction of an acyl halide of the formula IV

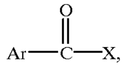

(IV)

in which

Ar is as defined above, and

X is Cl or Br;

with a dimetalated organophosphine of the formula V

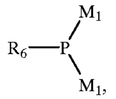

(V)

in which $R_6$ is as defined above; and $M_1$ is Na, Li or K;

in the molar ratio of approximately 1:1;

(2) subsequent reaction of the product with a compound of the formula VI or VI'

$Z_1$═ (VI)

$Z_1$—X' (VI'), in which $Z_1$ is as defined above; and

X is as defined above; and

X' —N═C═A, —N═C═N═$Z_1$,

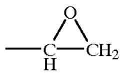

or —CHO;

with the proviso that Z, is not identical to $R_6$;

in the molar ratio of approximately 1:1; and, (3) in the case where $Z_1$ is not a group (v), (w) or $C_1$–$C_{12}$alkylthio and compounds of the formula III in which A is oxygen or sulfur are to be obtained, subsequent oxidation or sulfurization of the resulting phosphine compounds.

The invention also provides a process for the preparation of compounds of the formula III (1) by reaction of an acyl halide of the formula IV

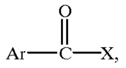

(IV)

in which

Ar is as defined above, and

X is Cl or Br;

with an unsymmetrical phosphine of the formula VII

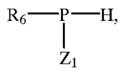

(VII)

in which $R_6$ is as defined above, and $Z_1$ is as defined above with the proviso that $R_6$ and $Z_1$ are not identical;

in the molar ratio of approximately 1:1, in the presence of a base or an organolithium compound, to give the corresponding acylphosphine; and (2) subsequent oxidation or sulfurization of the acylphosphine thus obtained.

This preparation process is novel and likewise provided by the invention.

Suitable bases for this process are, for example, organolithium compounds, such as butyllithium, or organic nitrogen bases, for example tertiary amines or pyridine.

Furthermore, the compounds of the formula III can also be prepared by reacting the compound of the formula I with phosgene, analogous to the description in "W. A. Henderson et al., J. Am. Chem. Soc. 1960, 82, 5794" or "GB 904 086" or in "Organic Phosphorous Compounds, Editors: R. M. Kosolapoff and L. Maier, Wiley-Interscience 1972, Vol.1, page 28" or "Houben-Weyl, Methoden der Organischen Chemie, Vol. XII/1, page 201" to give the corresponding phosphine chloride (Ii). Compounds of the formula (Ii) can, as described in "Organic Phosphorous Compounds, Editors: R. M. Kosolapoff and L. Maier, Wiley-Interscience 1972, Vol.4, pages 268–269", be reacted with alcohols to give compounds of the formula (Iii), which are then directly reacted with an organohalide of the formula VI, in analogy to "K. Sasse in Houben-Weyl, Methoden der Organischen Chemie, Vol XII/1, page 433" (by Michaelis-Arbuzov reaction), to give compounds of the formula III. In this case, the oxidation or sulfurization step is superfluous.

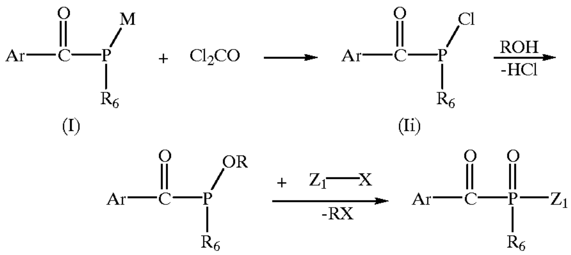

(I) (Ii) (Iii) (III)

Ar are $Z_1$ are as described in claim 1 and 3; X is Cl or Br; $R_6$ and M are likewise defined as in claim 1, and R is any alcohol radical, e.g. $C_1$–$C_{12}$alkyl, $C_5$–$C_8$cycloalkyl, for example cyclopentyl or cyclohexyl, or benzyl.

The reaction conditions for the reaction of the compounds of the formula (I)→formula (Ii)→formula (Iii) are analogous to those described above for the preparation of the compounds of the formula (II) by this process.

The conversion of compounds of the formula (Iii) to compounds of the formula (III) is carried out by adding corresponding alkyl halides ($Z_1$—X) to a solution of compounds of the formula (Iii) in in an inert solvent. Here, the alkyl halide is advantageously dissolved, for example, in the same solvent. The addition is carried out, for example, at a temperature of from 40° C. to 140° C., preferably at 60° C. to 120° C., the lower-boiling alkyl halide (RX) liberated during the reaction advantageously being removed from the reaction solution by distillation. Solvents which may be used are e.g. alkanes, such as hexane, octane; cycloalkanes, such as cyclohexane; ethers, such as tert-butyl methyl ether, tetrahydrofuran, dioxane; or aromatic solvents, such as toluene or xylene. The compounds of the structure (III) are isolated and purified, for example, by distillation under reduced pressure, crystallization or by chromatography.

Compounds of the formula (Iii) can be oxidized using suitable oxidizing agents, such as peroxo acids, hydrogen peroxide or hydrogen peroxide/urea to give the corresponding phosphinic esters (Iiii):

(Iiii)

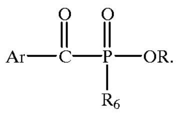

The invention thus also provides a process for the preparation of compounds of the formula III in which A is oxygen and x is 1, by (1) reaction of a compound of the formula (I), (I)

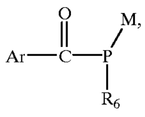

in which

Ar, M and $R_6$ are as defined above, with phosgene to give corresponding phosphine chloride (Ii)

(Ii)

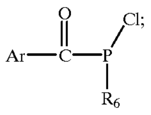

(2) subsequent reaction with an alcohol to give the compound of the formula (Iii)

(Iii)

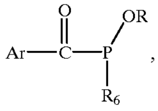

, in which

R is the radical of an alcohol, in particular $C_1$–$C_{12}$alkyl, $C_5$–$C_8$cycloalcyl or benzyl; and (3) reaction of the resulting compound of the formula (Iii) with an organohalide $Z_1$—X, in which $Z_1$ is as defined above, but is not identical to $R_6$ from the formula (I), and X is Cl or Br, to give the compound of the formula III.

It is also conceivable to obtain the compounds of the formula III according to the invention by another method. E.g. processes as described in U.S. Pat. No. 4,298,738 or U.S. Pat. No. 4,324,744 could be used.

The invention provides for the use of compounds of the formula I as starting materials for the preparation of mono- or bisacylphosphines, mono- or bisacylphosphine oxides or mono- or bisacylphosphine sulfides.

Preference is also given to compounds of the formula I, II and III, in which

Ar is a group

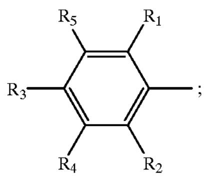

A is O;

x is 1;

$R_1$ and $R_2$ are methyl;

$R_3$ is methyl;

$R_4$ and $R_5$ are hydrogen;

$R_6$ is $C_1$–$C_4$alkyl;

M is Li;

$Z_1$ is a radical (g)

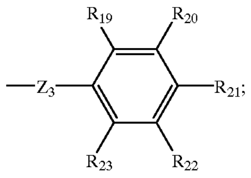

$Z_3$ is $CH_2$; and $R_{19}$, $R_{20}$, $R_{21}$, $R_{22}$ and $R_{23}$ are hydrogen Preference is given, in particular, to compounds of the formula I, II and III (I)

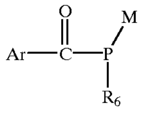

(II)

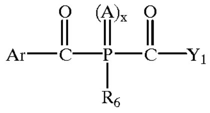

-continued (III)

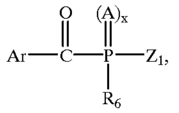

in which

Ar is a group

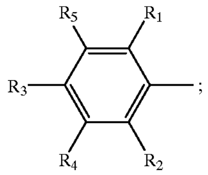

$R_1$ and $R_2$ independently of one another are $C_1$–$C_8$alkyl or $OR_{11}$;

$R_3$, $R_4$ and $R_5$ independently of one another are hydrogen or $C_1$–$C_8$alkyl;

$R_6$ is $C_1$–$C_{12}$alkyl;

$R_{11}$ is H or $C_1$–$C_8$alkyl;

$R_{12}$ and $R_{13}$ independently of one another are hydrogen or $C_1$–$C_8$alkyl;

M is hydrogen or Li;

A is O;

x is 1;

$Y_1$ is $OR_{11}$, $N(R_{12})(R_{13})$ or a radical

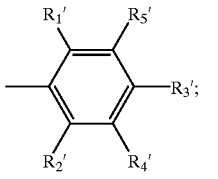

$R_1$' and $R_2$' independently of one another have the same meanings given for $R_1$ and $R_2$; and $R_3$', $R_4$' and $R_5$' independently of one another have the same meanings as given for $R_3$, $R_4$ and $R_5$;

with the proviso that $Y_1$ is not identical to Ar;

$Z_1$ is $C_1$–$C_{12}$alkyl which is unsubstituted or substituted once or more than once by $OR_{15}$, phenyl and/or

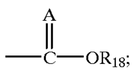

or $Z_1$ is unsubstituted or $OR_{11}$-substituted $C_3$–$C_{24}$cycloalkyl; or $Z_1$ is one of the radicals (g)

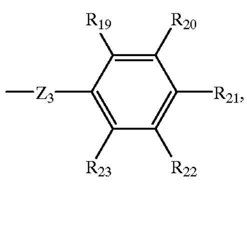

or

-continued (t)

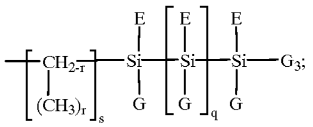

$Z_3$ is $CH_2$ or CH(OH);

r is 0;

s is 1;

E, G and $G_3$ independently of one another are unsubstituted $C_1$–$C_4$alkyl;

$R_{15}$ has one of the meanings given for $R_{11}$;

$R_{18}$ is $C_1$–$C_{12}$alkyl; and $R_{19}$, $R_{20}$, $R_{21}$, $R_{22}$ and $R_{23}$ independently of one another are hydrogen or halogen;

and with the proviso that $R_6$ and $Z_1$ are not identical.

According to the invention, the compounds of the formulae II and III can be used as photoinitiators for the photopolymerization of ethylenically unsaturated compounds or mixtures which comprise such compounds.

This use can also take place in combination with another photoinitiator and/or other additives.

The invention thus also relates to photopolymerizable compositions comprising (a) at least one ethylenically unsaturated photopolymerizable compound and (b) as photoinitiator, at least one compound of the formula II and/or III, where the composition, in addition to the component (b), can also comprise other photoinitiators (c) and/or other additives (d).

Preference is given to using in these compositions compounds of the formula II or III in which x is 1, in particular those compounds in which x is 1 and A is oxygen. Very particular preference is given in such compositions to those compounds of the formula II and III, in which Ar is a group

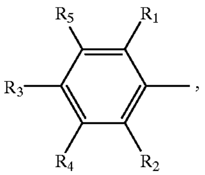

A is oxygen and x is 1.

The unsaturated compounds can contain one or more olefinic double bonds. They can be of low molecular weight (monomeric) or relatively high molecular weight (oligomeric). Examples of monomers with a double bond are alkyl or hydroxyalkyl acrylates or methacrylates, for example methyl acrylate, ethyl acrylate, butyl acrylate, 2-ethylhexyl acrylate or 2-hydroxyethyl acrylate, isobornyl acrylate, methyl methacrylate or ethyl methacrylate. Also of interest are silicon- or fluorine-modified resins, e.g. silicone acrylates. Further examples are acrylonitrile, acrylamide, methacrylamide, N-substituted (meth)acrylamides, vinyl esters, such as vinyl acetate, vinyl ethers, such as isobutyl vinyl ether, styrene, alkyl- and halostyrenes, N-vinylpyrrolidone, vinyl chloride or vinylidene chloride.

Examples of monomers having two or more double bonds are ethylene glycol diacrylate, propylene glycol diacrylate, neopentyl glycol diacrylate, hexamethylene glycol diacrylate or bisphenol A diacrylate, 4,4'-bis(2-acryloyloxyethoxy) diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanu rate or tris(2-acryloylethyl) isocyanurate.

Examples of higher molecular weight (oligomeric) polyunsaturated compounds are acrylicized epoxy resins, polyurethanes, polyethers and polyesters which are acrylicized or contain vinyl ether or epoxy groups. Further examples of unsaturated oligomers are unsaturated polyester resins which are mostly prepared from maleic acid, phthalic acid and one or more diols and have molecular weights of from about 500 to 3,000. In addition, it is also possible to use vinyl ether monomers and oligomers, and maleate-terminated oligomers having polyester, polyurethane, polyether, polyvinyl ether and epoxy main chains. In particular, combinations of oligomers which carry vinyl ether groups and polymers as described in WO 90/01512 are highly suitable. However, copolymers of vinyl ether and maleic acid-functionalized monomers are also suitable. Such unsaturated oligomers may also be referred to as prepolymers.

Examples of particularly suitable compounds are esters of ethylenically unsaturated carboxylic acids and polyols or polyepoxides, and polymers containing ethylenically unsaturated groups in the chain or in side-groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and mixtures of one or more such polymers.

Examples of unsaturated carboxylic acids are acrylic acid, methacrylic acid, crotonic acid, itaconic acid, cinnamic acid, unsaturated fatty acids such as linolenic acid or oleic acid. Preference is given to acrylic acid and methacrylic acid.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on said polyols, particularly aromatic polyols and epichlorohydrins. In addition, polymers and copolymers which contain hydroxyl groups in the polymer chain or in side groups, for example polyvinyl alcohol and copolymers thereof or hydroxyalkyl polymethacrylates or copolymers thereof, are also suitable as polyols. Further suitable polyols are oligoesters containing hydroxyl end-groups.

Examples of aliphatic and cycloaliphatic polyols are alkylenediols having, preferably, 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of, preferably, 200 to 1,500, 1,3-cyclopentanediol, 1,2-, 1,3- or 1,4-cyclohexanediol, 1,4-dihydroxymethylcyclohexane, glycerol, tris(,-hydroxyethyl)amine, trimethylolethane, trimethylolpropane, pentaerythritol, dipentaerythritol and sorbitol.

The polyols may be partially or completely esterified using one or different unsaturated carboxylic acids, where the free hydroxyl groups in partial esters may be modified, e.g. etherified or esterified with other carboxylic acids.

Examples of esters are:

trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and triacrylate, 1,4-cyclohexane diacrylate, bisacrylates and bismethacrylates of polyethylene glycol having molecular weights of from 200 to 1,500, or mixtures thereof.

Also suitable as component (a) are the amides of identical or different unsaturated carboxylic acids of aromatic, cycloaliphatic and aliphatic polyamines having, preferably, 2 to 6, particularly 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)ethane or di(β-aminopropoxy)ethane. Further suitable polyamines are polymers and copolymers with or without additional amino groups in the side chain and oligoamides containing amino end groups. Examples of such unsaturated amides are: methylenebisacrylamide, 1,6-hexamethylenebisacrylamide, diethylenetriaminetrismethacrylamide, bis(methacrylamidopropoxy)ethane, β-methacrylamidoethyl methacrylate, N[(β-hydroxyethoxy)ethyl]acrylamide.

Suitable unsaturated polyesters and polyamides are derived, for example, from maleic acid and diols or diamines. Some of the maleic acid may be replaced by other dicarboxylic acids. They can be used together with ethylenically unsaturated comonomers, e.g. styrene. The polyesters and polyamides may also be derived from dicarboxylic acids and ethylenically unsaturated diols or diamines, particularly from relatively long chain compounds containing, for example, 6 to 20 carbon atoms. Examples of polyurethanes are those constructed from saturated or unsaturated diisocyanates and unsaturated or saturated diols.

Polybutadiene and polyisoprene and copolymers thereof are known. Suitable comonomers are, for example, olefins, such as ethylene, propene, butene, hexene, (meth)acrylates, acrylonitrile, styrene or vinyl chloride. Polymers containing (meth)acrylate groups in the side chain are likewise known. These may, for example, be products of the reaction of novolak-based epoxy resins with (meth)acrylic acid, homo- or copolymers of vinyl alcohol or hydroxyalkyl derivatives thereof which have been esterified using (meth)acrylic acid, or homo- and copolymers of (meth)acrylates which have been esterified using hydroxyalkyl (meth)acrylates.

The photopolymerizable compounds may be used on their own or in any desired mixtures. Preference is given to using mixtures of polyol (meth)acrylates.

It is also possible to add binders to the compositions according to the invention; this is particularly advantageous if the photopolymerizable compounds are liquid or viscose substances. The amount of binder may, for example, be 5–95% by weight, preferably 10–90% by weight and particularly 40–90% by weight, based on the total solids. The binder is chosen depending on the field of application and on the properties required therefore, such as the facility for development in aqueous or organic solvent systems, adhesion to substrates and sensitivity to oxygen.

Examples of suitable binders are polymers having a molecular weight of from about 5,000–2,000,000, preferably 10,000–1,000,000. Examples are: homo- and copolymeric acrylates and methacrylates, e.g. copolymers of methyl methacrylate/ethyl acrylate/methacrylic acid, poly (alkyl methacrylates), poly(alkyl acrylates); cellulose esters and cellulose ethers, such as cellulose acetate, cellulose acetate butyrate, methylcellulose, ethylcellulose; polyvinylbutyral, polyvinylformal, cyclized rubber, polyethers, such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly (ethylene/vinyl acetate), polymers such as polycaprolactam and poly(hexamethyleneadipamide), and polyesters such as poly(ethylene glycol terephthalate) and poly(hexamethylene glycol succinate).

The unsaturated compounds can also be used in mixtures with non-photopolymerizable film-forming components. These may, for example, be physically drying polymers or solutions thereof in organic solvents, for example nitrocellulose or cellulose acetobutyrate. However, they may also be chemically or thermally curable resins, for example polyisocyanates, polyepoxides or melamine resins. The co-use of thermally curable resins is of importance for use in so-called hybrid systems, which are photopolymerized in a first stage and are crosslinked by thermal aftertreatment in a second stage.

The photoinitiators according to the invention are also suitable as initiators for the curing of oxidatively drying systems, as are described, for example, in Lehrbuch der Lacke und Beschichtungen Volume III, 296–328, Verlag W. A. Colomb in Heenemann GmbH, Berlin-Oberschwandorf (1976).

Apart from the photoinitiator, the photopolymerizable mixtures can also contain various additives (d). Examples thereof are thermal inhibitors, which are intended to prevent premature polymerization, for example hydroquinone, hydroquinone derivatives, p-methoxyphenol, β-naphthol or sterically hindered phenols, for example 2,6-di(tert-butyl)-p-cresol. To increase the storage stability in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. In order to exclude atmospheric oxygen during the polymerization, it is possible to add paraffin or similar wax-like substances which migrate to the surface at the start of the polymerization due to their lack of solubility in the polymers, and form a transparent surface layer which prevents the entry of air. It is likewise possible to apply an oxygen-impermeable layer. Light protection agents which may be used are UV absorbers, for example those of the hydroxyphenylbenzotriazol, hydroxyphenylbenzophenone, oxalamide or hydroxyphenyl-s-triazine type. The compounds can be used individually or as mixtures, with or without the use of sterically hindered amines (HALS).

Examples of such UV absorbers and light protection agents are 1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis(α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-yl phenol]; transesterification product of 2-[3'-tert-butyl-5'-(2-methoxycarbonylethyl)-2'-hydroxyphenyl]benzotriazole with polyethylene glycol 300; $[R—CH_2CH_2—COO(CH_2)_3]_2—$ where R=3'-tert-butyl-4'-hydroxy-5'-2H-benzotriazol-2-yl phenyl.

2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

3. Esters of unsubstituted or substituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl and isooctyl α-cyano-β, β-diphenylacrylate, methyl α-carbomethoxycinnamate, methyl and butyl α-cyano-β-methyl-p-methoxycinnamate, methyl α-carbomethoxy-p-methoxycinnamate and N-(β-carbomethoxy-β-cyanovinyl)-2-methylindoline.

5. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the product of the condensation of 1-hydroxyethyl-2,2,6,6-tetramethyl-4-hydroxypiperidine and succinic acid, the product of the condensation of N,N'-bis(2,2,6,6-tetramethyl-4-piperidyl)hexamethylenediamine and 4-tert-octylamino-2,6-dichloro-1,3,5-s-triazine, tris-(2,2,6,6-tetramethyl-4-piperidyl) nitrilotriacetate, tetrakis(2,2,6,6-tetramethyl-4-piperidyl)-1,2,3,4-butanetetraoate, 1,1'-(1,2-ethanediyl)bis-(3,3,5,5-tetramethylpiperazinone), 4-benzoyl-2,2,6,6-tetramethylpiperidine, 4-stearyloxy-2,2, 6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the product of the condensation of N,N'-bis(2,2,6,6-tetramethyl-4-piperidyl) hexamethylene-diamine and 4-morpholino-2,6-dichloro-1,3,5-triazine, the product of the condensation of 2-chloro-4,6-di(4-n-butylamino-2,2,6,6-tetramethylpiperidyl)1,3,5-triazine and 1,2-bis(3-aminopropylamino)ethane, the product of the condensation of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9,-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione, 2,4-bis[N-(1-cyclohexyloxy-2,2,6,6-tetramethylpiperidin-4-yl)-N-butylamino]-6-(2-hydroxyethyl)amino-1,3,5-triazine, the product of the condensation of 2,4-bis[1-cyclohexyloxy-2,2,6,6-tetramethylpiperidin-4-yl)butylamino]-6-chloro-s-triazine and N,N'-bis(3-aminopropyl)ethylenediamine.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and mixtures thereof with 2-ethoxy-2'-ethyl-5,4'-di-tert-butyloxanilide, and mixtures of o- and p-methoxy- and of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,5-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine and 2-[4-dodecyl/tridecyloxy(2-hydroxypropyl)oxy-2-hydroxyphenyl]-4,6-bis(2,4-dimethylphenyl)-1,3,5-triazine.

8. Phosphites and phosphonites, for example triphenyl phosphite, diphenyl alkylphosphites, phenyl dialkylphosphites, tris(nonylphenyl) phosphite, trilauryl phosphite, trioctadecyl phosphite, distearyl pentaerythritol diphosphite, tris(2,4-di-tert-butylphenyl) phosphite, diisodecylpentaerythritol diphosphite, bis(2,4-di-tert-butylphenyl) pentaerythritol diphosphite, bis(2,6-di-tert-butyl-4-methylphenyl) pentaerythritol diphosphite, bisisodecyloxy-pentaerythritol di-phosphite, bis(2,4-di-tert-butyl-6-methylphenyl) pentaerythritol diphosphite, bis(2,4,6-tri-tert-butylphenyl) pentaerythritol diphosphite, tristearylsorbitol triphosphite, tetrakis-(2,4-di-tert-butylphenyl)-4,4'-biphenylenediphosphonite, 6-isooctyloxy-2,4,8,10-tetra-tert-butyl-12H-di-benz[d,g]-1,3,2-dioxaphosphocine, 6-fluoro-2,4,8,10-tetra-tert-butyl-12-methyl-dibenz[d,g]-1,3,2-dioxaphosphocine, bis(2,4-di-tert-butyl-6-methylphenyl) methylphosphite, and bis(2,4-di-tert-butyl-6-methylphenyl) ethylphosphite.

Examples of UV absorbers and light protection agents suitable as component (d) are also "Krypto-UVA", as are described, for example, in EP 180548. It is also possible to use latent UV absorbers, as described, for example, by Hida et al. in RadTech Asia 97, 1997, page 212.

It is also possible to use additives customary in the art, for example antistats, levelling auxiliaries and adhesion improvers.

To accelerate the photopolymerization it is possible to add, as further additives (d), a large number of amines, for example triethanolamine, N-methyidiethanolamine, ethyl p-dimethylaminobenzoate or Michlers ketone. The action of the amines can be intensified by the addition of aromatic ketones, e.g. of the benzophenone type. Examples of amines which can be used as oxygen scavengers are substituted N,N-dialkylanilines, as described in EP 339841.

Other accelerators, coinitiators and autoxidators are thiols, thioethers, disulfides and phosphines, as described, for example, in EP 438123 and GB 2180358.

It is also possible to add chain transfer reagents customary in the art to the compositions according to the invention. Examples thereof are mercaptans, amines and benzothiazols.

The photopolymerization can also be accelerated by the addition of photosensitizers as further additives (d); these shift and/or broaden the spectral sensitivity. These are, in particular, aromatic carbonyl compounds, for example benzophenone, thioxanthone, in particular also isopropylthioxanthone, anthraquinone and 3-acylcoumarin derivatives, terphenyls, styryl ketones, and 3-(aroylmethylene)thiazolines, camphorquinone, but also eosin, rhodamine and erythrosine dyes.

As photosensitizers, it is also possible, for example, to consider the amines given above. Further examples of such photosensitizers are 1. Thioxanthones thioxanthone, 2-isopropylthioxanthone, 2-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di-[2-(2-methoxyethoxy)ethoxycarbonyl]thioxanthone, 1-ethoxycarbonyl-3-(1-methyl-1-morpholinoethyl)thioxanthone, 2-methyl-6-dimethoxymethylthioxanthone, 2-methyl-6-(1,1-dimethoxybenzyl)thioxanthone, 2-morpholinomethylthioxanthone, 2-methyl-6-morpholinomethylthioxanthone, n-allylthioxanthone-3,4-dicarboximide, n-octylthioxanthone-3,4-dicarboximide, N-(1,1,3,3-tetramethylbutyl)thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-polyethylene glycol ester, 2-hydroxy-3-(3,4-dimethyl-9-oxo-9H-thioxanthon-2-yloxy)-N,N,N-trimethyl-1-propanaminium chloride;

2. Benzophenones benzophenone, 4-phenylbenzophenone, 4-methoxybenzophenone, 4,4'-dimethoxybenzophenone, 4,4'-dimethylbenzophenone, 4,4'-dichlorobenzophenone, 4,4'-dimethylaminobenzophenone, 4,4'-diethylaminobenzophenone, 4-methylbenzophenone, 2,4,6-trimethylbenzophenone, 4-(4-methylthiophenyl) benzophenone, 3,3'-dimethyl-4-methoxybenzophenone, methyl-2-benzoylbenzoate, 4-(2-hydroxyethylthio)

benzophenone, 4-(4-tolylthio)benzophenone, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl)benzophenone, 4-benzoyl-N,N-dimethyl-N-[2-(1-oxo-2-propenyl)oxy]ethylbenzenemethanaminium chloride;

3. 3-Acylcoumarins 3-benzoylcoumarin, 3-benzoyl-7-methoxycoumarin, 3-benzoyl-5,7-di(propoxy)coumarin, 3-benzoyl-6,8-dichlorocoumarin, 3-benzoyl-6-chlorocoumarin, 3,3'-carbonylbis[5,7-di(propoxy)coumarin], 3,3'-carbonylbis(7-methoxycoumarin), 3,3'-carbonylbis(7-diethylaminocoumarin), 3-isobutyroylcoumarin, 3-benzoyl-5,7-dimethoxycoumarin, 3-benzoyl-5,7-diethoxycoumarin, 3-benzoyl-5,7-dibutoxycoumarin, 3-benzoyl-5,7-di(methoxyethoxy)coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)coumarin, 5,7-dimethoxy-3-(1-naphthoyl)coumarin, 3-benzoylbenzo[f]coumarin, 7-diethylamino-3-thienoylcoumarin, 3-(4-cyanobenzoyl)-5,7-dimethoxycoumarin;

4. 3-(Aroylmethylene)thiazolines

3-Methyl-2-benzoylmethylene-β-naphthothiazoline, 3-methyl-2-benzoylmethylenebenzothiazoline, 3-ethyl-2-propionylmethylene-β-naphthothiazoline;

5. Other carbonyl compounds

Acetophenone, 3-methoxyacetophenone, 4-phenylacetophenone, benzil, 2-acetylnaphthalene, 2-naphthaldehyde, 9,10-anthraquinone, 9-fluorenone, dibenzosuberone, xanthone, 2,5-bis(4-diethylaminobenzylidene)cyclopentanone, α-(para-dimethylaminobenzylidene) ketones, such as 2-(4-dimethylaminobenzylidene)indan-1-one or 3-(4-dimethylaminophenyl)-1-indan-5-ylpropenone, 3-phenylthiophthalimide, N-methyl-3,5-di(ethylthio)phthalimide.

The curing process can also be aided, in particular, by pigmented compositions (e.g. with titanium dioxide), also by the addition as additional additive (d) of a component which forms the radicals under thermal conditions, for example an azo compound, such as 2,2'-azobis-(4-methoxy-2,4-dimethylvaleronitrile), a triazene, diazo sulfide, pentazadiene or a peroxy compound, for example hydroperoxide or peroxycarbonate, e.g. t-butyl hydroperoxide, as described, for example, in EP 245639.

As further additive (d), the compositions according to the invention can also comprise a photoreproducible dye, for example xanthene, benzoxanthene, benzothioxanthene, thiazine, pyronine, porphyrin or acridine dyes, and/or a radiation-cleavable trihalomethyl compound. Similar compositions are described, for example, in EP 445624.

Depending on the intended use, further customary additives (d) are optical brighteners, fillers, pigments, both white and coloured pigments, dyes, antistats, wetting agents or levelling auxiliaries.

For the curing of thick and pigmented coatings, the addition of microglass beads or pulverized glass fibres, as described, for example, in U.S. Pat. No. 5,013,768, is suitable.

The formulations can also comprise dyes and/or white or coloured pigments. Depending on the intended use, it is possible to use both inorganic and organic pigments. Such additives are known to the person skilled in the art, examples being titanium dioxide pigments, e.g. of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow or cadmium red. Examples of organic pigments are mono- or bisazo pigments, and metal complexes thereof, phthalocyanine pigments, polycyclic pigments, for example perylene, anthraquinone, thioindigo, quinacridone or triphenylmethane pigments, and diketopyrrolopyrrole, isoindolinone, e.g. tetrachloroisoindolinone, isoindoline, dioxazine, benzimidazolone and quinophthalone pigments. The pigments can be used individually or else as mixtures in the formulations. Depending on the intended use, the pigments are added to the formulations in amounts customary in the art, for example in an amount of from 0.1 to 60% by weight, 0.1 to 30% by weight or 10 to 30% by weight, based on the total composition.

The formulations can, for example, also comprise organic dyes from very diverse classes. Examples are azo dyes, methine dyes, anthraquinone dyes or metal complex dyes. Customary concentrations are, for example, 0.1 to 20%, in particular 1 to 5%, based on the total compositions.

The choice of additives depends on the field of application in question and the properties desired for this field. The above-described additives (d) are customary in the art and are accordingly used in amounts customary in the art.

The invention also provides compositions comprising, as components (a), at least one ethylenically unsaturated photopolymerizable compound which is emulsified or dissolved in water.

Such radiation-curable aqueous prepolymer dispersions are available commercially in many variations. This is understood as meaning a dispersion of water and at least one prepolymer dispersed therein. The concentration of the water in these systems is, for example, 2 to 80% by weight, in particular 30 to 60% by weight. The radiation-curable prepolymers or prepolymer mixture is present, for example, in concentrations of from 95 to 20% by weight, in particular 70 to 40% by weight. In these compositions, the total of the percentages given for water and prepolymers is in each case 100, the auxiliaries and additives being added in varying amounts, depending on the intended use.

The radiation-curable film-forming prepolymers which are dispersed, and often also dissolved, in water are mono- or polyfunctional ethylenically unsaturated prepolymers which can be initiated by free radicals and are known per se for aqueous prepolymer dispersions, which have, for example, a content of from 0.01 to 1.0 mol per 100 g of prepolymer of polymerizable double bonds, and also an average molecular weight of, for example, at least 400, in particular from 500 to 10,000. However, depending on the intended use, prepolymers with higher molecular weights are also suitable.

Polyesters containing polymerizable C—C double bonds and having an acid number of at most 10, polyethers containing polymerizable C—C double bonds, hydroxyl-containing products of the reaction of a polyepoxide containing at least two epoxide groups per molecule with at least one α,β-ethylenically unsaturated carboxylic acid, polyurethane (meth)acrylates, and acrylic copolymers containing α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions based on specific (meth) acrylic alkyl ester polymers are described in EP 41125, and suitable water-dispersible, radiation-curable prepolymers of urethane acrylates can be found in DE 2936039.

As further additives, these radiation-curable aqueous prepolymer dispersions can also comprise the above-described additional additives (d), i.e., for example, dispersion auxiliaries, emulsifiers, antioxidants, light stabilizers, dyes, pigments, fillers, e.g. talc, gypsum, silica, rutile, carbon black, zinc oxide, iron oxides, reaction accelerators, levelling agents, lubricants, wetting agents, thickeners, matting agents, antifoams and other auxiliaries customary in surface coating technology. Suitable dispersion auxiliaries are water-soluble high molecular weight organic compounds having polar groups, for example polyvinyl alcohols, polyvinylpyrrolidone or cellulose ethers. Emulsifiers which may be used are nonionic, and, where appropriate, also ionic, emulsifiers.

The photoinitiators of the formula II or III according to the invention can also be dispersed as such in aqueous solutions and added in this dispersed form to the mixtures to be cured. Treated with suitable nonionic or, where appropriate, also ionic, emulsifiers, the compounds of the formula II or III according to the invention can be incorporated by mixing and e.g. binding into water. This produces stable emulsions which can be used as such as photoinitiators, in particular for aqueous photocurable mixtures as described above.

In certain cases, it may be advantageous to use mixtures of two or more of the photoinitiators according to the invention. It is of course also possible to use mixtures with known photoinitiators, e.g. mixtures with camphorquinone, benzophenone, benzophenone derivatives, in particular alkyl-substituted benzophenones, acetophenone, acetophenone derivatives, for example α-hydroxycycloalkyl phenyl ketones or 2-hydroxy-2-methyl-1-phenylpropanone, dialkoxyacetophenones, α-hydroxy or α-aminoacetophenones, for example 4-methylthiobenzoyl-1-methyl-1-morpholinoethane, 4-morpholinobenzoyl-1-benzyl-1-dimethylaminopropane, 4-aroyl-1,3-dioxolanes, benzoin alkyl ethers and benzil ketals, for example benzil dimethyl ketal, phenyl glyoxalates and derivatives thereof, dimeric phenyl glyoxalates, peresters, e.g. benzophenonetetracarboxylic peresters, as described, for example, in EP 126541, monoacylphosphine oxides, for example (2,4,6-trimethylbenzoyl)phenylphosphine oxide, bisacylphosphine oxides, for example bis(2,6-dimethoxybenzoyl)(2,4,4-trimethylpent-1-yl)phosphine oxide, bis(2,4,6-trimethylbenzoyl)phenylphosphine oxide or bis(2,4,6-trimethylbenzoyl)(2,4-dipentoxyphenyl)phosphine oxide, trisacylphosphine oxides, halomethyltriazines, e.g. 2-[2-(4-methoxyphenyl)vinyl]-4,6-bistrichloromethyl-[1,3,5]triazine, 2-(4-methoxyphenyl)-4,6-bis-trichloromethyl-[1,3,5]triazine, 2-(3,4-dimethoxyphenyl)-4,6-bistrichloromethyl-[1,3,5]triazine, 2-methyl-4,6-bistrichloromethyl-[1,3,5]triazine, hexaarylbisimidazole/coinitiator systems, e.g. ortho-chlorohexaphenylbisimidazole in combination with 2-mercaptobenzothiazole; ferrocenium compounds or titanocenes, for example dicyclopentadienylbis(2,6-difluoro-3-pyrrolophenyl)titantium. Coinitiators which may also be used are borate compounds.

In the case of the use of the photoinitiators according to the invention in hybrid systems, in this connection mixtures of free-radically and cationically curing systems are thus intended, in addition to the free-radical curing agents according to the invention, cationic photoinitiators, for example benzoyl peroxide (other suitable peroxides are described in U.S. Pat. No. 4,950,581, column 19, lines 17–25), aromatic sulfonium, phosphonium or iodonium salts, as described, for example in U.S. Pat. No. 4,950,581, column 18, line 60 to column 19, line 10, or cyclopentadienylareneiron(II) complex salts, e.g. ($\eta^6$-isopropylbenzene)($\eta^5$-cyclopentadienyl)iron(II) hexafluorophosphate, are used.

The invention also provides compositions in which the additional photoinitiators (c) are compounds of the formula VIII, IX, X, XI or mixtures thereof, (VIII)

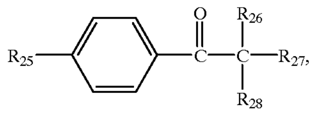

(IX)

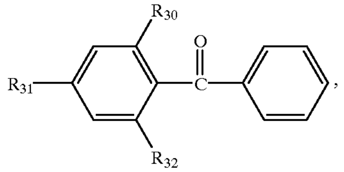

(X)

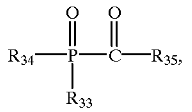

(XI)

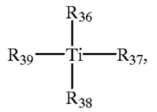

in which $R_{25}$ is hydrogen, $C_1$–$C_{18}$alkyl, $C_1$–$C_{18}$alkoxy, —$OCH_2CH_2$—$OR_{29}$, morpholino, $SCH_3$, a group

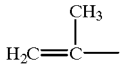

or a group

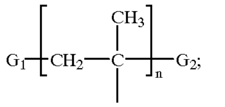

n has a value from 2 to 10;

$G_1$ and $G_2$ independently of one another are end-groups of the polymeric unit, in particular hydrogen or $CH_3$;

$R_{26}$ is hydroxyl, $C_1$–$C_{16}$alkoxy, morpholino, dimethylamino or —$O(CH_2CH_2O)_m$—$C_1$–$C_{16}$alkyl;

$R_{27}$ and $R_{28}$ independently of one another are hydrogen, $C_1$–$C_6$alkyl, phenyl, benzyl, $C_1$–$C_{16}$alkoxy or —$O(CH_2CH_2O)_m$—$C_1$–$C_{16}$alkyl, or $R_{27}$ and R28 together with the carbon atom to which they are bonded form a cyclohexyl ring;

m is a number from 1–20;

where $R_{26}$, $R_{27}$ and $R_{28}$ are not all $C_1$–$C_{16}$alkoxy or —$O(CH_2CH_2O)_m$—$C_1$–$C_{16}$alkyl at the same time, and $R_{29}$ is hydrogen,

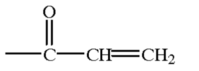 or 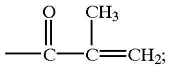

$R_{30}$ and $R_{32}$ independently of one another are hydrogen or methyl;

$R_{31}$ is hydrogen, methyl or phenylthio, where the phenyl ring of the phenylthio radical is unsubstituted or substituted by $C_1$–$C_4$alkyl in the 4-, 2-, 2,4- or 2,4,6-position;

$R_{33}$ and $R_{34}$ independently of one another are $C_1$–$C_{20}$alkyl, cyclohexyl, cyclopentyl, phenyl, naphthyl or biphenyl, where these radicals are unsubstituted or are substituted by halogen, $C_1$–$C_{12}$alkyl and/or $C_1$–$C_{12}$-alkoxy, or $R_{33}$ is an S- or N-containing 5- or 6-membered heterocyclic ring, or are

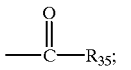

$R_{35}$ is cyclohexyl, cyclopentyl, phenyl, naphthyl or biphenyl, these radicals being unsubstituted or substituted by halogen, $C_1$–$C_4$alkyl and/or $C_1$–$C_4$alkoxy, or $R_{35}$ is an S- or N-containing 5- or 6-membered heterocyclic ring;

$R_{36}$ and $R_{37}$ independently of one another are unsubstituted cyclopentadienyl or cyclopentadienyl substituted once, twice or three times by $C_1$–$C_{18}$alkyl, $C_1$–$C_{18}$alkoxy, cyclopentyl, cyclohexyl or halogen; and $R_{38}$ and $R_{39}$ independently of one another are phenyl which is substituted in at least one of the two ortho positions relative to the titanium-carbon bond by fluorine atoms or $CF_3$, and which on the aromatic ring may contain, as further substituents, unsubstituted pyrrolinyl or pyrrolinyl substituted by one or two $C_1$–$C_{12}$alkyl, di($C_1$–$C_{12}$alkyl)aminomethyl, morpholinomethyl, $C_2$–$C_4$alkenyl, methoxymethyl, ethoxymethyl, trimethylsilyl, formyl, methoxy or phenyl;

or polyoxaalkyl, or $R_{38}$ and $R_{39}$

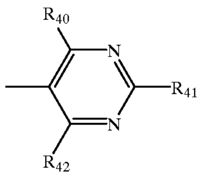 or 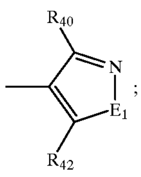

$R_{40}$, $R_{41}$ and $R_{42}$ independently of one another are hydrogen, halogen, $C_2$–$C_{12}$alkenyl, $C_1$–$C_{12}$alkoxy, $C_2$–$C_{12}$alkoxy interrupted by one to four O atoms, cycylohexyloxy, cyclopentyloxy, phenoxy, benzyloxy, unsubstituted phenyl or phenyl substituted by $C_1$–$C_4$alkoxy, halogen, phenylthio or $C_1$–$C_4$-alkylthio; or biphenyl, where $R_{40}$ and $R_{42}$ are not both hydrogen at the same time and in the radical

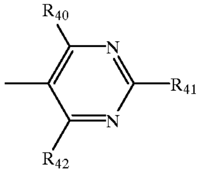

at least one radical $R_{40}$ or $R_{42}$ is $C_1$–$C_{12}$alkoxy, $C_2$–$C_{12}$alkoxy interrupted by one to four O atoms, cyclohexyloxy, cyclopentyloxy, phenoxy or benzyloxy;

$E_1$ is O, S or $NR_{43}$; and $R_{43}$ is $C_1$–$C_8$alkyl, phenyl or cyclohexyl.

$R_{25}$ as $C_1$–$C_{18}$alkyl can have the same meanings as described for the compounds of the formulae I, II or III. Also, $R_{27}$ and $R_{28}$ as $C_1$–$C_6$alkyl and $R_{26}$ as $C_1$–$C_4$alkyl can have the same meanings as described above apart from the respective number of carbon atoms.

$C_1$–$C_{18}$alkoxy is, for example, branched or unbranched alkoxy, for example methoxy, ethoxy, n-propoxy, isopropoxy, n-butoxy, isobutoxy, sec-butoxy, tert-butoxy, pentoxy, hexyloxy, heptyloxy, octyloxy, 2,4,4-trimethylpent-1-yloxy, 2-ethylhexyloxy, nonyloxy, decyloxy, dodecyloxy or octadecyloxy.

$C_2$–$C_{12}$alkoxy has the meanings given above apart from the corresponding number of carbon atoms.

$C_1$–$C_{16}$alkoxy has the same meanings as described above apart from the corresponding number of carbon atoms, and decyloxy, methoxy and ethoxy are preferred, in particular methoxy and ethoxy.

The radical —$O(CH_2CH_2O)_m$—$C_1$–$C_{16}$alkyl stands for 1 to 20 consecutive ethylene oxide units whose chain ends with a $C_1$–$C_{16}$alkyl. Preferably, m is 1 to 10, e.g. 1 to 8, in particular 1 to 6. Preferably, the ethylene oxide unit chain is terminated with a $C_1$–$C_{10}$alkyl, e.g. $C_1$–$C_8$alkyl, in particular with a $C_1$–$C_4$alkyl.

$R_{31}$ as a substituted phenylthio ring is, preferably, p-tolylthio.

$R_{33}$ and $R_{34}$ as $C_1$–$C_{20}$alkyl are linear or branched and are, for example, $C_1$–$C_{12}$alkyl, $C_1$–$C_8$alkyl, $C_1$–$C_6$alkyl or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl or icosyl. Preferably, $R_{33}$ as alkyl is $C_1$–$C_8$alkyl.

$R_{33}$, $R_{34}$ and $R_{35}$ as substituted phenyl are mono- to pentasubstituted, e.g. mono-, di- or trisubstituted, in particular tri- or disubstituted, on the phenyl ring. Substituted phenyl, naphthyl or biphenyl are substituted e.g. with a linear or branched $C_1$–$C_4$alkyl such as methyl, ethyl, n-propyl, isopropyl, n-butyl, isobutyl, s-butyl or t-butyl or with a linear or branched $C_1$–$C_4$alkoxy such as methoxy, ethoxy, n-propoxy, isopropoxy, n-butoxy, isobutoxy, s-butoxy or t-butoxy, preferably with methyl or methoxy.

If $R_{33}$, $R_{34}$ and $R_{35}$ are an S- or N-containing 5- or 6-membered heterocyclic ring, they are, for example, thienyl, pyrrolyl or pyridyl.

In the expression di($C_1$–$C_{12}$alkyl)aminomethyl, $C_1$–$C_{12}$alkyl has the same meanings as given above.

$C_2$–$C_{12}$alkenyl is linear or branched, can be mono- or polyunsaturated and is, for example, allyl, methallyl, 1,1-dimethylallyl, 1-butenyl, 2-butenyl, 1,3-pentadienyl, 1-hexenyl or 1-octenyl, in particular allyl.

$C_1$–$C_4$alkylthio is linear or branched and is, for example, methylthio, ethylthio, n-propylthio, isopropylthio, n-butylthio, isobutylthio, s-butylthio or t-butylthio, preferably methylthio.

$C_2$–$C_4$alkenyl is, for example, allyl, methallyl, 1-butenyl or 2-butenyl.

Halogen is fluorine, chlorine, bromine and iodine, preferably, fluorine, chlorine and bromine.

The term polyoxaalkyl includes $C_2$–$C_{20}$alkyl interrupted by 1 to 9 O atoms and stands, for example, for structural units such as $CH_3$—O—$CH_2$—, $CH_3CH_2$—O—$CH_2CH_2$—, $CH_3O[CH_2CH_2O]_y$—, where y=1–9, —$(CH_2CH_2O)_7CH_2CH_3$, —$CH_2$—$CH(CH_3)$—O—$CH_2$—$CH_2CH_3$.

Preference is given to compositions in which $R_{25}$ is hydrogen, —$OCH_2CH_2$—$OR_{29}$, morpholino, $SCH_3$, a group

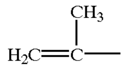

or a group

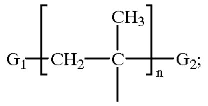

$R_{26}$ is hydroxyl, $C_1$–$C_{16}$alkoxy, morpholino or dimethylamino;

$R_{27}$ and $R_{28}$ independently of one another are $C_1$–$C_4$alkyl, phenyl, benzyl or $C_1$–$C_{16}$alkoxy, or $R_{27}$ and $R_{28}$ together with the carbon atom to which they are bonded form a cyclohexyl ring;

$R_{29}$ is hydrogen or

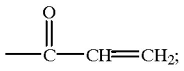

$R_{30}$, $R_{31}$ and $R_{32}$ are hydrogen;

$R_{33}$ is $C_1$–$C_{12}$alkyl, unsubstituted phenyl or phenyl substituted by $C_1$–$C_{12}$alkyl and/or $C_1$–$C_{12}$alkoxy;

$R_{34}$ is

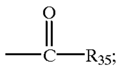

and $R_{35}$ is phenyl which is substituted by $C_1$–$C_4$alkyl and/or $C_1$–$C_4$alkoxy.

Preferred compounds of the formulae VIII, IX, X and XI are α-hydroxycyclohexyl phenyl ketone or 2-hydroxy-2-methyl-1-phenylpropanone, (4-methylthiobenzoyl)-1-methyl-1-morpholinoethane, (4-morpholinobenzoyl)-1-benzyl-1-dimethylaminopropane, benzil dimethyl ketal, (2,4,6-trimethylbenzoyl)phenylphosphine oxide, bis(2,6-dimethoxybenzoyl)-(2,4,4-trimethyl-pent-1-yl)phosphine oxide, bis(2,4,6-trimethylbenzoyl)phenylphosphine oxide or bis(2,4,6-trimethylbenzoyl)(2,4-dipentoxyphenyl) phosphine oxide and dicyclopentadienylbis(2,6-difluoro-3-pyrrolo)titanium.

Preference is also given to compositions in which, in the formula VIII $R_{27}$ and $R_{28}$ independently of one another are $C_1$–$C_6$alkyl, or together with the carbon atom to which they are bonded form a cyclohexyl ring, and $R_{26}$ is hydroxyl.

The proportion of compounds of the formula II and/or III (photoinitiator component (b)) in the mixture with compounds of the formulae VIII, IX, X and/or XI (=photoinitiator component (c)) is 5 to 99%, e.g. 20–80%, preferably 25 to 75%.

Also important are compositions in which, in the compounds of the formula VIII, $R_{27}$ and $R_{28}$ are identical and are methyl, and $R_{26}$ is hydroxyl or isopropoxy.

Likewise preferred are compositions comprising compounds of the formula II and/or III and compounds of the formula X in which $R_{33}$ is unsubstituted or mono- to tri- $C_1$–$C_{12}$alkyl- and/or $C_1$–$C_{12}$alkoxy-substituted phenyl or $C_1$–$C_{12}$alkyl;

$R_{34}$ is the group

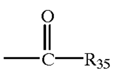

or phenyl; and $R_{35}$ is phenyl substituted by one to three $C_1$–$C_4$alkyl or $C_1$–$C_4$alkoxy.

Of particular interest are compositions as described above which comprise photoinitiator mixtures of the formulae II, III, VIII, IX, X and/or XI and are liquid at room temperature.

The preparation of the compounds of the formulae VIII, IX, X and XI is generally known to the person skilled in the art and some of the compounds are available commercially. The preparation of oligomeric compounds of the formula VIII is described, for example, in EP 161463. A description of the preparation of compounds of the formula IX can, for example, be found in EP 209831. The preparation of compounds of the formula X is disclosed, for example, in EP 7508, EP 184095 and GB 2259704. The preparation of compounds of the formula XI is described, for example, in EP 318894, EP 318893 and EP 565488.

The photopolymerizable compositions advantageously comprise the photoinitiator in an amount of from 0.05 to 20% by weight, e.g. 0.05 to 15% by weight, preferably 0.1 to 5% by weight, based on the composition. The amount of photoinitiator stated is based on the total of all added photoinitiators if mixtures thereof are used, i.e. both on the photoinitiator (b) and on the photoinitiators (b)+(c).

Compounds according to the invention in which $Z_1$ or $Z_2$ are siloxane-containing radicals are particularly suitable as photoinitiators for surface coatings, in particular vehicle paints. These photoinitiators are not distributed as homogeneously as possible in the formulation to be cured, but enriched in a targeted manner on the surface of the coating to be cured, i.e. a targeted orientation of the initiator to the surface of the formulation takes place.

The photopolymerizable compositions can be used for various purposes, for example as printing inks, such as screen printing inks, flexographic printing inks or offset printing inks, as clearcoats, as colour coats, as white coats, e.g. for wood or metal, as powder coatings, as paints, inter alia for paper, water, metal or plastic, as daylight-curable coatings for marking buildings and roads, for photographic reproduction processes, for holographic recording materials, for image recording processes or for the production of printing plates which can be developed using, for example, organic solvents or aqueous-alkaline media, for the production of masks for screen printing, as dental filling materials, as adhesives, as pressure-sensitive adhesives, as laminating resins, as photoresists, e.g. galvanoresists, etch or permanent resists, both liquid and dry films, as photostructurable dielectrics, and as solder stopping masks for electronic circuits, as resists for the preparation of colour filters for any type of screen or for producing structures in the production process of plasma displays and electroluminescence displays, for the production of optical switches, optical gratings (interference gratings), for the preparation of three-dimensional objects by mass curing (UV curing in transparent moulds) or by the stereolithography process, as is described, for example, in U.S. Pat. No. 4,575,330, for the preparation of composite materials (e.g. styrenic polyesters which may contain glass fibres and/or other fibres and other auxiliaries) and other thick-layer materials, for the preparation of gel coats, for the coating or sealing of electronic components or as coatings for optical fibres. The compositions are also suitable for the preparation of optical lenses, e.g. contact lenses and Fresnel lenses, and for the preparation of medical instruments, auxiliaries or implants.

The compositions are also suitable for the preparation of gels having thermotropic properties. Such gels are described, for example, in DE 19700064 and EP 678534.

Furthermore, the compositions can be used in dry-film paints, as are described, for example, in Paint & Coatings Industry, April 1997, 72 or Plastics World, Volume 54, No. 7, page 48(5).

The compounds according to the invention can also be used as initiators for emulsion, bead or suspension polymerizations or as initiators of a polymerization for the fixing of ordered states of liquid-crystalline mono- and oligomers, or as initiators for the fixing of dyes to organic materials.

In surface coatings, mixtures of a prepolymer with polyunsaturated monomers are often used which also contain a monounsaturated monomer. The prepolymer here is primarily responsible for the properties of the coating film, and variation thereof allows the person skilled in the art to influence the properties of the cured film. The polyunsaturated monomer functions as a crosslinking agent which renders the coating film insoluble. The monounsaturated monomer functions as a reactive diluent, by means of which the viscosity is reduced without the need to use a solvent.

Unsaturated polyester resins are mostly used in two-component systems together with a monounsaturated monomer, preferably with styrene. For photoresists, specific one-component systems are often used, for example polymaleimides, polychalcones or polyimides, as are described in DE 2308830.

The compounds according to the invention and mixtures thereof may also be used as free-radical photoinitiators or photoinitiating systems for radiation-curable powder coatings. The powder coatings may be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (e.g. methyl methacrylamide glycolate) and with a free-radical photoinitiator according to the invention, as described, for example, in the paper "Radiation Curing of Powder Coating", Conference Proceedings, Radtech Europe 1993 by M. Wittig and Th. Gohmann. Similarly, free-radically UV-curable powder coatings can be formulated by mixing unsaturated polyester resins with solid acrylates, methacrylates or vinyl ethers and with a photoinitiator (or photoinitiator mixture) according to the invention. The powder coatings can also comprise binders, as described, for example, in DE 4228514 and EP 636669. The UV-curable powder coatings can also comprise white or coloured pigments. Thus, for example, preferably rutile titanium dioxide may be used in concentrations of up to 50% by weight in order to obtain a cured powder coating with good coverage. The process normally involves electrostatic or tribostatic spraying of the powder onto the substrate, for example metal or wood, melting the powder by heating and, after a smooth film has formed, radiation-curing of the coating with ultraviolet and/or visible light, e.g. using medium-pressure mercury lamps, metal halide lamps or xenon lamps. A particular advantage of the radiation-curable powder coatings compared with their thermally curable counterparts is that the flow time after the melting of the powder particles can be extended as desired in order to ensure the formation of a smooth, high-gloss coating. In contrast to thermally curable systems, radiation-curable powder coatings can be formulated without the desired effect of a reduction in their service life such that they melt at relatively low temperatures. For this reason, they are also suitable as coatings for heat-sensitive substrates, for example wood or plastics.

In addition to the photoinitiators according to the invention, the powder coating formulations can also comprise UV absorbers. Appropriate examples have been listed above under points 1–8.

The photocurable compositions according to the invention are suitable, for example, as coating substances for substrates of all kinds, e.g. wood, textiles, paper, ceramic, glass, plastics such as polyesters, polyethylene terephthalate, polyolefins or cellulose acetate, in particular in the form of films, and also metals such as Al, Cu, Ni, Fe, Zn, Mg or Co and GaAs, Si or $SiO_2$, on which a protective coating or, for example by imagewise exposure, an image is to be applied.

The substrates can be coated by applying a liquid composition, a solution or suspension to the substrate. The choice of solvent and the concentration depend primarily on the type of composition and on the coating procedure. The solvent should be inert, i.e. it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

Using known coating processes, the formulation is applied to a substrate, e.g. by spincoating, dip coating, knife coating, curtain coating, brushing, spraying, especially, for example, by electrostatic spraying and reverse-roll coating, and by electrophoretic deposition. It is also possible to apply the photosensitive layer to a temporary, flexible support and then to coat the final substrate, e.g. a copper-laminated circuit board, by means of layer transfer via lamination.

The amount applied (layer thickness) and the type of substrate (layer support) are dependant on the desired field of application. The suitable layer thicknesses for the respective fields of application, e.g. in the photoresist field, printing ink field or paint field are known to the person skilled in the art. Depending on the field of application, the layer thickness range generally includes values from about 0.1 $\mu$m to more than 10 mm.

The radiation-sensitive compositions according to the invention are used, for example, as negative resists which have very high photosensitivity and can be developed in an aqueous-alkaline medium without swelling. They are suitable as photoresists for electronics, such as galvanoresists, etch resists, both in liquid and also dry films, solder stopping resists, as resists for the production of colour filters for any desired type of screen, or for the formation of structures in the manufacturing process of plasma displays and electroluminescence displays, for the production of printing plates, for example offset printing plates, for the production of printing formes for typographic printing, planographic printing, intaglio printing, flexographic printing or screen printing formes, the production of relief copies, e.g. for the production of texts in Braille, for the production of stamps, for use in moulding etching or use as microresists in the production of integrated circuits. The compositions may also be used as photostructurable dielectrics, for the encapsulation of materials or as insulator coating for the production of computer chips, printed circuits and other electrical or electronic components. The possible layer supports and the processing conditions of the coated substrates are varied accordingly.

The compounds according to the invention are also used for the production of single-layer or multilayer materials for image recording or image duplication (copies, reprography), which may be monotone or multicoloured. Furthermore, these materials can also be used as colour testing systems. In this technology, it is also possible to use formulations which contain microcapsules and, to generate the image, a thermal step can be connected downstream of the exposure step. Such systems and technologies and their applications are described, for example, in U.S. Pat. No. 5,376,459.

For photographic information recording, films made of polyester, cellulose acetate or plastic-coated papers, for example, are used, and for offset printing formes, specially treated aluminium, for example, is used, for the production of printed circuits, copper-faced laminates, for example, are used, and for the production of integrated circuits, silicon wafers are used. The usual layer thicknesses for photographic materials and offset printing forms are generally about 0.5 $\mu$m to 10 $\mu$m, and for printed circuits are from 1.0 $\mu$m to about 100 $\mu$m.

After the substrates have been coated, the solvent is usually removed by drying, to leave a layer of the photoresist on the support. The term "imagewise" exposure encompasses both exposure via a photomask containing a predetermined pattern, for example a diapositive, exposure by a laser beam which is moved, for example under control by a computer, over the surface of the coated substrate, thereby generating an image, and irradiation with computer-controlled electron beams. It is also possible to use masks of liquid crystals which can be controlled pixel by pixel in order to generate digital images, as described, for example, by A. Bertsch, J. Y. Jezequel, J. C. Andre in Journal of Photochemistry and Photobiology A: Chemistry 1997, 107, p. 275–281 and by K.-P. Nicolay in Offset Printing 1997, 6, p. 34–37.

Conjugated polymers, for example polyanilines, can be converted from a semiconducting state to a conducting state by doping with protons. The photoinitiators according to the invention can also be used for the imagewise exposure of polymerizable compositions which contain such polymers in order to form conducting structures (in the irradiated zones) which are embedded in the insulating material (unexposed zones). Such materials can, for example, be used as wiring or connecting components for the production of electrical or electronic components.

Following the imagewise exposure of the material and prior to the developing, it may be advantageous to carry out a thermal treatment for a relatively short period. Here, only the exposed parts are thermally cured. The temperatures used are generally 50–150° C., preferably 80–130° C.; the thermal treatment time is usually between 0.25 and 10 minutes.

Furthermore, the photocurable composition can be used in a process for the production of printing formes or photoresists, as described, for example, in DE 4013358. Herein, prior to, simultaneously with or following the imagewise irradiation, the composition is briefly exposed to visible light having a wavelength of at least 400 nm without a mask. Following the exposure and the optional thermal treatment, the unexposed areas of the photoresist are removed using a developer in a manner known per se.

As already mentioned, the compositions according to the invention can be developed by aqueous-alkaline media. Suitable aqueous-alkaline developer solutions are, in particular, aqueous solutions of tetraalkylammonium hydroxides or of alkali metal silicates, phosphates, hydroxides and carbonates. Relatively small amounts of wetting agents and/or organic solvents can also be added to these solutions. Typical organic solvents which may be added to the developer liquids in small amounts are, for example, cyclohexanone, 2-ethoxyethanol, toluene, acetone and mixtures of such solutions.

Photocuring is of great importance for printing inks since the drying time of the binder is a crucial factor for the production rate of graphic products and should be in the order of magnitude of fractions of seconds. UV-curable inks are of importance particularly for screen, flexographic and offset printing.

As already mentioned, the mixtures according to the invention are also highly suitable for the production of printing plates. Here, mixtures of soluble linear polyamides or styrene/butadiene or styrene/isoprene rubber, polyacrylates or polymethyl methacrylates containing carboxyl groups, polyvinyl alcohols or urethane acrylates with photopolymerizable monomers, for example acryl- or methacrylamides or acrylic or methacrylic esters, and a photoinitiator, for example, are used. Films and plates made from these systems (wet or dry) are exposed via the negative (or positive) of the print original, and the uncured parts are subsequently washed out using a suitable solvent.

A further field of use for photocuring is the coating of metals, for example the coating of metal sheets and tubes, cans or bottlecaps, and the photocuring of plastic coatings, for example PVC-based floor or wall coverings. Examples of the photocuring of paper coatings are the colourless coating of labels, record sleeves or book covers.

Likewise of interest is the use of the compounds according to the invention for the curing of mouldings made from composite materials. The composite material consists of a self-supporting matrix material, e.g. a glass-fibre fabric, or else, for example, plant fibres [cf. K.-P. Mieck, T. Reussmann in Kunststoffe 85 (1995), 366–370], which is impregnated with the photocuring formulation. Mouldings made of composite materials produced using the compounds according to the invention have high mechanical stability and resistance. The compounds according to the invention can also be used as photocuring agents in moulding, impregnation or coating materials, as described, for example, in EP 7086. Such materials are, for example, fine coating resins, which are subject to strict requirements with regard to their curing activity and yellowing resistance, fibre-reinforced mouldings, for example planar or longitudinally or transversely corrugated light-diffusing panels. Processes for the production of such mouldings, for example hand lay-up techniques, fibre lay-up spraying, centrifugal or winding techniques, are described, for example, by P. H. Selden in "Glasfaserverstärkte Kunststoffe" [Glass-fibre-reinforced plastics], page 610, Springer Verlag Berlin-Heidelberg-New York 1967. Examples of articles which may be produced by this method are boats, chipboard or plywood panels coated on both sides with glass-fibre-reinforced plastic, pipes, sport articles, roof coverings, and containers etc. Further examples of moulding, impregnation and coating materials are UP resin fine coatings for mouldings containing glass fibres (GFP), e.g. corrugated sheets and paper laminates. Paper laminates may be based on urea or melamine resins. The fine coating is produced on a support (e.g. a film) prior to the production of the laminate. The photocurable compositions according to the invention can also be used for casting resins or for embedding articles, e.g. electronic components etc. Moreover, they can also be used for the lining of cavities and pipes. For curing, medium-pressure mercury lamps are used, as are customary in UV curing. However, less intensive lamps are also of particular interest, e.g. those of the type TL 40W/03 or TL40W/05. The intensity of these lamps corresponds approximately to that of sunlight. It is also possible to use direct sunlight for the curing. It is a further advantage that the composite material can be removed from the light source in a partially cured, plastic state and can be deformed. Curing is then carried out to completion.

The compositions and compounds according to the invention can also be used for the preparation of optical waveguides and optical switches, use being made of the generation of a difference in the refractive index between exposed and unexposed areas.

Also important is the use of photocurable compositions for imaging processes and for the optical production of information carriers. Here, as already described above, the coat (wet or dry) applied to the support is irradiated with UV or visible light via a photomask and the unexposed areas of the coat are removed by treatment with a solvent (=developer). The photocurable layer can also be applied to the metal by an electrodeposition technique. The exposed areas are crosslinked/polymeric and thus insoluble and remain on the support. Appropriate coloration produces visible images. If the support is a metallicized layer, then the metal can be removed from the unexposed areas by etching after exposure and developing, or can be strengthened by electroplating. Printed electronic circuits and photoresists can be produced in this way.

The photosensitivity of the compositions according to the invention generally ranges from about 200 nm to about 600 nm (UV range). Suitable radiation comprises, for example, sunlight or light from artificial light sources. Therefore, a large number of very different types of light sources can be used. Point sources and flat radiators (lamp carpets) are suitable. Examples are: carbon arc lamps, xenon arc lamps, medium-pressure, high-pressure and low-pressure mercury lamps, optionally doped with metal halides (metal halogen lamps), microwave-stimulated metal vapour lamps, excimer lamps, superactinic fluorescent tubes, fluorescent lamps, incandescent argon lamps, flashlights, photographic floodlight lamps, light-emitting diodes (LED), electron beams and X-rays. The distance between the lamp and the substrate to be exposed according to the invention can vary depending on the intended use and lamp type and intensity, e.g. between 2 cm and 150 cm. Of particular suitability are laser light sources, e.g. excimer lasers, such as krypton F lasers for exposure at 248 nm. It is also possible to use lasers in the visible region. Using this method it is possible to produce printed circuits in the electronics industry, lithographic offset printing plates or relief printing plates, and also photographic image recording materials.

The invention therefore also provides a process for the photopolymerization of nonvolatile monomeric, oligomeric or polymeric compounds having at least one ethylenically unsaturated double bond, which comprises irradiating a composition as described above with light in the range from 200 to 600 nm. The invention also provides for the use of the compounds of the formula II or III as photoinitiators for the photopolymerization of nonvolatile monomeric, oligomeric or polymeric compounds having at least one ethylenically unsaturated double bond by irradiation with light in the range from 200 to 600 nm.

The invention also provides for the use of the above-described composition or a process for the preparation of pigmented and unpigmented surface coatings, printing inks, for example screen printing inks, offset printing inks, flexographic printing inks, powder coatings, printing plates, adhesives, dental compositions, optical waveguides, optical switches, colour testing systems, composite materials, gel coats, glass fibre cable coatings, screen printing stencils, resist materials, colour filters, use for the encapsulation of electrical and electronic components, for the production of magnetic recording materials, for the production of three-dimensional objects using stereolithography, for photographic reproductions, and for use as image recording material, in particular for holographic recordings, for decolouring materials, for decolouring materials for image recording materials, for image recording materials using microcapsules.

The invention likewise provides a coated substrate which has been coated on at least one surface with a composition as described above, and also a process for the photographic production of relief images in which a coated substrate is subjected to imagewise exposure and then the unexposed portions are removed with a solvent. The imagewise exposure can be carried out via a mask or by means of a laser beam. Of particular interest here is exposure by means of a laser beam.

The examples below illustrate the invention in more detail, although it is not intended that the invention be limited to the examples. Unless stated otherwise, parts and percentages are based, as elsewhere in the description and in the claims, on the weight. Wherever reference is made to alkyl or alkoxy radicals having more than three carbon atoms without stating the isomer, then the n-isomers are always intended.

EXAMPLE 1

Preparation of lithium (2,4,6-trimethylbenzoyl) isobutylphosphine 34.4 ml (0.055 mol, +10%) of butyllithium 1.6M are slowly added dropwise, at 0° C.–10° C., to 4.5 g (0.025 mol) of isobutylphosphine (50% solution in toluene) in 30 ml of tetrahydrofuran. At the same temperature, 4.6 g (0.025 mol) of 2,4,6-trimethylbenzoyl chloride are then added dropwise. After warming to room temperature, the title compound is obtained as an orange suspension. The shift signal δ in the $^{31}$P-NMR spectrum appears at 50 ppm, measured against $CDCl_3$ as reference.

EXAMPLE 2

Preparation of lithium (2,4,6-trimethylbenzoyl)(2,4,4-trimethylpentyl)phosphine The compound is obtained analogously to the process described in example 1 using 2,4,6-trimethylbenzoyl chloride and 2,4,4-trimethylpentylphosphine as starting materials. The shift signal δ in the $^{31}$P-NMR spectrum appears at 49.2 ppm, measured against $CDCl_3$ as reference.

EXAMPLE 3

Preparation of 2,4,6-trimethylbenzoylisobutylphosphine

The suspension obtained as described in example 1 is added dropwise to a mixture of toluene/water and acetic acid. The organic phase is separated off, dried over magnesium sulfate and evaporated on a rotary evaporator (Rotavap) under argon. The residue is distilled using bulb-tube oven distillation at 110° C. and 0.1 torr. 6 g of the title compound are obtained as a pale yellow oil. The shift signal δ [ppm] in the $^{31}$P-NMR spectrum appears at −37.5.

Shift signals δ [ppm] in the $^{1}$H-NMR spectrum: 1.01 (dd); 1.85 (m); 1.98 (m); 2.23 (s); 2.28 (s); 3.91 (t); 4.66 (t; 1H on the P) 6.82 (s); (measured in $C_6D_6$).

EXAMPLE 4

Preparation of 2,4,6-trimethylbenzoylisobutylbenzylphospine oxide 4.30 g (0.025 mol) of benzyl bromide are slowly added dropwise at room temperature to the suspension obtained as described in example 1. After stirring for 1 hour at room temperature, the orange reaction suspension is evaporated on a Rotavap. The residue is taken up in 50 ml of toluene and treated with 4.2 g (0.0375 mol) of hydrogen peroxide 30%. After stirring for 2 hours at 20–30° C., the reaction is complete. The reaction emulsion is poured onto water and washed with aqueous saturated sodium hydrogencarbonate solution, then dried over magnesium sulfate and filtered. The filtrate is evaporated on a Rotavap. The residue is purified over silica gel and dried in a high vacuum. 6.0 g of the title compound are obtained as a yellow viscous oil.

The shift signal δ in the $^{31}$P-NMR spectrum appears at 39.6 ppm, measured against $CDCl_3$ as reference.

The corresponding signals in the $^{1}$H-NMR spectrum (ppm), measured in $CDCl_3$, are: 7.1–7.2 (m), 6.7 (s), 3.1–3.4 (m), 2.15 (s), 2.0 (s), 1.6–1.9 (m) and 0.87–0.93 (q).

EXAMPLES 5–14

Were Prepared Analogously

The compounds of examples 5–14 are obtained analogously to the method described in example 4 using the corresponding starting materials. The structures and analytical data are given in table 1.

TABLE 1

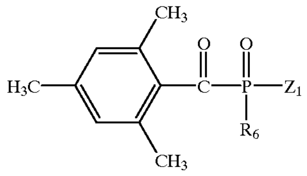

| Ex. | $R_6$ | $Z_1$ | Starting materials | NMR data δ in [ppm] |
|---|---|---|---|---|
| 5 | 2,4,4-trimethyl-pentyl | benzyl | lithium (2,4,6-tri-methylbenzoyl)-2,4,4-trimethyl-pentylphospine/ benzyl bromide | $^{31}$P: 39.25 $^{1}$H: 0.97–0.85 (d); 1.01–1.05 (q); 1.19–1.24 (t); 1.42–1.97 (m); 1.97 (s); 1.99–2.22 (m); 3.19–3.50 (m), 4.03–5.53 (q); 6.78 (s); 7.14–7.36 (m) |
| 6 | 2,4,4-trimethyl-pentyl | allyl | lithium (2,4,6-tri-methylbenzoyl)-2,4,4-trimethyl-pentylphospine/ allyl bromide | $^{31}$P: 39.06 $^{1}$H: 1.11(d); 1.13–1.70 (t); 1.76–1.39 (m); 1.72–2.14 (m); 2.28–2.31 (d); 2.76–2.88 (m); 5.20–5.27 (m); 5.77–5.90 (m); 6.86 (s) |
| 7 | 2,4,4-trimethyl-pentyl | isobutyl | lithium (2,4,6-tri-methylbenzoyl)-2,4,4-trimethyl-pentylphospine/ isobutyl bromide | $^{31}$P: 42.0 $^{1}$H: 0.95 (d); 1.07–1.37 (m); 1.72–2.15 (m); 2.28 (s); 2.33 (s); 6.86 (s) |
| 8 | 2,4,4-trimethyl-pentyl | 2-ethylhexyl | lithium (2,4,6-tri-methylbenzoyl)-2,4,4-trimethyl-pentylphospine/ 2-ethylhexyl bro-mide | $^{31}$P: 40.77 $^{1}$H: 0.92–0.95 (m); 1.19–1.28 (m); 1.46–1.59 (m); 1.73–2.28 (m); 2.46 (s); 6.69 (s) |
| 9 | isobutyl | n-butyl | lithium (2,4,6-tri-methylbenzoyl)-isobutylphospine/ n-butyl bromide | $^{31}$P: 42.5 $^{1}$H: 1.03 (d); 1.08 (d); 1.55–1.80 (m); 2.25 (m); 2.28 (s); 2.31 (s); 6.86 (s) |

TABLE 1-continued

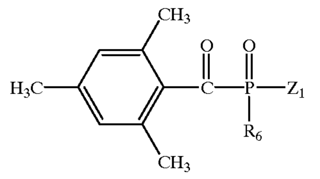

| Ex. | $R_6$ | $Z_1$ | Starting materials | NMR data δ in [ppm] |
|---|---|---|---|---|
| 10 | isobutyl | allyl | lithium (2,4,6-trimethylbenzoyl)-isobutylphospine/allyl bromide | $^{31}$P: 39.2 $^{1}$H: 1.04 (d); 1.07 (d); 1.83 (m); 2.19 (m); 2.28 (s); 2.31 (s); 2.84 (m); 5.21 (m); 5.27 (d); 5.83 (m); 6.86 (s) |
| 11 | isobutyl | $—CH_2(CO)OCH_3$ | lithium (2,4,6-trimethylbenzoyl)-isobutylphospine/methyl bromate | $^{31}$P: 36.0 $^{1}$H: 1.07 (d); 1.09 (d); 2.02 (m); 2.22 (m); 2.29 (s); 2.34 (s); 3.21 (m); 3.72 (s); 6.88 (s) |
| 12 | isobutyl | $—CH_2Si(CH_3)_2Si(CH_3)_3$ | lithium (2,4,6-trimethylbenzoyl)-isobutylphospine/chloromethylpentamethyldisiloxane | $^{31}$P: 41.9 $^{1}$H: 0.10 (s); 0.22 (s); 0.32 (s); 1.02 (d); 1.07 (d); 1.20–1.42 (m); 1.86 (m); 1.96–2.04 (m); 2.28 (s); 2.31 (s); 6.86 (s) |
| 13 | isobutyl | 2-ethylhexyl | lithium (2,4,6-trimethylbenzoyl)-isobutylphospine/2-ethylhexyl bromide | $^{31}$P: 42.8 $^{1}$H: 0.87 (m); 1.06 (d); 1.09 (d); 1.26 (m); 1.45 (m); 1.74 (m); 1.90 (m); 2.17 (m); 2.28 (s); 2.33 (s); 6.86 (s) |
| 14 | isobutyl | $—CH(CH_3)(CO)OC_8H_{17}$ | lithium (2,4,6-trimethylbenzoyl)-isobutylphospine/octyl 2-bromopropionate isomer mixture | $^{31}$P: 34.9 $^{1}$H: 0.81–0.88 (m); 1.07 (dd); 1.15–1.34 (m); 1.40 (d); 1.49 (m); 1.75 (m); 2.05–2.40 (m); 2.26 (s); 2.28 (s); 2.29 (s); 2.33 (s); 3.63 (m); 4.01 (m); 6.85 (s) |

EXAMPLE 15

Preparation of 2,4,6-trimethylbenzoylisobutyl-(2-hydroxycyclohexyl)phosphine oxide 2.30 g (0.02 mol) of cyclohexene oxide are slowly added dropwise at room temperature to a suspension prepared as described in example 1. After heating to 50–55° C. and stirring for 1 hour at this temperature, the reaction mixture is treated with acetic acid and evaporated on a Rotavap. The residue is taken up in 50 ml of toluene and treated with 3.4 g (0.03 mol) of hydrogen peroxide (30%). After stirring for 2 hours between 20–30° C. the reaction is complete. The reaction emulsion is poured onto water and washed with aqueous saturated sodium hydrogencarbonate solution, then dried over magnesium sulfate and filtered. The filtrate is evaporated on a Rotavap. The residue is purified over silica gel and dried under a high vacuum. The title compound is obtained as a white solid.

The shift signal δ [ppm] in the $^{31}$P-NMR spectrum appears at 48.0. Shift signals δ [ppm] in the $^{1}$H-NMR spectrum: 1.08 (d); 1.09 (d); 1.28 (m); 1.42 (m); 1.78–1.94 (m); 2.16 (m); 2.29 (s); 2.34 (s); 3.93 (m); 6.88 (s); (measured in $CDCl_3$).

EXAMPLES 16–17

The compounds of examples 16 and 17 are prepared analogously to the method described in example 15 using the corresponding starting material. The structures and analytical data are shown in table 2.

TABLE 2

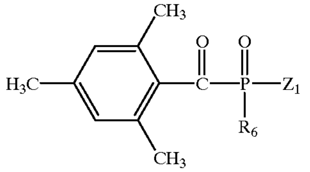

| Ex. | $R_6$ | $Z_1$ | Starting materials | NMR data δ in [ppm] |
|---|---|---|---|---|
| 16 | isobutyl | 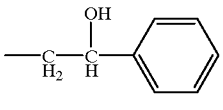 | lithium (2,4,6-trimethylbenzoyl)-isobutylphospine/ styrene oxide | $^{31}$P: 43.8<br>$^{1}$H: 1.08 (d); 1.82 (m); 2.18 (m); 2.27 (m); 2.32 (s); 2.36 (s); 4.55 (s); 5.11 (dd); 6.92(s); 7.29–7.37 (m) (main component - two diastereomers) |
| 17 | isobutyl | 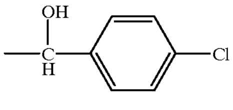 | lithium (2,4,6-trimethylbenzoyl)-isobutylphosphine/ chlorobenzaldehyde | $^{31}$P: 37.7; 38.3<br>$^{1}$H: 0.82 (d); 0.87 (d); 1.71–1.85 (m); 2.22 (s); 2.29 (s); 5.33 (d); 6.85 (s); 7.32 (d); 7.41 (d) (contains second diastereomers) |

EXAMPLE 18

Preparation of 2,4,6-trimethylbenzoyl-(2,6-dimethoxybenzoyl)isobutylphosphine oxide 5.30 g (0.026 mol) of 2,6-dimethoxybenzoyl chloride are slowly added dropwise at room temperature to a suspension as described in example 1. After the mixture has been stirred for 1 hour at room temperature, the orange reaction suspension is concentrated on a Rotavap. The residue is taken up in 50 ml of toluene and treated with 3.4 g (0.03 mol) of hydrogen peroxide (30%). After stirring for 2 hours between 20–30° C., the reaction is complete. The reaction emulsion is poured onto water and washed with aqueous saturated sodium hydrogencarbonate solution, then dried over magnesium sulfate and filtered. The filtrate is evaporated on a Rotavap. The residue is purified over silica gel and dried under an high vacuum. 3.8 g of the title compound are obtained as a slightly yellow solid having an m.p. of 105–106° C.

The shift signal δ [ppm] in the $^{31}$P-NMR spectrum appears at 27.7. Shift signals δ [ppm] in the $^{1}$H-NMR spectrum: 1.05 (dd); 2.12–2.37 (m); 2.26 (2s); 3.56 (s); 6.54 (d); 6.85; 7.35 (t); (measured in $CDCl_3$).

EXAMPLES 19–21

The compounds of examples 19–21 are prepared analogously to the method described in example 18 using the corresponding starting materials. The structures and analytical data are given in table 3.

TABLE 3

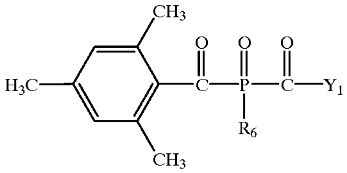

| Ex. | $R_6$ | $Y_1$ | Starting materials | NMR data δ in [ppm] |
|---|---|---|---|---|
| 19 | 2,4,4-trimethylpentyl | 2,6-dimethoxyphenyl | lithium (2,4,6-trimethylbenzoyl)-2,4,4-trimethylpentylphospine/ 2,6-dimethoxybenzoyl chloride | $^{31}$P: 27.6<br>$^{1}$H: 0.7 (d); 0.87–1.22 (m); 1.83–2.43 (m); 3.34 (s); 6.32 (d); 6.66 (s); 7.16 (t) |
| 20 | isobutyl | ethoxy | lithium (2,4,6-trimethylbenzoyl)-iso- | $^{31}$P: 24.1<br>$^{1}$H: 1.07 (d); 1.11 |

TABLE 3-continued

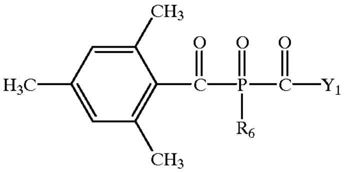

| Ex. | $R_6$ | $Y_1$ | Starting materials | NMR data δ in [ppm] |
|---|---|---|---|---|
| | | | butylphospine/ ethyl chloroformate | (d); 1.29 (t); 2.15–2.27 (m); 2.29 (s); 2.31 (s); 4.32 (m); 6.88 (s) |
| 21 | isobutyl | diethylamino | lithium (2,4,6-trimethylbenzoyl)-isobutylphospine/ diethylcarbamoyl chloride | $^{31}P$: 29.5 $^{1}H$: 1.02 (d); 1.03 (t); 1.09 (d); 1.15 (t); 2.10–2.33 (m); 2.28 (s); 2.29 (s); 3.35 (m); 3.93 (m); 6.85 (s) |

EXAMPLE 22

A UV-curable white coat is prepared by mixing 67.5 parts of polyester acrylate oligomer ($^{RTM}$EBECRYL 830, UCB, Belgium)

5.0 parts of hexanediol diacrylate 2.5 parts of trimethylolpropane triacrylate 25.0 parts of rutile titanium dioxide ($^{RTM}$R-TC2, Tioxide, France)

2.0 parts of the photoinitiator from example 19

The coating is applied to a coil-coated aluminium sheet using a 100 μm slotted doctor knife and then cured. Curing is carried out by conveying the sample twice, on a conveyor belt which is moving at a speed of 10 m/min, beneath a 80 W/cm medium-pressure mercury lamp (Hanovia, USA). The pendulum hardness is then determined in accordance with Konig (DIN53157) in [s]. The pendulum hardness is a measure of the through-curing of the composition. The higher the values, the more effective the curing which has been carried out. A value of 163 s is achieved. After the first pendulum hardness determination, the sample is after-exposed under low-pressure mercury lamps of the type TL 40W/03 (Philips; emission maximum of 430 nm), and after 15 minutes the pendulum hardness is determined again. Following after exposure, a value of 183 s is obtained. The yellowness index in accordance with ASTMD 5-88 is 4.23.

EXAMPLES 23–25

Instead of the photoinitator compound from example 19, 2 parts of the compound according to example 5, 20 or 21 are incorporated into a photocurable formulation as described in example 22, and applied to a coil-coated aluminium sheet as described in example 22. Curing is carried out by conveying the sample repeatedly on a conveyor belt, which is moving at a speed of 10 m/min, beneath an 80 W/cm medium-pressure mercury lamp (Hanovia, USA). The sample is then after-exposed under low-pressure mercury lamps of the TL 40W/03 type (Phillips; emission maximum of 430 nm), and after 15 minutes the pendulum hardness is determined in accordance with König (DIN53157) in [s] and the yellowness index is deterance with ASTMD 1925-88. The results are shown in table 4.

TABLE 4

| Ex. | Compound from Ex. | Number of passages | Pendulum hardness [s] | Yellowness Index |
|---|---|---|---|---|
| 24 | 5 | 4 | 104 | 1.43 |
| 25 | 20 | 3 | 112 | 1.51 |
| 26 | 21 | 3 | 137 | 1.93 |

What is claimed is:

1. A compound of the formula I (I)

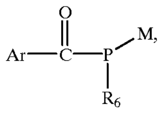

in which

Ar is a group

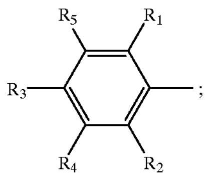

or Ar is cyclopentyl, cyclohexyl, naphthyl, anthracyl, biphenylyl or an O-, S- or N-containing 5- or 6-membered heterocyclic ring, where the radicals cyclopentyl, cyclohexyl, naphthyl, anthracyl, biphenylyl and 5- or 6-membered heterocyclic ring are unsubstituted or substituted by halogen, $C_1$–$C_4$alkyl and/or $C_1$–$C_4$alkoxy;

$R_1$ and $R_2$ independently of one another are $C_1$–$C_{20}$alkyl, $OR_{11}$, $CF_3$ or halogen;

$R_3$, $R_4$ and $R_5$ independently of one another are hydrogen, $C_1$–$C_{20}$alkyl, $OR_{11}$ or halogen;

or in each case two of the radicals $R_1$, $R_2$, $R_3$, $R_4$ and $R_5$ together form $C_1$–$C_{20}$alkylene, which can be interrupted by O, S or $NR_{14}$;

$R_6$ is $C_1$–$C_{24}$alkyl, unsubstituted or substituted by cycloalkenyl, phenyl, CN, $C(O)R_{11}$, $C(O)OR_{11}$, $C(O)N(R_{14})_2$, $OC(O)R_{11}$, $OC(O)OR_{11}$, $N(R_{14})C(O)N(R_{14})$, $OC(O)NR_{14}$, $N(R_{14})C(O)OR_{11}$, cycloalkyl, halogen, $OR_{11}$, $SR_{11}$, $N(R_{12})(R_{13})$ or

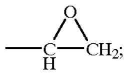

$C_2$–$C_{24}$alkyl which is interrupted once or more than once by nonconsecutive O, S or $NR_{14}$ and which is unsubstituted or substituted by phenyl, $OR_{11}$, $SR_{11}$, $N(R_{12})(R_{13})$, CN, $C(O)R_{11}$, $C(O)OR_{11}$, $C(O)N(R_{14})_2$ and/or

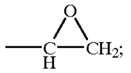

$C_2$–$C_{24}$alkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_5$–$C_{24}$cycloalkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_7$–$C_{24}$arylalkyl which is unsubstituted or substituted on the aryl group by $C_1$–$C_{12}$alkyl, $C_1$–$C_{12}$alkoxy or halogen;

$C_4$–$C_{24}$cycloalkyl which is uninterrupted or interrupted once or more than once by O, S and/or $NR_{14}$ and which is unsubstituted or substituted by $OR_{11}$, $SR_{11}$ or $N(R_{12})(R_{13})$;

or $C_8$–$C_{24}$arylcycloalkyl or $C_8$–$C_{24}$arylcycloalkenyl;

$R_{11}$ is H, $C_1$–$C_{20}$alkyl, $C_2$–$C_{20}$alkenyl, $C_3$–$C_8$cycloalkyl, phenyl, benzyl or $C_2$–$C_{20}$ alkyl, which is interrupted once or more than once by O or S and which is unsubstituted or is substituted by OH and/or SH;

$R_{12}$ and $R_{13}$ independently of one another are hydrogen, $C_1$–$C_{20}$alkyl, $C_3$–$C_8$cycloalkyl, phenyl, benzyl or $C_2$–$C_{20}$ alkyl which is interrupted once or more than once by nonconsecutive O atoms and which is unsubstituted or substituted by OH and/or SH; or $R_{12}$ and $R_{13}$ together are $C_3$–$C_5$alkylene which is uninterrupted or interrupted by O, S or $NR_{14}$;

$R_{14}$ is hydrogen, phenyl, $C_1$–$C_{12}$alkyl or $C_2$–$C_{12}$alkyl which is interrupted once or more than once by O or S and which is unsubstituted or substituted by OH and/or SH; and M is hydrogen, Li, Na or K.

2. A compound of the formula I (I)

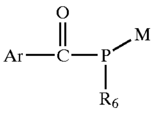

in which

Ar is a group

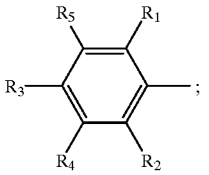

$R_1$ and $R_2$ independently of one another are $C_1$–$C_8$alkyl or $OR_{11}$;

$R_3$, $R_4$ and $R_5$ independently of one another are hydrogen or $C_1$–$C_8$alkyl;

$R_6$ is $C_1$–$C_{12}$alkyl;

$R_{11}$ is H or $C_1$–$C_8$alkyl;

M is hydrogen or Li.

3. A process for the selective preparation of compounds of the formula I according to claim 1, by (1) reaction of an acyl halide of the formula IV (IV)

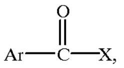

in which

Ar is as defined in claim 1, and

X is Cl or Br;

with a dimetalated organophosphine of the formula V (V)

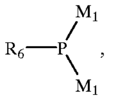

in which $R_6$ is as defined in claim 1; and $M_1$ is Na, Li or K;

in the molar ratio 1:1; and (2) where appropriate, subsequent hydrolysis if compounds of the formula I in which M is hydrogen are to be obtained.

4. A compound of the formula II (II)

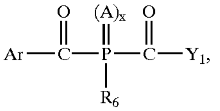

in which

A is O or S;

x is 0 or 1;

Ar is a group

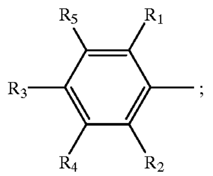

or Ar is cyclopentyl, cyclohexyl, naphthyl, anthracyl, biphenylyl or an O-, S- or N-containing 5- or 6-membered heterocyclic ring, where the radicals cyclopentyl, cyclohexyl, naphthyl, anthracyl, biphenylyl and 5- or 6-membered heterocyclic ring are unsubstituted or substituted by halogen, $C_1$–$C_4$alkyl and/or $C_1$–$C_4$alkoxy;

$R_1$ and $R_2$ independently of one another are $C_1$–$C_{20}$alkyl, $OR_{11}$, $CF_3$ or halogen;

$R_3$, $R_4$ and $R_5$ independently of one another are hydrogen, $C_1$–$C_{20}$alkyl, $OR_{11}$ or halogen;

or in each case two of the radicals $R_1$, $R_2$, $R_3$, $R_4$ and $R_5$ together form $C_1$–$C_{20}$alkylene, which can be interrupted by O, S or $NR_{14}$;

$R_6$ is $C_1$–$C_{24}$alkyl, unsubstituted or substituted by cycloalkenyl, phenyl, CN, $C(O)R_{11}$, $C(O)OR_{11}$, $C(O)N(R_{14})_2$, $OC(O)R_{11}$, $OC(O)OR_{11}$, $N(R_{14})C(O)N(R_{14})$, $OC(O)NR_{14}$, $N(R_{14})C(O)OR_{11}$, cycloalkyl, halogen, $OR_{11}$, $SR_{11}$, $N(R_{12})(R_{13})$ or

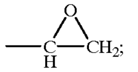

$C_2$–$C_{24}$alkyl which is interrupted once or more than once by nonconsecutive O, S or $NR_{14}$ and which is unsubstituted or substituted by phenyl, $OR_{11}$, $SR_{11}$, $N(R_{12})(R_{13})$, CN, $C(O)R_{11}$, $C(O)OR_{11}$, $C(O)N(R_{14})_2$ and/or

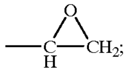

$C_2$–$C_{24}$alkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_5$–$C_{24}$cycloalkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_7$–$C_{24}$arylalkyl which is unsubstituted or substituted on the aryl group by $C_1$–$C_{12}$alkyl, $C_1$–$C_{12}$alkoxy or halogen;

$C_4$–$C_{24}$cycloalkyl which is uninterrupted or interrupted once or more than once by O, S and/or $NR_{14}$ and which is unsubstituted or substituted by $OR_{11}$, $SR_{11}$ or $N(R_{12})(R_{13})$; or $C_8$–$C_{24}$arylcycloalkyl or $C_8$–$C_{24}$arylcycloalkenyl;

$R_{11}$ is H, $C_1$–$C_{20}$alkyl, $C_2$–$C_{20}$alkenyl, $C_3$–$C_8$cycloalkyl, phenyl, benzyl or $C_2$–$C_{20}$ alkyl, which is interrupted once or more than once by nonconsecutive O atoms and which is unsubstituted or substituted by OH and/or SH;

$R_{12}$ and $R_{13}$ independently of one another are hydrogen, $C_1$–$C_{20}$alkyl, $C_3$–$C_8$cycloalkyl, phenyl, benzyl or $C_2$–$C_{20}$ alkyl which is interrupted once or more than once by O or S and which is unsubstituted or substituted by OH and/or SH; or $R_{12}$ and $R_{13}$ together are $C_3$–$C_5$alkylene which is uninterrupted or interrupted by O, S or $NR_{14}$;

$Y_1$ is $C_1$–$C_{18}$alkyl which is unsubstituted or substituted by one or more phenyl; $C_1$–$C_{18}$-halogenoalkyl; $C_2$–$C_{18}$alkyl which is interrupted once or more than once by O or S and which can be substituted by OH and/or SH; unsubstituted $C_3$–$C_{18}$cycloalkyl or $C_3$–$C_{18}$cycloalkyl substituted by $C_1$–$C_{20}$alkyl, $OR_{11}$, $CF_3$ or halogen; $C_2$–$C_{18}$alkenyl; or $Y_1$ is $OR_{11}$, $N(R_{12})(R_{13})$ or one of the radicals

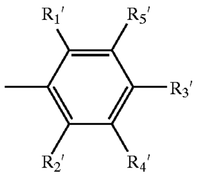

or

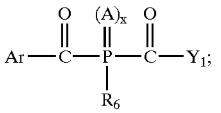

or $Y_1$ is cyclopentyl, cyclohexyl, naphthyl, anthracyl, biphenylyl or an O-, S- or N-containing 5- or 6-membered heterocyclic ring, where the radicals cyclopentyl, cyclohexyl, naphthyl, anthracyl, biphenylyl and 5- or 6-membered heterocyclic ring are unsubstituted or substituted by halogen, $C_1$–$C_4$alkyl and/or $C_1$–$C_4$alkoxy;

$Y_2$ is a direct bond; unsubstituted or phenyl-substituted $C_1$–$C_{18}$alkylene; unsubstituted $C_4$–$C_{18}$-cycloalkylene or $C_4$–$C_{18}$cycloalkylene substituted by $C_1$–$C_{12}$alkyl, $OR_{11}$, halogen and/or phenyl; unsubstituted $C_5$–$C_{18}$cycloalkenylene or $C_5$–$C_{18}$cycloalkenylene substituted by $C_1$–$C_{12}$alkyl, $OR_{11}$, halogen and/or phenyl; unsubstituted phenylene or phenylene substituted one to four times by $C_1$–$C_{12}$alkyl, $OR_{11}$, halogen, —$(CO)OR_{14}$, —$(CO)N(R_{12})(R_{13})$ and/or phenyl;

or $Y_2$ is a radical

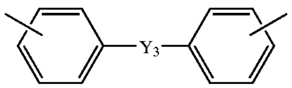

or

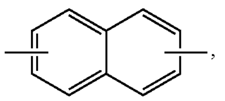

where these radicals are unsubstituted or are substituted one to four times on one or both aromatic ring(s) by $C_1$–$C_{12}$alkyl, $OR_{11}$, halogen and/or phenyl;

$Y_3$ is O, S, SO, $SO_2$, $CH_2$, $C(CH_3)_2$, $CHCH_3$, $C(CF_3)_2$, (CO), or a direct bond;

$R_{14}$ is hydrogen, phenyl, $C_1$–$C_{12}$alkyl or $C_2$–$C_{12}$alkyl which is interrupted once or more than once by O or S and which can be substituted by OH and/or SH;

$R_1$' and $R_2$' independently of one another have the same meanings as given for $R_1$ and $R_2$; and $R_3'$, $R_4'$ and $R_5'$ independently of one another have the same meanings as given for $R_3$, $R_4$ and $R_5$; or in each case two of the radicals $R_1'$, $R_2'$, $R_3'$, $R_4'$ and $R_5'$ together form $C_1$–$C_{20}$alkylene which may be interrupted by O, S or —$NR_{14}$;

with the proviso that $Y_1$ is not identical to Ar by reacting an alkylacylphosphine compound of formula I according to claim 1 with an acid halide of the formula (IV)

(IV)

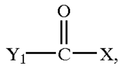

wherein

X is Cl or Br;

in a molar ratio of about 1:1, optionally in a solvent, at a reaction temperature from about −60° C. to about +120° C. to give a phosphine compound of formula II, wherein x is 0, and optionally, subsequent oxidation or sulfurization of the resulting phosphine compound to give the corresponding oxide or sulfide compound wherein x is 1 and A is O or S.

5. A new process for the preparation of monoacylphosphine oxides or sulfides of formula III (III)

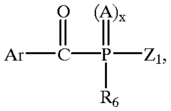

in which

A is O or S;

x is 0 or 1;

Ar is a group

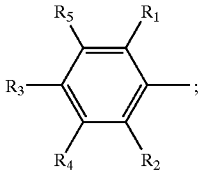

or Ar is cyclopentyl, cyclohexyl, naphthyl, anthracyl, biphenylyl or an O-, S- or N-containing 5- or 6-membered heterocyclic ring, where the radicals cyclopentyl, cyclohexyl, naphthyl, anthracyl, biphenylyl and 5- or 6-membered heterocyclic ring are unsubstituted or substituted by halogen, $C_1$–$C_4$alkyl and/or $C_1$–$C_4$alkoxy;

$R_1$ and $R_2$ independently of one another are $C_1$–$C_{20}$alkyl, $OR_{11}$, $CF_3$ or halogen;

$R_3$, $R_4$ and $R_5$ independently of one another are hydrogen, $C_1$–$C_{20}$alkyl, $OR_{11}$ or halogen;

or in each case two of the radicals $R_1$, $R_2$, $R_3$, $R_4$ and $R_5$ together form $C_1$–$C_{20}$alkylene which can be interrupted by O, S or —$NR_{14}$;

$R_6$ is $C_1$–$C_{24}$alkyl, unsubstituted or substituted by $C_5$–$C_{24}$cycloalkenyl, phenyl, CN, $C(O)R_{11}$, $C(O)OR_{11}$, $C(O)N(R_{14})_2$, $OC(O)R_{11}$, $OC(O)OR_{11}$, $N(R_{14})C(O)N(R_{14})$, $OC(O)NR_{14}$, $N(R_{14})C(O)OR_{11}$, cycloalkyl, halogen, $OR_{11}$, $SR_{11}$, $N(R_{12})(R_{13})$ or

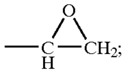

$C_2$–$C_{24}$alkyl which is interrupted once or more than once by nonconsecutive O, S or $NR_{14}$ and which is unsubstituted or substituted by phenyl, $OR_{11}$, $SR_{11}$, $N(R_{12})(R_{13})$, CN, $C(O)R_{11}$, $C(O)OR_{11}$, $C(O)N(R_{14})_2$ and/or

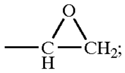

$C_2$–$C_{24}$alkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_5$–$C_{24}$cycloalkenyl which is uninterrupted or interrupted once or more than once by nonconsecutive O, S or $NR_{14}$ and which is unsubstituted or substituted by $OR_{11}$, $SR_{11}$ or $N(R_{12})(R_{13})$;

$C_7$–$C_{24}$arylalkyl which is unsubstituted or substituted on the aryl group by $C_1$–$C_{12}$alkyl, $C_1$–$C_{12}$alkoxy or halogen;

$C_4$–$C_{24}$cycloalkyl which is uninterrupted or interrupted once or more than once by O, S and/or $NR_{14}$ and which is unsubstituted or substituted by $OR_{11}$, $SR_{11}$ or $N(R_{12})(R_{13})$; or $C_8$–$C_{24}$arylcycloalkyl or $C_8$–$C_{24}$arylcycloalkenyl;

$R_{11}$ is H, $C_1$–$C_{20}$alkyl, $C_2$–$C_{20}$alkenyl, $C_3$–$C_8$cycloalkyl, phenyl, benzyl or $C_2$–$C_{20}$alkyl which is interrupted once or more than once by nonconsecutive O atoms and which is unsubstituted or substituted by OH and/or SH;

$R_{12}$ and $R_{13}$ independently of one another are hydrogen, $C_1$–$C_{20}$alkyl, $C_3$–$C_8$cycloalkyl, phenyl, benzyl or $C_2$–$C_{20}$alkyl, which is interrupted once or more than once by O or S and which is unsubstituted or substituted by OH and/or SH; or $R_{12}$ and $R_{13}$ together are $C_3$–$C_5$alkylene which is uninterrupted or interrupted by O, S or $NR_{14}$;

$Z_1$ is $C_1$–$C_{24}$alkyl, which is unsubstituted or substituted once or more than once by $OR_{15}$,$SR_{15}$, $N(R_{16})(R_{17})$, phenyl, halogen, CN, —N═C═A,

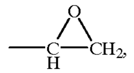 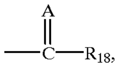

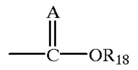 and/or 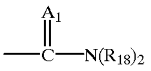

or $Z_1$ is $C_2$–$C_{24}$alkyl which is interrupted once or more than once by O, S or $NR_{14}$ and which can be substituted by $OR_{15}$, $SR_{15}$, $N(R_{16})(R_{17})$, phenyl, halogen,

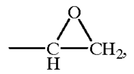 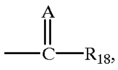

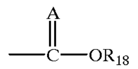 and/or 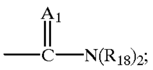

or $Z_1$ is $C_1$–$C_{24}$alkoxy, which is substituted once or more than once by phenyl, CN, —N═C═A,

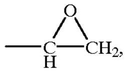
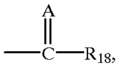
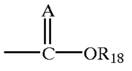
and/or

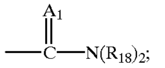
or $Z_1$ is
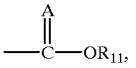

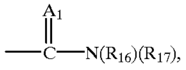
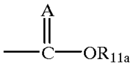
or

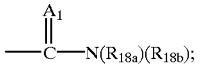

or $Z_1$ is unsubstituted $C_3$–$C_{24}$cycloalkyl or $C_3$–$C_{24}$cycloalkyl substituted by $C_1$–$C_{20}$alkyl, $OR_{11}$, $CF_3$ or halogen; unsubstituted $C_2$–$C_{24}$alkenyl or $C_2$–$C_{24}$alkenyl substituted by $C_6$–$C_{12}$aryl, CN, (CO)$OR_{15}$ or (CO)$N(R_{18})_2$; or $Z_1$ is $C_3$–$C_{24}$cycloalkenyl or is one of the radicals (f)

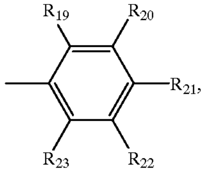

(g)

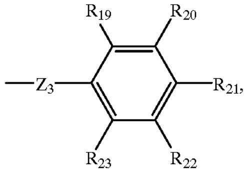

(h)

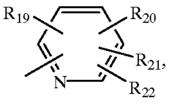

(i)

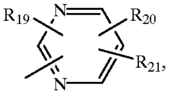

(k)

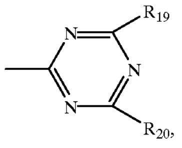

(l)

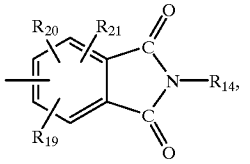

-continued (m)

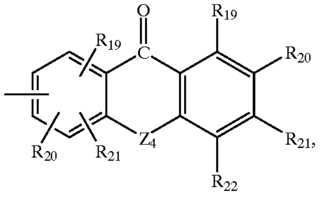

(n)

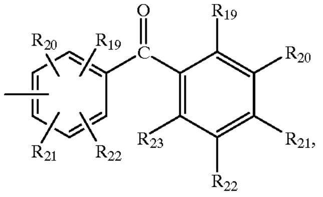

(o)

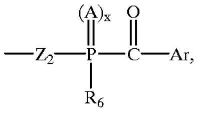

(p)

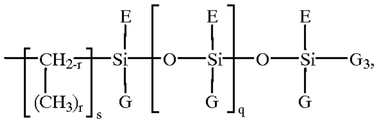

(q)

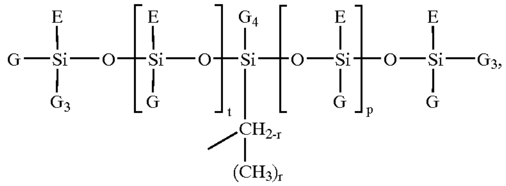

(t)

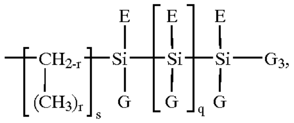

(v)

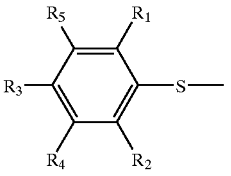
or (w)

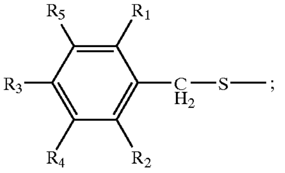

or $Z_1$ is $C_1$–$C_{24}$alkylthio, in which the alkyl radical is uninterrupted or interrupted once or more than once by nonconsecutive O or S, and is unsubstituted or substituted by $OR_{15}$, $SR_{15}$ and/or halogen; with the proviso that $Z_1$ and $R_6$ are not identical;

$A_1$ is O, S or $NR_{18a}$;

$Z_2$ is $C_1$–$C_{24}$alkylene; $C_2$–$C_{24}$alkylene interrupted once or more than once by O, S, or $NR_{14}$; $C_2$–$C_{24}$alkenylene; $C_2$–$C_{24}$alkenylene interrupted once or more than once by O, S or $NR_{14}$; $C_3$–$C_{24}$cycloalkylene; $C_3$–$C_{24}$cycloalkylene interrupted once or more than once by O, S or $NR_{14}$; $C_3$–$C_{24}$cycloalkylene; $C_3$–$C_{24}$cycloalkenylene interrupted once or more than once by O, S or $NR_{14}$; where the radicals $C_1$–$C_{24}$alkylene, $C_2$–$C_{24}$alkylene, $C_2$–$C_{24}$alkenylene, $C_3$–$C_{24}$cycloalkylene and $C_3$–$C_{24}$cycloalkenylene are unsubstituted or are substituted by $OR_{11}$, $SR_{11}$, $N(R_{12})(R_{13})$and/or halogen; or $Z_2$ is one of the radicals

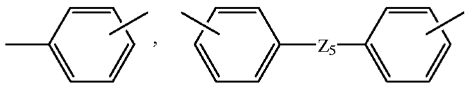

or

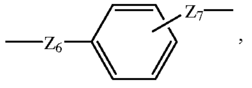

where these radicals are unsubstituted or are substituted on the aromatic by $C_1$–$C_{20}$alkyl; $C_2$–$C_{20}$alkyl which is interrupted once or more than once by nonconsecutive O atoms and which is unsubstituted or substituted by OH and/or SH; $OR_{11}$, $SR_{11}$, $N(R_{12})(R_{13})$, phenyl, halogen, $NO_2$, CN, (CO)—$OR_{11}$, (CO)—$R_{11}$, (CO)—$N(R_{12})(R_{13})$, $SO_2R_{24}$, $OSO_2R_{24}$, $CF_3$ and/or $CCl_3$;

or $Z_2$ is a group (r)

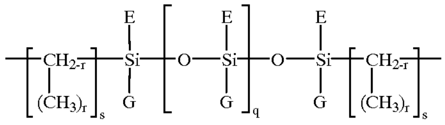

or (u)

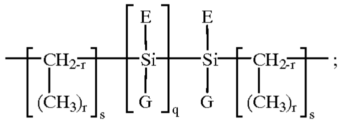

$Z_3$ is $CH_2$, CH(OH), $CH(CH_3)$ or $C(CH_3)_2$;

$Z_4$ is S, O, $CH_2$, C═O, $NR_{14}$ or a direct bond;

$Z_5$ is S, O, $CH_2$, $CHCH_3$, $C(CH_3)_2$, $C(CF_3)_2$, SO, $SO_2$, CO;

$Z_6$ and $Z_7$ independently of one another are $CH_2$, $CHCH_3$ or $C(CH_3)_2$;

r is 0, 1 or 2;

s is a number from 1 to 12;

q is a number from 0 to 50;

t and p are each a number from 0 to 20;

E, G, $G_3$ and $G_4$ independently of one another are unsubstituted $C_1$–$C_{12}$alkyl or $C_1$–$C_{12}$alkyl substituted by halogen, or are unsubstituted phenyl or phenyl substituted by one or more $C_1$–$C_4$alkyl; or are $C_2$–$C_{12}$alkenyl;

$R_{13a}$ is $C_1$–$C_{20}$alkyl substituted once or more than once by $OR_{15}$ or

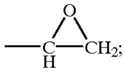

or is $C_2$–$C_{20}$alkyl which is interrupted once or more than once by nonconsecutive O atoms and is unsubstituted or substituted once or more than once by $OR_{15}$, halogen or

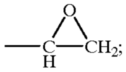

or $R_{11a}$ is $C_2$–$C_{20}$alkenyl, $C_3$–$C_{12}$alkynyl; or $R_{11a}$ is $C_3$–$C_{12}$cycloalkenyl which is substituted once or more than once by halogen, $NO_2$, $C_1$–$C_6$alkyl, $OR_{11}$ or $C(O)OR_{18}$; or $C_7$–$C_{16}$arylalkyl or $C_8$–$C_{16}$arylcycloalkyl;

$R_{14}$ is hydrogen, phenyl, $C_1$–$C_{12}$alkoxy, $C_1$–$C_{12}$alkyl or $C_2$–$C_{12}$alkyl which is interrupted once or more than once by O or S and which is unsubstituted or substituted by OH and/or SH;

$R_{15}$ has one of the meanings given for $R_{11}$ or is a radical

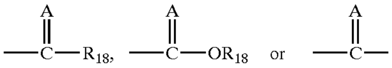

$R_{16}$ and $R_{17}$ independently of one another have one of the meanings given for $R_{12}$ or are a radical

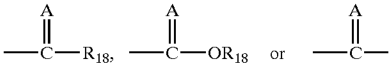

$R_{18}$ is hydrogen, $C_1$–$C_{24}$alkyl, $C_2$–$C_{12}$alkenyl, $C_3$–$C_8$cycloalkyl, phenyl, benzyl; $C_2$–$C_{20}$alkyl which is interrupted once or more than once by O or S and which is unsubstituted or substituted by OH;

$R_{18a}$ and $R_{18b}$ independently of one another are hydrogen; $C_1$–$C_{20}$alkyl, which is substituted once or more than once by $OR_{15}$, halogen, styryl, methylstyryl, —N═C═A or

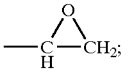

or $C_2$–$C_{20}$alkyl, which is interrupted once or more than once by nonconsecutive O atoms and which is unsubstituted or substituted once or more than once by $OR_{15}$, halogen, styryl, methylstyryl or

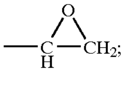

or $R_{18a}$ and $R_{18b}$ are $C_2$–$C_{12}$alkenyl; $C_5$–$C_{12}$cycloalkyl, which is substituted by —N═C═A or —$CH_2$—N═C═A and is additionally unsubstituted or substituted by one or more $C_1$–$C_4$alkyl; or $R_{18a}$ and $R_{18b}$ are $C_6$–$C_{12}$aryl, unsubstituted or substituted once or more than once by halogen, $NO_2$, $C_1$–$C_6$alkyl, $C_2$–$C_4$alkenyl, $OR_{11}$, —N═C═A, —$CH_2$—N═C═A or $C(O)OR_{18}$; or $R_{18a}$ and $R_{18b}$ are $C_7$–$C_{16}$arylalkyl; or $R_{18a}$ and $R_{18b}$ together are $C_8$–$C_{16}$arylcycloalkyl; or $R_{18a}$ and $R_{18b}$ independently of one another are

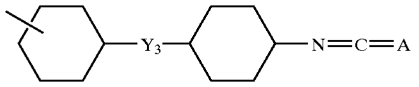

or

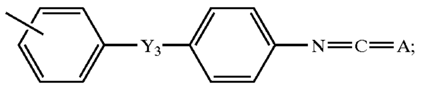

$Y_3$ is O, S, SO, $SO_2$, $CH_2$, $C(CH_3)_2$, $CHCH_3$, $C(CF_3)_2$, (CO), or a direct bond;

$R_{19}$, $R_{20}$, $R_{21}$, $R_{22}$ and $R_{23}$ independently of one another are hydrogen, $C_1$–$C_{20}$alkyl; $C_2$–$C_{20}$alkyl, which is interrupted once or more than once by nonconsecutive O atoms and which is unsubstituted or substituted by OH and/or SH; or $R_{19}$, $R_{20}$, $R_{21}$, $R_{22}$ and $R_{23}$ are $OR_{11}$, $SR_{11}$, $N(R_{12})(R_{13})$, $NO_2$, CN, $SO_2R_{24}$, $OSO_2R_{24}$, $CF_3$, $CCl_3$, halogen; or phenyl which is unsubstituted or substituted once or more than once by $C_1$–$C_4$alkyl or $C_1$–$C_4$alkoxy;

or in each case two of the radicals $R_{19}$, $R_{20}$, $R_{21}$, $R_{22}$ and $R_{23}$ together form $C_1$–$C_{20}$alkylene which is uninterrupted or interrupted by O, S or —$NR_{14}$;

$R_{24}$ is $C_1$–$C_{12}$alkyl, halogen-substituted $C_1$–$C_{12}$alkyl, phenyl, or phenyl substituted by $OR_{11}$ and/or $SR_{11}$;

with the proviso that $R_6$ and $Z_1$ are not identical; by reacting an alkylacylphosphine compound of formula I according to claim 1 with a halide of the formula (VI)

$$Z_1—X \qquad (VI),$$

wherein

X is Cl or Br;

in a molar ratio of about 1:1, optionally in a solvent, at a reaction temperature from about −60° C. to about +120° C. to give a phosphine compound of formula III wherein x is 0, and optionally, subsequent oxidation or sulfurization of the resulting phosphine compound to give the corresponding oxide or sulfide compound wherein x is 1 and A is O or S.

* * * * *

UNITED STATES PATENT AND TRADEMARK OFFICE

CERTIFICATE OF CORRECTION

PATENT NO. : 6,737,549 B1
DATED : May 18, 2004
INVENTOR(S) : Jean-Pierre Wolf et al.

It is certified that error appears in the above-identified patent and that said Letters Patent is hereby corrected as shown below:

<u>Column 88,</u>
Line 54, should read
-- A process for the preparation of Bisacylphosphine oxides or sulfides of Formula II --

<u>Column 90,</u>
Line 25, should read -- 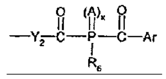 --

<u>Column 91,</u>
Line 24, delete the term "new"

Signed and Sealed this

Sixteenth Day of November, 2004

JON W. DUDAS
*Director of the United States Patent and Trademark Office*